(12) United States Patent
Hyde et al.

(10) Patent No.: US 8,758,679 B2
(45) Date of Patent: *Jun. 24, 2014

(54) SURVEYING STERILIZER METHODS AND SYSTEMS

(75) Inventors: Roderick A. Hyde, Redmond, WA (US);
Edward K. Y. Jung, Bellevue, WA (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 478 days.

This patent is subject to a terminal disclaimer.

(21) Appl. No.: 12/800,814

(22) Filed: May 20, 2010

(65) Prior Publication Data
US 2011/0002821 A1    Jan. 6, 2011

Related U.S. Application Data

(63) Continuation-in-part of application No. 11/584,339, filed on Oct. 20, 2006, now Pat. No. 7,754,156, which is a continuation-in-part of application No. 11/411,207, filed on Apr. 25, 2006, now Pat. No. 7,638,090, which is a continuation-in-part of application No. 11/396,256, filed on Mar. 31, 2006, now Pat. No. 8,277,724.

(51) Int. Cl.
*A61L 2/16* (2006.01)

(52) U.S. Cl.
USPC .................. 422/3; 700/266; 422/20; 422/21; 422/22; 422/23; 422/24; 422/8; 250/461.1; 250/453.11; 250/454.11; 250/455.11

(58) Field of Classification Search
USPC ............ 422/3, 20–24, 28; 250/461.1, 453.11, 250/454.11, 455.11; 700/266
See application file for complete search history.

(56) References Cited

U.S. PATENT DOCUMENTS

| | | | |
|---|---|---|---|
| 2,216,333 A | 10/1940 | White et al. |
| 2,689,837 A | 9/1954 | Darby et al. |
| 2,873,263 A | 2/1959 | Lal |
| 2,875,097 A | 2/1959 | Pritchard |
| 2,986,448 A | 5/1961 | Gates et al. |

(Continued)

FOREIGN PATENT DOCUMENTS

| | | |
|---|---|---|
| CN | 1638632 A | 7/2005 |
| EP | 0693289 A2 | 1/1996 |

(Continued)

OTHER PUBLICATIONS

UK Intellectual Property Office Examination Report Under Section 18(3); App. No. GB0908938.4; Mar. 1, 2011 (received by our Agent on Mar. 3, 2011); pp. 1-5.

(Continued)

*Primary Examiner* — Shogo Sasaki

(57) ABSTRACT

Methods and systems for surveying and sterilizing one or more areas or one or more portions of one or more areas are described.

21 Claims, 24 Drawing Sheets

(56) References Cited

U.S. PATENT DOCUMENTS

| | | |
|---|---|---|
| 3,325,436 A | 6/1967 | Prindle et al. |
| 3,376,110 A | 4/1968 | Shiraeff |
| 3,376,384 A | 4/1968 | Achramowicz |
| 3,480,557 A | 11/1969 | Shiraeff |
| 3,485,787 A | 12/1969 | Haefele et al. |
| 3,827,999 A | 8/1974 | Crossland |
| 3,870,783 A | 3/1975 | Hall et al. |
| 3,953,566 A | 4/1976 | Gore |
| 3,966,902 A | 6/1976 | Chromecek |
| 3,967,478 A | 7/1976 | Guinn |
| 4,042,765 A | 8/1977 | Floyd et al. |
| 4,073,764 A | 2/1978 | Hemmerich et al. |
| 4,087,925 A | 5/1978 | Bienek |
| 4,151,419 A | 4/1979 | Morris et al. |
| 4,169,123 A | 9/1979 | Moore et al. |
| 4,169,124 A | 9/1979 | Forstrom et al. |
| 4,176,240 A | 11/1979 | Sabia |
| 4,187,390 A | 2/1980 | Gore |
| 4,194,041 A | 3/1980 | Gore et al. |
| 4,197,375 A | 4/1980 | Fox |
| 4,208,324 A | 6/1980 | Ramanathan |
| 4,312,907 A | 1/1982 | Hiraoka et al. |
| 4,325,870 A | 4/1982 | Bühler et al. |
| 4,369,284 A | 1/1983 | Chen |
| 4,381,380 A | 4/1983 | LeVeen et al. |
| 4,403,826 A | 9/1983 | Presby |
| 4,443,511 A | 4/1984 | Worden et al. |
| 4,476,255 A | 10/1984 | Bailey et al. |
| 4,499,154 A | 2/1985 | James et al. |
| 4,500,455 A | 2/1985 | Niwa et al. |
| 4,556,464 A | 12/1985 | St. Clair |
| 4,612,444 A | 9/1986 | Ragusa |
| 4,618,213 A | 10/1986 | Chen |
| 4,629,896 A | 12/1986 | Bridgen |
| 4,642,165 A | 2/1987 | Bier |
| 4,643,876 A | 2/1987 | Jacobs et al. |
| 4,688,585 A * | 8/1987 | Vetter .................... 134/56 R |
| 4,688,858 A | 8/1987 | Fennel et al. |
| 4,692,369 A | 9/1987 | Nomi |
| 4,716,183 A | 12/1987 | Gamarra et al. |
| 4,731,541 A | 3/1988 | Shoemaker |
| 4,744,951 A | 5/1988 | Cummings et al. |
| 4,771,482 A | 9/1988 | Shlenker |
| 4,774,324 A | 9/1988 | Loeffler et al. |
| 4,855,412 A | 8/1989 | Dehnert et al. |
| 4,855,413 A | 8/1989 | Dehnert et al. |
| 4,907,316 A | 3/1990 | Kurz |
| 4,925,732 A | 5/1990 | Driskill et al. |
| 4,935,260 A | 6/1990 | Shlenker |
| 4,935,635 A | 6/1990 | O'Harra |
| 4,942,270 A | 7/1990 | Gamarra |
| 4,943,414 A | 7/1990 | Jacobs et al. |
| 5,008,093 A | 4/1991 | Merianos |
| 5,008,106 A | 4/1991 | Merianos et al. |
| 5,030,380 A | 7/1991 | Moschner et al. |
| 5,061,106 A | 10/1991 | Kent |
| 5,069,227 A | 12/1991 | Maronian |
| 5,074,322 A | 12/1991 | Jaw |
| 5,077,047 A | 12/1991 | Biss et al. |
| 5,102,711 A | 4/1992 | Keller et al. |
| 5,113,874 A | 5/1992 | Maronian |
| 5,138,719 A | 8/1992 | Orlianges et al. |
| 5,142,010 A | 8/1992 | Olstein |
| 5,240,675 A | 8/1993 | Wilk et al. |
| 5,269,981 A | 12/1993 | Jameson et al. |
| 5,315,289 A | 5/1994 | Fuller et al. |
| 5,326,841 A | 7/1994 | Fellman |
| 5,357,636 A | 10/1994 | Dresdner, Jr. et al. |
| 5,360,892 A | 11/1994 | Bonsignore et al. |
| 5,403,363 A | 4/1995 | Loeffler et al. |
| 5,428,123 A | 6/1995 | Ward et al. |
| 5,459,879 A | 10/1995 | Fuchs |
| 5,480,915 A | 1/1996 | Burns |
| 5,498,394 A | 3/1996 | Matschke |
| 5,501,669 A | 3/1996 | Conway et al. |
| 5,547,635 A | 8/1996 | Duthie, Jr. |
| 5,549,924 A | 8/1996 | Shlenker et al. |
| 5,557,444 A | 9/1996 | Melville et al. |
| 5,563,238 A | 10/1996 | Bonsignore et al. |
| 5,614,151 A | 3/1997 | LeVay et al. |
| 5,641,566 A | 6/1997 | Kranzler et al. |
| H1670 H | 7/1997 | Aziz et al. |
| 5,644,798 A | 7/1997 | Shah |
| 5,648,003 A | 7/1997 | Liang et al. |
| 5,667,753 A | 9/1997 | Jacobs et al. |
| 5,688,475 A | 11/1997 | Duthie, Jr. |
| 5,731,053 A | 3/1998 | Kuhn et al. |
| 5,733,270 A | 3/1998 | Ling et al. |
| 5,779,795 A | 7/1998 | Bucher et al. |
| 5,782,382 A | 7/1998 | Van Marcke |
| 5,783,290 A | 7/1998 | Isaac et al. |
| 5,786,598 A | 7/1998 | Clark et al. |
| 5,788,925 A | 8/1998 | Pai et al. |
| 5,788,940 A | 8/1998 | Cicha et al. |
| 5,798,165 A | 8/1998 | Mizoguchi et al. |
| 5,851,551 A | 12/1998 | Tseng et al. |
| 5,891,399 A | 4/1999 | Owesen |
| 5,901,564 A | 5/1999 | Comeau, II |
| 5,920,075 A | 7/1999 | Whitehead |
| 5,945,068 A | 8/1999 | Ferone |
| 5,945,910 A | 8/1999 | Gorra |
| 5,948,707 A | 9/1999 | Crawley et al. |
| 5,959,423 A | 9/1999 | Nakanishi et al. |
| 5,965,276 A | 10/1999 | Shlenker et al. |
| 6,010,727 A | 1/2000 | Rosenthal |
| 6,038,331 A * | 3/2000 | Johnson ............... 382/100 |
| 6,132,784 A | 10/2000 | Brandt et al. |
| 6,177,677 B1 | 1/2001 | Alboresi et al. |
| 6,192,887 B1 | 2/2001 | Howett et al. |
| 6,193,931 B1 | 2/2001 | Lin et al. |
| 6,223,137 B1 | 4/2001 | McCay et al. |
| 6,252,128 B1 | 6/2001 | Obata |
| 6,254,065 B1 * | 7/2001 | Ehrensperger et al. ......... 261/26 |
| 6,254,625 B1 | 7/2001 | Rosenthal et al. |
| 6,311,974 B1 | 11/2001 | Koga |
| 6,326,654 B1 | 12/2001 | Ruden et al. |
| 6,335,529 B1 | 1/2002 | Sekii et al. |
| 6,343,425 B1 | 2/2002 | Sias et al. |
| 6,370,694 B1 | 4/2002 | Michelson |
| 6,426,701 B1 | 7/2002 | Levy et al. |
| 6,429,438 B1 | 8/2002 | Smestad |
| 6,459,955 B1 | 10/2002 | Bartsch et al. |
| 6,485,979 B1 | 11/2002 | Kippenhan et al. |
| 6,490,351 B1 | 12/2002 | Roberts |
| 6,521,552 B1 | 2/2003 | Honna et al. |
| 6,524,698 B1 | 2/2003 | Schmoock |
| 6,530,498 B1 | 3/2003 | Ovadia |
| 6,560,782 B2 | 5/2003 | Hourihan et al. |
| 6,573,836 B1 | 6/2003 | Gitis et al. |
| 6,577,240 B2 | 6/2003 | Armstrong |
| 6,610,254 B1 | 8/2003 | Furner et al. |
| 6,656,424 B1 | 12/2003 | Deal |
| 6,663,805 B1 | 12/2003 | Ekiner et al. |
| 6,676,871 B1 | 1/2004 | Benassi et al. |
| 6,706,243 B1 | 3/2004 | Sias et al. |
| 6,716,352 B1 | 4/2004 | Livingston |
| 6,727,818 B1 | 4/2004 | Wildman et al. |
| 6,733,495 B1 | 5/2004 | Bek et al. |
| 6,755,536 B2 | 6/2004 | Tegreene et al. |
| 6,765,029 B2 | 7/2004 | Sasabe et al. |
| 6,806,361 B1 | 10/2004 | Kajisa et al. |
| 6,872,366 B2 | 3/2005 | Thomas et al. |
| 6,882,278 B2 | 4/2005 | Winings et al. |
| 6,901,712 B2 | 6/2005 | Lionel |
| 6,911,177 B2 | 6/2005 | Deal |
| 6,913,758 B2 | 7/2005 | Hourihan et al. |
| 6,925,679 B2 | 8/2005 | Wallach et al. |
| 6,937,221 B2 | 8/2005 | Lippert et al. |
| 6,949,222 B1 | 9/2005 | Möller et al. |
| 6,961,541 B2 | 11/2005 | Overy et al. |
| 6,963,289 B2 | 11/2005 | Aljadeff et al. |
| 6,968,194 B2 | 11/2005 | Aljadeff et al. |
| 6,991,761 B2 | 1/2006 | Hehenberger et al. |
| 7,009,185 B2 | 3/2006 | Chi et al. |

(56) References Cited

U.S. PATENT DOCUMENTS

| | | |
|---|---|---|
| 7,015,816 B2 | 3/2006 | Wildman et al. |
| 7,056,971 B2 | 6/2006 | Varma |
| 7,101,408 B2 | 9/2006 | Himeno et al. |
| 7,104,519 B2 | 9/2006 | O'Maley et al. |
| 7,122,150 B2 | 10/2006 | Gonzalez et al. |
| 7,149,531 B2 | 12/2006 | Misikangas |
| 7,175,807 B1 | 2/2007 | Jones |
| 7,196,662 B2 | 3/2007 | Misikangas et al. |
| 7,209,752 B2 | 4/2007 | Myllymäki et al. |
| 7,228,136 B2 | 6/2007 | Myllymäki et al. |
| 7,286,057 B2 | 10/2007 | Bolling |
| 7,295,115 B2 | 11/2007 | Aljadeff et al. |
| 7,299,059 B2 | 11/2007 | Misikangas et al. |
| 7,349,683 B2 | 3/2008 | Misikangas et al. |
| 7,403,108 B2 | 7/2008 | Aljadeff et al. |
| 7,408,470 B2 | 8/2008 | Wildman et al. |
| 7,482,936 B2 | 1/2009 | Bolling |
| 7,522,049 B2 | 4/2009 | Aljadeff et al. |
| 7,616,122 B2 | 11/2009 | Bolling |
| 7,616,124 B2 | 11/2009 | Paessel et al. |
| 7,729,707 B2 | 6/2010 | Aljadeff et al. |
| 7,904,097 B2 | 3/2011 | Misikangas |
| 7,936,275 B2 | 5/2011 | Bolling |
| 7,982,619 B2 | 7/2011 | Bolling |
| 8,020,733 B2 | 9/2011 | Snodgrass |
| 8,056,768 B2 | 11/2011 | Snodgrass |
| 8,208,939 B2 | 6/2012 | Aljadeff et al. |
| 2002/0011934 A1 | 1/2002 | Cacioli et al. |
| 2002/0085947 A1 | 7/2002 | Deal |
| 2002/0158814 A1 | 10/2002 | Bright et al. |
| 2002/0175182 A1 | 11/2002 | Matthews |
| 2002/0192340 A1 | 12/2002 | Swart et al. |
| 2003/0030562 A1 | 2/2003 | Lane et al. |
| 2003/0081293 A1 | 5/2003 | Wood, Jr. et al. |
| 2003/0093503 A1 | 5/2003 | Yamaki et al. |
| 2003/0145664 A1 | 8/2003 | Schwarz et al. |
| 2003/0164285 A1 | 9/2003 | Korenev |
| 2003/0170901 A1 | 9/2003 | Kippenhan et al. |
| 2003/0194344 A1 | 10/2003 | Brafford et al. |
| 2003/0235605 A1 | 12/2003 | Lelah et al. |
| 2004/0024290 A1 | 2/2004 | Root et al. |
| 2004/0052679 A1 | 3/2004 | Root et al. |
| 2004/0056201 A1 | 3/2004 | Fink et al. |
| 2004/0072577 A1 | 4/2004 | Myllymaki et al. |
| 2004/0090333 A1 | 5/2004 | Wildman et al. |
| 2004/0120844 A1* | 6/2004 | Tribelsky et al. .......... 422/2 |
| 2004/0139555 A1 | 7/2004 | Conrad et al. |
| 2004/0176108 A1 | 9/2004 | Misikangas |
| 2004/0203870 A1 | 10/2004 | Aljadeff et al. |
| 2004/0211444 A1 | 10/2004 | Taylor et al. |
| 2004/0244138 A1 | 12/2004 | Taylor et al. |
| 2005/0013729 A1 | 1/2005 | Brown-Skrobot et al. |
| 2005/0022844 A1 | 2/2005 | Field et al. |
| 2005/0069453 A1 | 3/2005 | Forng et al. |
| 2005/0128139 A1 | 6/2005 | Misikangas et al. |
| 2005/0131635 A1 | 6/2005 | Myllymaki et al. |
| 2005/0135965 A1 | 6/2005 | Williams et al. |
| 2005/0136944 A1 | 6/2005 | Misikangas et al. |
| 2005/0156711 A1 | 7/2005 | Aljadeff et al. |
| 2005/0181804 A1 | 8/2005 | Misikangas et al. |
| 2005/0186108 A1 | 8/2005 | Fields |
| 2005/0197139 A1 | 9/2005 | Misikangas et al. |
| 2005/0207381 A1 | 9/2005 | Aljadeff et al. |
| 2005/0214506 A1 | 9/2005 | Lee et al. |
| 2005/0236579 A1 | 10/2005 | Jenkins et al. |
| 2005/0249791 A1 | 11/2005 | Hobbs et al. |
| 2005/0267233 A1 | 12/2005 | Joshi |
| 2006/0071799 A1 | 4/2006 | Verdiramo |
| 2006/0216193 A1 | 9/2006 | Johnson et al. |
| 2006/0236496 A1 | 10/2006 | Oh et al. |
| 2006/0259195 A1 | 11/2006 | Eliuk et al. |
| 2006/0273915 A1 | 12/2006 | Snodgrass |
| 2007/0008149 A1 | 1/2007 | Bolling |
| 2007/0046460 A1 | 3/2007 | Aljadeff et al. |
| 2007/0103296 A1 | 5/2007 | Paessel et al. |
| 2007/0117568 A1 | 5/2007 | Misikangas et al. |
| 2007/0149215 A1 | 6/2007 | Misikangas |
| 2007/0231188 A1 | 10/2007 | Jung et al. |
| 2007/0231191 A1 | 10/2007 | Jung et al. |
| 2007/0231192 A1 | 10/2007 | Jung et al. |
| 2007/0231193 A1 | 10/2007 | Jung et al. |
| 2007/0231194 A1 | 10/2007 | Jung et al. |
| 2007/0237674 A1 | 10/2007 | Jung et al. |
| 2007/0254015 A1 | 11/2007 | Ishikawa et al. |
| 2008/0037512 A1 | 2/2008 | Aljadeff et al. |
| 2008/0085223 A1 | 4/2008 | Jung et al. |
| 2008/0184518 A1 | 8/2008 | Taylor et al. |
| 2008/0186231 A1 | 8/2008 | Aljadeff et al. |
| 2008/0283786 A1 | 11/2008 | Snodgrass |
| 2009/0166382 A1 | 7/2009 | Snodgrass |
| 2009/0208378 A1 | 8/2009 | Jung et al. |
| 2009/0232703 A1 | 9/2009 | Jung et al. |
| 2009/0266842 A1 | 10/2009 | Snodgrass |
| 2009/0273465 A1 | 11/2009 | Shamir et al. |
| 2010/0086447 A1 | 4/2010 | Jung et al. |
| 2010/0090837 A1 | 4/2010 | Jung et al. |
| 2010/0111775 A1 | 5/2010 | Hyde et al. |
| 2010/0117823 A1 | 5/2010 | Wholtjen |
| 2010/0123560 A1 | 5/2010 | Nix et al. |
| 2010/0262430 A1 | 10/2010 | Gips et al. |
| 2010/0297602 A1 | 11/2010 | Jones, Jr. |
| 2010/0308076 A1 | 12/2010 | Snodgrass |
| 2011/0018769 A1 | 1/2011 | Misikangas et al. |
| 2011/0050501 A1 | 3/2011 | Aljadeff |
| 2011/0063106 A1 | 3/2011 | Snodgrass |
| 2011/0163870 A1 | 7/2011 | Snodgrass |
| 2011/0195701 A1 | 8/2011 | Cook et al. |
| 2011/0227740 A1 | 9/2011 | Wohltjen |
| 2011/0291841 A1 | 12/2011 | Hollock et al. |

FOREIGN PATENT DOCUMENTS

| | | |
|---|---|---|
| EP | 1 537 796 A2 | 6/2005 |
| EP | 1 609 488 A1 | 12/2005 |
| EP | 2 180 334 A3 | 4/2010 |
| GB | 2291350 A | 1/1996 |
| JP | 01139139 A | 5/1989 |
| JP | 07289616 | 11/1995 |
| JP | 08071132 A | 3/1996 |
| JP | 08071133 A | 3/1996 |
| JP | 08215110 | 8/1996 |
| JP | 08-266595 | 10/1996 |
| JP | 2000220334 | 8/2000 |
| JP | 2001-25501 | 1/2001 |
| JP | 2002364055 | 12/2002 |
| JP | 2003250865 | 9/2003 |
| JP | 2004317512 A | 11/2004 |
| KR | 10-2004-0031733 | 3/2004 |
| WO | WO 95/17634 | 6/1995 |
| WO | WO 01/10476 A1 | 2/2001 |
| WO | WO 01/60419 A1 | 8/2001 |
| WO | WO 03/056951 A2 | 7/2003 |
| WO | WO 2004/032019 A2 | 4/2004 |
| WO | WO 2004/035095 A1 | 4/2004 |
| WO | WO 2004/080494 A1 | 9/2004 |
| WO | WO 2005/048041 A2 | 5/2005 |
| WO | WO 2005/077076 A2 | 8/2005 |
| WO | WO 2006/007729 A1 | 1/2006 |
| WO | WO 2006/026436 A2 | 3/2006 |
| WO | WO 2010/059678 A2 | 5/2010 |
| WO | WO 2011/033504 A1 | 3/2011 |
| WO | WO 2011/058228 A1 | 5/2011 |

OTHER PUBLICATIONS

State Intellectual Property Office of P.R.C.; Application No. 200780040949.2; Jul. 16, 2010; pp. 1-7.
U.S. Appl. No. 60/605,066, filed Aug. 27, 2004, Taylor, Charles E.
Advanced Sterilization Products; "Frequently Asked Questions"; pp. 1-3; located at http://www.sterrad.com/products_&_services/sterrad/sterrad_nx/faqs/index.asp; bearing a date of 2006; Advanced Sterilization Products; printed on Mar. 3, 2006.
Big Sky Laser; "Nd:YAG & Dye Laboratory Lasers from Quantel"; pp. 1-4; located at http://www.bigskylaser.com/lablasers.html#tdl190; printed on Mar. 22, 2006.

(56) References Cited

OTHER PUBLICATIONS

Big Sky Laser; "The Brilliant Series of Nd:YAG laser oscillators and accessories"; p. 1; located at http://www.bigskylaser.com/brilliantseries.html; printed on Mar. 22, 2006.
"CDC Urges Hospitals to Tackle Drug-Resistant Infections"; The Wall Street Journal; bearing a date of Oct. 19, 2006; pp. 1-2; printed on Oct. 31, 2006.
Creative Concepts; "Creative Oz-Air (i) Pvt. Ltd: Ozone Ambient Air Monitor & Controller, Hands Sterilizer, U.V. Systems, Ozone Test Kits, Ozone aCCESSORIES"; pp. 1-3; Creative Oz-Air (i) Pvt. Ltd.; located at http://www.creativeconceptsozair.com/ozoneambient.html#handstenlizer; printed on Apr. 25, 2006.
De Kock, Servaas; "Marketplace: Ozone Dry hand Sterilizing Unit"; pp. 1-2; located at http://www.ecademy.com/module.php?mod=list&lid=11053; bearing a date of Dec. 3, 2005; Ecademy; Cape Town, South Africa; printed on Apr. 25, 2006.
Elgan, Mike; "The Raw Feed Archives: Unexpected Convergence: Mouse and Hand Sterilizer"; pp. 1-6; located at http://www.mikeslist.com/2003_09_28_archive.html; bearing a of Oct. 4, 2003; Mike's List; printed on Apr. 25, 2006.
Enhance-It; "Mobile Room Sterilizers"; p. 1; located at http://www.enhance-it.com/06mobile.htm; bearing a date of 1999-2006; Enhance-It LLC; printed on Mar. 22, 2006.
Enhance-It, "Portable Germicidal Units"; p. 1; located at http://www.enhance-it.com/05portable.htm; bearing a date of 1999-2006, Enhance-It LLC; printed on Mar. 22, 2006.
Enhance-It, "Portable Germicidal Units"; p. 1; located at http://www.enhance-it.com/04portable.htm; bearing a date of 1999-2006, Enhance-It LLC; printed on Mar. 22, 2006.
Enhance-It, "Ultraviolet Light"; p. 1-2; located at http://www.enhance-it.com/uaprod.htm; bearing a date of 1999-2006, Enhance-It LLC; printed on Mar. 22, 2006.
European Search Report; European App. No. EP 07 75 4150; Sep. 14, 2009; pp. 1-6.
Globalspec; "About UV Light System"; pp. 1-3; located at http://light-sources.globalspec.com/LearnMore/Optics_Optical_Components/Light_Sources/Process_UV_Lamps_Systems; bearing a date of 1999-2006; Globalspec, Inc.; printed on Mar. 22, 2006.
Hilton, Paul; "Nd:YAG laser welding"; TWI World Centre for Materials Joining Technology; pp. 1-2; located at http://www.twi.co.uk/j32k/protected/band_3/kspah003.html; bearing a date of 2001; TWI Ltd; printed on Mar. 22, 2006.
HRS; "Specialty/Hygiene System—Hand Sterilizer" pp. 1-2; located at http://www.hrs.co.kr/english/hrs_speciality_hand.htm; bearing a date of 2004; HRS, Seoul, South Korea; printed on Apr. 25, 2006.
Marhoc; "Marhoc's Automatic Hand Sterilizer U.S. Patent #—6,872,366" pp. 1-3; located at http://www.marhoc.com/Marhoc_Hand_Sterilizer.htm; bearing a date of 2005; Marhoc, printed on Apr. 25, 2006.
Medical Device Link; "Equipment News: Packaging and Sterilization Equipment—Machine Designers Address Space, Validation Issues"; Medical Product Manufacturing News; pp. 1-5; located at http://www.devicelink.com/mpmn/archive/01/04/004.html; bearing a date of Apr. 2001; printed on Mar. 22, 2006.
Nehmzow, U.; "Mobile Robotics: A Practical Introduction," $2^{nd}$ Edition, 2003, ISBN No. 1852337265, Springer, London, UK (not provided).
Olgear; "Ozone Dry Hand Sterilising unit"; pp. 1-2; located at http://www.olgear.com/sites/58/images/ozone_hand_steriliser.pdf.

PCT International Search Report; International App. No. PCT/US 07/07846, Nov. 18, 2008, pp. 1-2.
PCT International Search Report; International App. No. PCT/US07/07673, Oct. 10, 2008, pp. 1-2.
PCT International Search Report; International App. No. PCT/US07/07845, Sep. 18, 2008, pp. 1-2.
PCT International Search Report; International App. No. PCT/US 07/23129; Apr. 10, 2008; pp. 1-2.
PCT International Search Report; International App. No. PCT/US 07/07582; Apr. 11, 2008; pp. 1-2.
Siegwart, Roland; Nourbakhsh, Illah R.; "Introduction to Autonomous Mobile Robots," 2004, ISBN No. 0-262-19502-X, The MIT Press, Cumberland, RI.
Smith, Ann; Heckelman, Patricia E.; O'Neil, Maryadele J. (Ed); Budavari, Susan (Ed); The Merck Index: An Encyclopedia of Chemicals, Drugs and Biologicals; bearing a date of Oct. 2001; 2564 pages; $13^{th}$ Edition; ISBN No. 0911910131; John Wiley and Sons and Merck & Co. Inc.; Whitehouse Station, NJ.
Smith, Michael; "ICAAC: Rhinovirus on Hands Blocked by Solution for Hours"; MedPage Today; Bearing dates of Oct. 2, 2006 and 2004-2006; pp. 1-2; San Francisco; MedPage Today, LLC; printed on Oct. 19, 2006.
Supplementary European Search Report; European App. No. 07774171.8; Sep. 14, 2009; 6 Total Pages.
Supplementary European Search Report; European App. No. 07754226.4; Sep. 14, 2009; 7 Total Pages.
Supplementary European Search Report; European App. No. 07754375.9; Sep. 14, 2009; 6 Total Pages.
Supplementary European Search Report; European App. No. 07754150.6; Sep. 14, 2009; 6 Total Pages.
Tidybio; "No-touch fully inductive control: Quick-speed and efficient sterilization: No need of water supply and quick-speed air-drying: Easy Operation without waste"; pp. 1-7; located at http://www.tidybio.cn/english/Sterilizer.shtml; bearing a date of 2003-2005; Beijing Tidybio Science & Technology Co., Ltd., printed on Apr. 25, 2006.
Wikipedia; "Nd:YAG laser"; pp. 1-2; located at http://en.wikipedia.org/wiki/Nd-YAG_laser; bearing a date of Feb. 23, 2006; printed on Mar. 22, 2006.
Xenon Corporation; "SteriPulse-XL-Sterilization and Decontamination Systems"; pp. 1-6; located at http://www.xenoncorp.com/sterilization.html; printed on Mar. 23, 2006.
Xie, Ming; "Fundamentals of Robotics. Linking Perception to Action," 2003, ISBN No. 9812383131, World Scientific Publishing Co. Pte. Ltd., River Edge, NJ.
Korean Intellectual Property Office; Notice of Preliminary Rejection; App. No. 10-2008-7026850; Jul. 10, 2013; 7 pages (and including machine translation consisting of 6 pages).
Korean Intellectual Property Office; Notice of Preliminary Rejection; App. No. 10-2008-7026821; Jun. 19, 2013; 3 pages (and including machine translation consisting of 3 pages).
Rospierski, Jeffrey; United States Design Patent; US D654,743 S; Feb. 28, 2012; 7 pages.
Korean Intellectual Property Office Notice of Preliminary Rejection; App. No. 10-2013-7033786; Jan. 24, 2014; 8 pages.
Korean Intellectual Property Office Notice of Allowance; App. No. 10-2008-7026821; Dec. 17, 2013; 11 pages.
Korean Intellectual Property Office Notice of Preliminary Rejection; App. No. 10-2013-7032032; Jan. 17, 2014; 11 pages.

* cited by examiner

SURVEYING STERILIZER METHODS AND SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/584,339, now patented, U.S. Pat. No. 7,754,156, entitled SURVEYING STERILIZER METHODS AND SYSTEMS, naming Roderick A. Hyde, Edward K.Y. Jung, Royce A. Levien, Robert W. Lord, Mark A. Malamud, John D. Rinaldo, Jr., Clarence T. Tegreene, and Lowell L. Wood, Jr. as inventors, filed 20 Oct. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/411,207, entitled SURVEYING STERILIZER METHODS AND SYSTEMS, naming Roderick A. Hyde, Edward K.Y. Jung, Royce A. Levien, Robert W. Lord, Mark A. Malamud, John D. Rinaldo, Jr., clarence T. Tegreene, and Lowell L. Wood, Jr. as inventors, filed 25 Apr. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/396,256 entitled STERILIZATION METHODS AND SYSTEMS, naming Edward K.Y. Jung, Royce A. Levien, Robert W. Lord, Mark A. Malamud, John D. Rinaldo, Jr., and Lowell L. Wood, Jr. as inventors, filed 31 Mar. 2006 now U.S. Pat. No. 8,277,724, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to sterilization methods and systems that may be used within numerous contexts, such as health-care and manufacturing facilities.

SUMMARY

In some embodiments, a sterilization method is provided that includes surveying one or more areas and transmitting one or more signals to one or more sterilization units in response to the surveying one or more areas. In addition to the foregoing, other method aspects are described in the claims, drawings, and/or text forming a part of the present application.

In some embodiments, a sterilization method is provided that includes receiving one or more signals associated with one or more survey units and applying one or more sterilization agents to one or more areas in response to the receiving one or more signals associated with one or more survey units. In addition to the foregoing, other method aspects are described in the claims, drawings, and/or text forming a part of the present application.

In some embodiments, a sterilization system is provided that includes circuitry for surveying one or more areas and circuitry for transmitting one or more signals to one or more sterilization units responsive to the circuitry for surveying one or more areas. In addition to the foregoing, other system aspects are described in the claims, drawings, and/or text forming a part of the present application.

In some embodiments, a sterilization system is provided that includes circuitry for receiving one or more signals associated with one or more survey units and circuitry for applying one or more sterilization agents to one or more areas in response to the circuitry for receiving one or more signals associated with one or more survey units. In addition to the foregoing, other system aspects are described in the claims, drawings, and/or text forming a part of the present application.

In some embodiments, a sterilization system is provided that includes means for surveying one or more areas and means for transmitting one or more signals to one or more sterilization units responsive to the means for surveying one or more areas. In addition to the foregoing, other system aspects are described in the claims, drawings, and/or text forming a part of the present application.

In some embodiments, a sterilization system is provided that includes means for receiving one or more signals from one or more survey units and means for applying one or more sterilization agents to one or more areas in response to the means for receiving one or more signals from one or more survey units. In addition to the foregoing, other system aspects are described in the claims, drawings, and/or text forming a part of the present application.

In some embodiments, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

DETAILED DESCRIPTION

Figure 1:
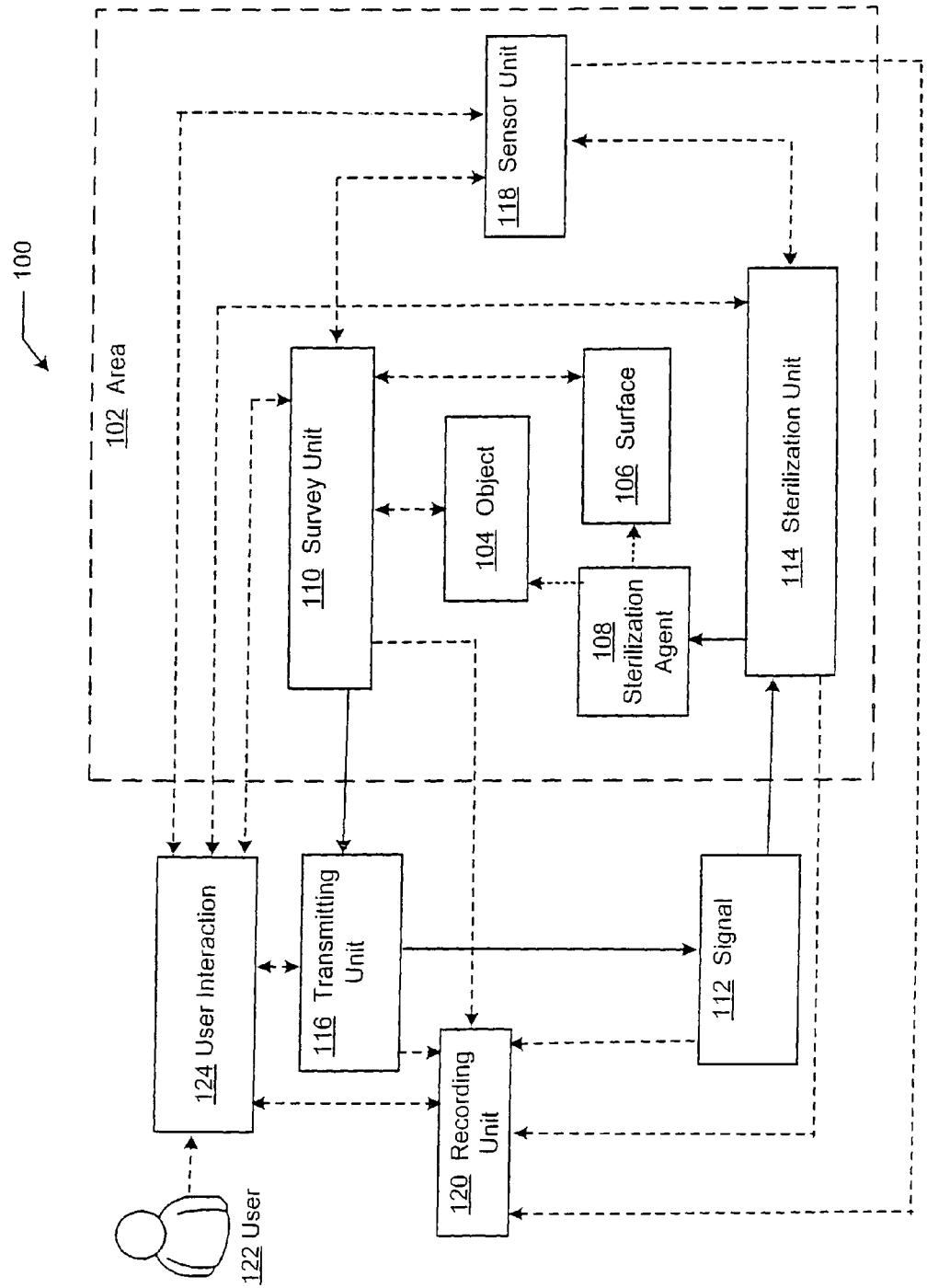
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a sterilization method that may be used to sterilize one or more areas 102, sterilize one or more objects 104 within one or more areas 102, sterilize one or more surfaces 106 within one or more areas 102 and/or substantially any combination thereof. In some embodiments, the system 100 is operable to provide a sterilization method that can be used to sterilize one or more areas 102, sterilize one or more objects 104 within one or more areas 102, sterilize one or more surfaces 106 within one or more areas 102, avoid sterilizing one or more areas 102, avoid sterilizing one or more objects 104 within one or more areas 102, avoid sterilizing one or more surfaces 106 within one or more areas 102 and/or substantially any combination thereof. In some embodiments, the system 100 is operable to sterilize one or more areas 102 without exposing one or more humans present within the one or more areas 102 to a sterilization agent 108. In some embodiments, the system 100 is operable to sterilize one or more areas 102, one or more surfaces 106 within one or more areas 102, and/or one or more objects 104 within one or more areas 102 without substantially exposing one or more humans present within the one or more areas 102 to a sterilization agent 108.

Survey Units

In some embodiments, the system 100 includes one or more survey units 110. In some embodiments, the one or more survey units 110 can be used to survey one or more areas 102. In some embodiments, one or more survey units 110 can detect the presence or absence of one or more objects 104 within one or more areas 102. In some embodiments, one or more survey units 110 can detect the presence and position of one or more objects 104 within one or more areas 102. In some embodiments, one or more survey units 110 can detect the presence of one or more surfaces 106 within one or more areas 102. In some embodiments, one or more survey units 110 can detect the presence or absence and position of one or more surfaces 106 within one or more areas 102. In some embodiments, one or more survey units 110 can detect the presence of one or more surfaces 106 and one or more objects 104 within one or more areas 102. In some embodiments, one or more survey units 110 can detect the presence or absence and position of one or more surfaces 106 and one or more objects 104 within one or more areas 102. In some embodiments, one or more sterilization units 114 receive one or more signals 112 that are associated with one or more survey units 110.

In some embodiments, one or more survey units 110 utilize one or more transmitting units 116 to transmit one or more signals 112 to one or more sterilization units 114. In some embodiments, one or more survey units 110 communicate with one or more sensor units 118. In some embodiments, one or more survey units communicate with one or more recording units 120. In some embodiments, one or more survey units 110 may provide for interaction with a user 122 through user interaction 124 with the one or more survey units 110. In some embodiments, one or more survey units 110 can detect one or more forms of radiation. In some embodiments, one or more survey units 110 can detect infrared radiation. In some embodiments, one or more survey units 110 can detect gamma radiation. In some embodiments, one or more survey units 110 can detect radiation that is in the form of light. In some embodiments, one or more survey units 110 can detect radiation that is in the form of ultraviolet light. In some embodiments, one or more survey units 110 can detect radiation, such as ultraviolet light, that has been reflected from one or more surfaces 106.

In some embodiments, one or more survey units 110 can determine an amount of radiation, such as ultraviolet light, to which one or more humans have been exposed within one or more areas 102. In some embodiments, one or more survey units 110 can determine an amount of radiation, such as ultraviolet light, to which one or more humans have been exposed through reflection of the radiation onto the one or more humans in one or more areas 102. Examples of such humans include, but are not limited to, hospital patients, dental patients, nurses, physicians, pharmaceutical workers, food workers, transportation workers, and the like. In some embodiments, one or more survey units 110 can determine an amount of light that is incident on one or more surfaces 106 that occur on one or more humans. Examples of such surfaces include, but are not limited to, open wounds, eyes, skin, and the like. In some embodiments, one or more survey units 110 can detect one or more times when one or more areas 102 have been sterilized. In some embodiments, one or more survey units 110 can detect how often one or more areas 102 are sterilized. In some embodiments, one or more survey units 110 can detect the intensity with which one or more areas 102 are sterilized. In some embodiments, one or more survey units 110 can detect whether or not one or more surfaces 106 within one or more areas 102 have been sterilized.

In some embodiments, one or more survey units 110 can detect one or more types of sterilization agents 108 that have been applied within one or more areas 102. In some embodiments, one or more survey units 110 can detect one or more types of sterilization agents 108 that have been applied to one or more surfaces 106 within one or more areas 102. In some embodiments, one or more survey units 110 can detect one or more types of sterilization agents 108 that have been applied to one or more objects 104 within one or more areas 102. In some embodiments, one or more survey units 110 can detect one or more types of sterilization agents 108 that have been applied to one or more objects 104 and/or one or more surfaces 106 within one or more areas 102.

In some embodiments, one or more survey units 110 can map one or more areas 102. In some embodiments, one or more survey units 110 can map one or more areas with one or more three dimensional laser scanners. Such three dimensional laser scanners are known and are commercially available (i.e., Callidus 3D laser scanner and GX scanner from Trimble Navigation Limited, Sunnyvale, Calif.; LMS-Z360i from Riegl USA Inc., Orlando, Fla.). In some embodiments, one or more survey units 110 can model one or more areas 102. In some embodiments, one or more survey units 110 can convert information received through mapping of one or more areas 102 and produce one or more models of the one or more areas 102. In some embodiments, the one or more models are three dimensional models.

In some embodiments, one or more sterilization units 114 receive one or more signals 112 from one or more survey units 110 that instruct the one or more sterilization units 114 where to apply one or more sterilization agents 108 within one or more areas based on one or more maps of the one or more areas 102. In some embodiments, one or more sterilization units 114 receive one or more signals 112 from one or more survey units 110 that instruct the one or more sterilization units 114 where to apply one or more sterilization agents 108 within one or more areas 102 based on one or more models of the one or more areas 102. In some embodiments, one or more sterilization units 114 receive one or more signals 112 from one or more survey units 110 that instruct the one or more sterilization units 114 where to apply one or more sterilization agents 108 within one or more areas based on one or more maps and/or one or more models of the one or more areas 102.

The one or more survey units 110 may utilize numerous technologies. For example, a survey unit 110 can use technologies that include, but are not limited to, infrared radiation, such as long-wave infrared radiation; retinal reflection; corneal reflection; tag readers, such as card readers, badge readers, bar code readers, and the like; motion detection; radar detection; sonar detection; gas chromatography; computer modeling; laser scanner; range finders, such as laser and infrared range finders; and/or substantially any combination thereof. Such technologies are known and are commercially available (i.e., Riegl USA Inc., Orlando, Fla.; Trimble Navigation Limited, Sunnyvale, Calif.).

In some embodiments, one or more survey units 110 that are stationary can be used within system 100. In some embodiments, one or more survey units 110 that are mobile can be used within system 100. In some embodiments, one or more survey units 110 that are stationary and one or more survey units 110 that are mobile can be used within system 100. In some embodiments, one or more survey units 110 that are stationary are positioned within one or more areas 102. In some embodiments, one or more survey units 110 that are stationary can be positioned within one or more areas 102 so that the one or more survey units 110 can survey substantially all surfaces 106 and/or substantially all objects 104 within the one or more areas 102. In some embodiments, survey units 110 that are mobile can move about one or more areas 102. In some embodiments, one or more survey units 110 that are mobile can move about one or more areas and survey substantially all surfaces 106 and/or substantially all objects 104 within the one or more areas 102. In some embodiments, one or more survey units 110 can move about one or more areas 102 according to a programmed set of instructions. In some embodiments, one or more survey units 110 can be programmed to move at a predetermined speed for a predetermined amount of time in a predetermined direction. In some embodiments, one or more survey units 110 can move about one or more areas 102 in a random manner. For example, in some embodiments, one or more survey units 110 can travel in one direction until they approach an object 104 or wall at which time the one or more survey units 110 can change direction and travel in a second direction until the one or more survey units 110 approach another object 104 or wall at which time the process will repeat. Accordingly, one or more survey units 110 can move about one or more areas 102 in a manner that avoids collision with objects 104 and/or walls. In some embodiments, one or more survey units 110 can travel in one direction until they contact an object 104 or wall at which time the one or more survey units 110 can change direction and travel in a second direction until the one or more survey units 110 contact another object 104 or wall at which time the process will repeat. Accordingly, one or more survey units 110 can move about one or more areas 102 in a manner that involves contact with objects 104 and/or walls. In some embodiments, one or more survey units 110 can move about one or more areas 102 on one or more guides, or combination of one or more guides, such as rails, tracks, guide wires or the like. For example, in some embodiments, one or more survey units 110 can be movably coupled to one or more guides that are operably coupled to one or more ceilings within one or more areas 102. In some embodiments, one or more survey units 110 can be movably coupled to one or more guides that are operably coupled to one or more walls within one or more areas 102. In some embodiments, one or more survey units 110 can be movably coupled to one or more guides that are operably coupled to one or more floors within one or more areas 102. In some embodiments, one or more survey units 110 can be movably coupled to one or more guides that are operably coupled to one or more walls, one or more ceilings, one or more floors, and/or substantially any combination of walls, ceilings, and floors within one or more areas 102. In some embodiments, one or more survey units 110 can respond to one or more signals 112 associated with one or more sensor units 118. In some embodiments, one or more survey units 110 can send one or more signals 112 instructing one or more sterilization units 110 to move to one or more areas 102 and apply one or more sterilization agents 108 within the one or more areas 102. In some embodiments, one or more survey units 110 can move to and/or within one or more areas 102 in response to one or more signals 112 associated with one or more sensor units 118. Methods to fabricate robots and robotic control systems that may be used to construct survey units 110 are known and have been described (i.e., Xie, Fundamentals of Robotics: Linking Perception to Action, World Scientific Publishing Co. Pte. Ltd., River Edge, N.J., 2003; Nehmzow, Mobile Robotics: A Practical Introduction, $2^{nd}$ Edition, Springer-Verlag, London, UK, 2003; Siegwart and Nourbakhsh, Introduction to Autonomous Mobile Robots, The MIT Press, Cumberland, R.I., 2004).

Areas

The system 100 includes one or more areas 102. The system 100 may be used within numerous areas 102. Examples of such areas include, but are not limited to, hospitals, such as operating rooms and wards; transportation, such as airplanes, trains, automobiles, subways, ships, spacecraft and buses; restrooms; pharmaceutical manufacturing facilities; food preparation facilities; food packaging facilities; medical device manufacturing facilities; hotels; and the like. In some embodiments, one or more areas 102 can include portions of one or more areas 102.

OBJECTS

The system 100 may include the presence or absence of one or more objects 104 within one or more areas 102. Numerous types of objects 104 may be present or absent within one or more areas 102. Examples of such objects 104 include, but are not limited to, humans, non-human animals, plants, medical instruments, cooking utensils, stoves, ovens, food storage devices, pharmaceutical formulation devices, food packaging devices, food preparation devices, eating utensils, sinks, tables, machinery, waste areas, seats, surgical tables, hospital examination tables, dental instruments, dental chairs, and the like.

Surfaces

The system 100 may include one or more surfaces 106 within one or more areas 102. In some embodiments, one or more surfaces 106 may be positioned within one or more areas 102 on building materials used to construct the one or more areas 102. For example, one or more surfaces 106 may occur on a floor, wall and/or ceiling that are part of one or more areas 102. In some embodiments, one or more surfaces 106 are positioned on one or more objects 104 included within one or more areas 102. For example, one or more surfaces 106 within one or more areas 102 may be positioned on one or more humans, non-human animals, plants, medical instruments, cooking utensils, stoves, ovens, food storage devices, pharmaceutical formulation devices, food packaging devices, food preparation devices, eating utensils, sinks, tables, machinery, waste areas, seats, surgical tables, hospital examination tables, dental instruments, dental chairs, and the like. One or more surfaces 106 can be made of numerous types of material. Examples of types of materials that can form such surfaces 106 include, but are not limited to, ceramics, porcelain, plastic, nylon, paint, concrete, paneling, fabric, rubber, metal, wood, rock, paper, and the like. One or more surfaces 106 within one or more areas 102 can have numerous types of shapes. For example, one or more surfaces 106 can include pores, pits, scratches, cracks, depressions, bumps, troughs, mesh, holes, and the like. In some embodiments, a sterilization agent 108 may be selected based on the shape and type of material from which a surface 106 is made. For example, in some embodiments, a sterilization agent 108 that can penetrate into pores included within a surface may be used to sterilize a surface 106 having pores. In some embodiments, one or more sterilization agents 108 may be selected to sterilize one or more surfaces 106 that do not damage the one or more surfaces 106.

Sterilization Agents

The system 100 may include one or more sterilization agents 108. Numerous types of sterilization agents 108 may be used within system 100. Examples of such sterilization agents 108 include, but are not limited to, ultraviolet light, gamma radiation, sonic radiation, chemicals, infrared radiation, steam, gases, and the like. Numerous types of sterilization agents 108 are known and are commercially available. In some embodiments, the identity of one or more sterilization agents 108 can be specified according to the identity and/or characteristics of a surface 106 or object 104 to be sterilized. For example, in some embodiments, a sterilization agent 108 that is a gas may be applied to a surface 106 or object 104 that is porous and unable to be sterilized with ultraviolet light. In other embodiments, ultraviolet light may be used as a sterilization agent 108 to sterilize a surface 106 or object 104 that is smooth. Accordingly, one or more sterilization units 114 may apply one or more sterilization agents 108 in accordance with the characteristics of a surface 106 or object 104 to be sterilized. In some embodiments, one or more sterilization agents 108 can be selected based on the type of contaminant that is to be killed, inactivated and/or detoxified through use of one or more sterilization agents 108. Examples of such contaminants can include, but are not limited to, bacteria, fungus, viruses, spores, microbes, eggs, and the like. The quantity and amount of time that one or more sterilization agents 108 are to be applied to one or more areas 102 or one or more surfaces 106 to kill, inactivate, and/or detoxify one or more contaminants can be readily determined though use of standard protocols. Example irradiation parameters for ultraviolet light are provided in Table I for numerous types of contamination.

TABLE I

Sample Parameters for Sterilization with Ultraviolet Purifiers

| Bacteria | Energy in mW-sec/cm$^2$ Sterilization up to 90% | Energy in mW-sec/cm$^2$ Sterilization up to 99% |
|---|---|---|
| *Bacillus anthracis* | 4.52 | 9.04 |
| *S. enteritidis* | 4.00 | 8.00 |
| *B. megatherium* sp. (vegetative) | 1.30 | 2.60 |
| *B. megatherium* sp. (spores) | 2.73 | 5.46 |
| *B. paratyphosus* | 3.20 | 6.40 |
| *B. subtilis* | 7.10 | 14.20 |
| *B. subtilis* spores | 12.00 | 24.00 |
| *Corynebacterium diphtheriae* | 3.37 | 6.74 |
| *Eberthella typhosa* | 2.14 | 4.28 |
| *Escherichia coli* | 3.00 | 6.00 |
| *Micrococcus candidus* | 6.05 | 12.10 |
| *Micrococcus sphaeroides* | 10.00 | 20.00 |
| *Neisseria catarrhalis* | 4.40 | 8.80 |
| *Phytomonas tumefaciens.* | 4.40 | 8.80 |
| *Proteus vulgaris* | 2.64 | 5.28 |
| *Pseudomonas aeruginosa* | 5.50 | 11.00 |
| *Pseudomonas fluorescens* | 3.50 | 7.00 |
| *S. typhimurium* | 8.00 | 16.00 |
| *Sarcina Lutea* | 19.70 | 39.40 |
| *Seratia marcescens* | 2.42 | 4.84 |
| *Dysentery bacilli* | 2.20 | 4.40 |
| *Shigella paradysenteriae* | 1.68 | 3.36 |
| *Spirillum rubrum* | 4.40 | 8.80 |
| *Staphylococcus albus* | 1.84 | 3.68 |
| *Staphylococcus aureus* | 2.60 | 5.20 |
| *Streptococcus hemolyticus* | 2.16 | 4.32 |
| *Streptococcus lactis* | 6.15 | 12.30 |
| *Streptococcus viridans* | 2.00 | 4.00 |

Signals

The system 100 includes one or more signals 112. In some embodiments, one or more signals 112 are transmitted to one or more sterilization units 114. The one or more signals 112 can include numerous types of information. In some embodiments, one or more signals 112 can include one or more instructions for one or more sterilization units 114 to apply one or more sterilization agents 108 to one or more areas 102. In some embodiments, one or more signals 112 can include one or more instructions for one or more sterilization units 114 to avoid applying one or more sterilization agents 108 to one or more areas 102. In some embodiments, one or more signals 112 can include one or more instructions for one or more sterilization units 114 to apply one or more sterilization agents 108 to one or more surfaces 106 within one or more areas 102. In some embodiments, one or more signals 112 can include one or more instructions for one or more sterilization units 114 to avoid applying one or more sterilization agents 108 to one or more surfaces 106 within one or more areas 102. In some embodiments, one or more signals 112 can include one or more instructions for one or more sterilization units 114 to apply one or more sterilization agents 108 to one or more objects 104 within one or more areas 102. In some embodiments, one or more signals 112 can include one or more instructions for one or more sterilization units 114 to avoid applying one or more sterilization agents 108 to one or more objects 104 within one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more areas 102 for sterilization. In some embodiments, one or more signals 112 are associated with prioritizing one or more surfaces 106 within one or more areas 102 for sterilization. In some embodiments, one or more signals 112 are associated with one or more humans that are present or absent within one or more areas 102. In some embodiments, one or more signals 112 are associated with one or more instructions indicating one or more portions of one or more areas 102 where one or more sterilization units 114 are to apply one or more sterilization agents 108. In some embodiments, one or more signals 112 are associated with one or more instructions indicating one or more portions of one or more areas 102 where one or more sterilization units 114 are not to apply one or more sterilization agents 108. In some embodiments, one or more signals 112 are associated with one or more instructions for one or more sterilization units 114 to apply one or more sterilization agents 108 that are identified to one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

Sterilization Units

The system 100 can include one or more sterilization units 114. In some embodiments, one or more sterilization units 114 that are stationary can be used within system 100. In some embodiments, one or more sterilization units 114 that are mobile can be used within system 100. In some embodiments, one or more sterilization units 114 that are stationary and one or more sterilization units 114 that are mobile can be used within system 100. In some embodiments, one or more sterilization units 114 that are stationary are positioned within one or more areas 102. In some embodiments, one or more sterilization units 114 that are stationary can be positioned within one or more areas 102 so that the one or more sterilization units 114 can apply one or more sterilization agents 108 to substantially all surfaces 106 and/or substantially all objects 104 within the one or more areas 102. In some embodiments, sterilization units 114 that are mobile can move about one or more areas 102. In some embodiments, one or more sterilization units 114 that are mobile can move about one or more areas and apply one or more sterilization agents 108 to substantially all surfaces 106 and/or substantially all objects 104 within the one or more areas 102. In some embodiments, one or more sterilization units 114 can move about one or more areas 102 according to a programmed set of instructions. In some embodiments, one or more sterilization units 114 can be programmed to move at a predetermined speed for a predetermined amount of time in a predetermined direction. In some embodiments, one or more sterilization units 114 can move about one or more areas 102 in a random manner. For example, in some embodiments, one or more sterilization units 114 can travel in one direction until they approach an object 104 or wall at which time the one or more sterilization units 114 can change direction and travel in a second direction until the one or more sterilization units 114 approach another object 104 or wall at which time the process will repeat. Accordingly, one or more sterilization units 114 can move about one or more areas 102 in a manner that avoids collision with objects 104 and/or walls. In some embodiments, one or more sterilization units 114 can travel in one direction until they contact an object 104 or wall at which time the one or more sterilization units 114 can change direction and travel in a second direction until the one or more sterilization units 114 contact another object 104 or wall at which time the process will repeat. Accordingly, one or more sterilization units 114 can move about one or more areas 102 in a manner that involves contact with one or more objects 104 and/or one or more walls. In some embodiments, one or more sterilization units 114 can move about one or more areas 102 on one or more guides, or combination of one or more guides, such as rails, tracks, guide wires or the like. For example, in some embodiments, one or more sterilization units 114 can be movably coupled to one or more guides that are operably coupled to one or more ceilings within one or more areas 102. In some embodiments, one or more sterilization units 114 can be movably coupled to one or more guides that are operably coupled to one or more walls within one or more areas 102. In some embodiments, one or more sterilization units 114 can be movably coupled to one or more guides that are operably coupled to one or more floors within one or more areas 102. In some embodiments, one or more sterilization units 114 can be movably coupled to one or more guides that are operably coupled to one or more walls, one or more ceilings, one or more floors, and/or substantially any combination of walls, ceilings, and floors within one or more areas 102. In some embodiments, one or more sterilization units 114 can respond to one or more signals 112 associated with one or more survey units 110 that instruct the one or more sterilization units 114 where to move within one or more areas 102. In some embodiments, one or more survey units 110 can send one or more signals 112 instructing one or more sterilization units 114 to move to one or more areas 102 and apply one or more sterilization agents 108 within the one or more areas 102. In some embodiments, one or more sterilization units 114 can move to and/or within one or more areas 102 in response to one or more signals 112 associated with one or more survey units 110. In some embodiments, the one or more sterilization units 114 may then apply one or more sterilization agents 108 to one or more surfaces 106 and/or one or more objects 104 within the one or more areas 102. Methods to fabricate robots and robotic control systems that may be used to construct sterilization units 114 are known in and have been described (i.e., Xie, Fundamentals of Robotics: Linking Perception to Action, World Scientific Publishing Co. Pte. Ltd., River Edge, N.J., 2003; Nehmzow, Mobile Robotics: A Practical Introduction, $2^{nd}$ Edition, Springer-Verlag, London, UK, 2003; Siegwart and Nourbakhsh, Introduction to Autonomous Mobile Robots, The MIT Press, Cumberland, R.I., 2004).

In some embodiments, one or more sterilization units 114 may emit radiation. In some embodiments, one or more sterilization units 114 may emit sterilizing radiation. Sterilizing radiation may be emitted from numerous types of sources that include, but are not limited to, emission from a cobalt-60 source, coherent light emitted from one or more frequency quadrupled-NdYAG/glass lasers (neodymium-doped yttrium aluminum garnet ($Nd:Y_3Al_5O_{12}$), excimer lasers, frequency quadrupled diode pumped solid state (DPSS) lasers, incoherent light emitted from one or more low-pressure mercury resonance lamps, emission from tunable dye lasers, and the like. Sources of sterilizing radiation are known in the art and are commercially available (XENON Corporation, Wilmington, Mass.; Big Sky Laser Technologies, Inc., Bozeman, Mont.; Enhance-It, LLC, Hilton Head Island, S.C. 29926; Advanced Sterilization Products, Irvine, Calif. 92618; Coherent Inc., Santa Clara, Calif. 95054).

In some embodiments, one or more sterilization units 114 can emit sterilizing radiation substantially constantly. In some embodiments, one or more sterilization units 114 can emit sterilizing radiation as a pulse. In some embodiments, one or more sterilization units 114 can emit numerous types and/or combinations of sterilizing radiation, such as ultraviolet light and/or gamma radiation. In some embodiments, one or more sterilization units 114 can emit ultraviolet light having wavelengths between 100 nanometers and 400 nanometers and/or substantially any combination of wavelengths between 100 nanometers and 400 nanometers. In other embodiments, one or more sterilization units 114 can emit ultraviolet light having wavelengths between 180 nanometers and 300 nanometers and/or substantially any combination of wavelengths between 180 nanometers and 300 nanometers. In some embodiments, one or more sterilization units 114 can emit ultraviolet light having wavelengths between 255 nanometers and 280 nanometers and/or substantially any combination of wavelengths between 255 nanometers and 280 nanometers. In some embodiments, one or more sterilization units 114 can emit ultraviolet light having wavelengths between 250 nanometers and 280 nanometers and/or substantially any combination of wavelengths between 250 nanometers and 280 nanometers. In other embodiments, one or more sterilization units 114 can emit ultraviolet light having wavelengths that are centered, but asymmetric, and about 265 nanometers and/or substantially any combination of wavelengths of such light. In some embodiments, one or more sterilization units 114 can exclude the emission of one or more wavelengths of radiation.

In some embodiments, one or more sterilization units 114 can emit sterilizing radiation according to parameters set at the one or more sterilization units 114. In some embodiments, one or more sterilization units 114 can emit sterilizing radiation according to instructions included within one or more signals 112 received by the one or more sterilization units 114. In some embodiments, one or more sterilization units 114 can emit sterilizing radiation according to parameters set at the one or more sterilization units 114 and according to instructions included within one or more signals 112 received by the one or more sterilization units 114. In some embodiments, emission of sterilizing radiation from one or more sterilization units 114 can be started and stopped, intensity modulated, paused, initiated, interrupted, resumed, steered, shaped, programmed to follow a preprogrammed schedule, routine or sequence, or substantially any combination thereof.

In some embodiments, one or more sterilization units 114 can emit one or more forms of non-sterilizing radiation. Examples of such non-sterilizing radiation include infrared radiation, sonic radiation, ultrasonic radiation, and the like.

In some embodiments, one or more sterilization units 114 can steer radiation emitted from the one or more sterilization units 114. In some embodiments, one or more sterilization units 114 can shape radiation emitted from the one or more sterilization units 114. In some embodiments, one or more sterilization units 114 can steer and shape radiation emitted from the one or more sterilization units 114. Methods and systems that can be used to steer and/or and shape emitted radiation, such as ultraviolet light, are known (i.e., U.S. Patent Application Number 20030081293: Optical communications system and method; U.S. Patent Application Number 20020158814: Electronically scanned beam display; U.S. Pat. No. 6,755,536: System and method for displaying/projecting a color image; U.S. Pat. No. 6,937,221: Scanned beam display; U.S. Pat. No. 5,557,444: Miniature optical scanner for a two axis scanning system; all of which are incorporated herein by reference). Briefly, in some embodiments, one or more sterilization units 114 may include a moving mirror that is mounted to a spring plate. The mirror may be mounted with a ferromagnetic material that is driven by a pair of electromagnetic coils to provide motive force to the mirror. Drive electronics can provide an electrical signal to activate the coils and thereby move the mirror. Alternatively, a mirror may be mounted to a pivoting shaft and driven by an inductive coil. In operation, one or more sterilization units 114 may emit radiation that strikes a mirror and is deflected from the mirror into one or more areas 102. The path of the deflected radiation may be controlled through activation of drive electronics that activate the coils and thereby move the mirror. Numerous other methods and systems may be used to steer and shape radiation, such as radiation emitted from one or more sterilization units 114.

Transmitting Units

The system 100 can include one or more transmitting units 116. In some embodiments, the one or more transmitting units 116 can transmit one or more signals 112 to one or more sterilization units 114. In some embodiments, the one or more transmitting units 116 can transmit one or more signals 112 to one or more sterilization units 114 in response to one or more survey units 110. The one or more transmitting units 116 can transmit numerous types of signals 112 to one or more sterilization units 114. For example, the one or more transmitting units 116 can transmit a signal 112 that includes, but is not limited to, a hardwired signal, an infrared signal, an optical signal, a radiofrequency (RF) signal, a digital signal, an analog signal, or substantially any combination thereof to one or more sterilization units 114. In some embodiments, one or more transmitting units 116 provide for user interaction 124 with a user 122. In some embodiments, one or more transmitting units 116 can communicate with one or more recording devices 120.

Sensor Units

The system 100 can include one or more sensor units 118. In some embodiments, one or more sensor units 118 can communicate with one or more sterilization units 114, one or more survey units 110, one or more recording units 120, and substantially any combination thereof. In some embodiments, one or more sensor units 118 provide for user interaction 124 with one or more users 122. In some embodiments, one or more sensor units 118 can detect one or more times when one or more areas 102 were sterilized. In some embodiments, one or more sensor units 118 can detect how often one or more areas 102 are sterilized. In some embodiments, one or more sensor units 118 can detect the intensity with which one or more areas 102 are sterilized. In some embodiments, one or more sensor units 118 can detect whether or not one or more surfaces 106 within one or more areas 102 have been sterilized. In some embodiments, one or more sensor units 118 can detect one or more types of sterilization agents 108 that have been applied within one or more areas 102. In some embodiments, one or more sensor units 118 can detect one or more types of sterilization agents 108 that have been applied to one or more surfaces 106 within one or more areas 102. In some embodiments, one or more sensor units 118 can detect one or more types of sterilization agents 108 that have been applied to one or more objects 104 within one or more areas 102. In some embodiments, one or more sensor units 118 can detect one or more types of sterilization agents 108 that have been applied to one or more objects 104 or one or more surfaces 106 within one or more areas 102. Sensor units 118 can utilize numerous types of technologies. In some embodiments, one or more sensor units 118 can determine when one or more areas 102 were exposed to ultraviolet light by detecting phosphorescent light emission from phosphorescent material that is included within the one or more areas 102. In some embodiments, one or more sensor units 118 can be used to detect phosphorescent light emission from one or more types of phosphorescent paint that is included within one or more areas 102. In some embodiments, one or more types of phosphorescent paint are included within one or more areas 102 that become excited upon being exposed to ultraviolet light used to sterilize the one or more areas 102. In some embodiments, the intensity of light emitted from one or more phosphorescent materials that are included within one or more areas 102 can be detected by one or more sensor units 118 to determine when the one or more areas 102 were irradiated with ultraviolet light. In some embodiments, one or more sensor units 118 may determine the rate at which emission from one or more phosphorescent materials that are included within one or more areas 102 decreases following irradiation with ultraviolet light to determine when the one or more areas 102 were irradiated with ultraviolet light. In some embodiments, two or more phosphorescent materials that emit light of different wavelengths are included within one or more areas 102. In some embodiments, two or more phosphorescent materials that emit light for different lengths of time following irradiation with ultraviolet light are included within one or more areas 102. In some embodiments, two or more phosphorescent materials that emit light of different wavelengths and that emit light for different lengths of time following irradiation with ultraviolet light are included within one or more areas 102. Accordingly, in some embodiments, one or more sensor units 118 can determine when one or more areas 102 were irradiated with ultraviolet light by detecting wavelengths and intensities of light emitted from one or more phosphorescent materials that are included within the one or more areas 102. In some embodiments, phosphorescent materials may be used to indicate when one or more areas 102 were sterilized with a heat-based sterilization agent 108, such as steam, due to the temperature dependence of phosphorescent emission. Phosphorescent materials and paints are known in the art and are commercially available (i.e., Risk Reactor, Huntington Beach, Calif.). In some embodiments, one or more sensor units 118 may include an ultraviolet light detector. Such detectors are known in the art and are commercially available (i.e., U.S. Pat. Nos. 6,429,438; 7,009,185: Ultraviolet detector and manufacture method thereof; U.S. Pat. No. 6,335,529: Ultraviolet detector; U.S. Pat. No. 6,326,654: Hybrid ultraviolet detector; U.S. Pat. No. 4,403,826: Ultraviolet radiation detector; all of which are incorporated herein by reference; Ofil Ltd., Nes-Ziona, Israel).

Recording Units

The system 100 may include one or more recording units 120. In some embodiments, one or more recording units 120 communicate with one or more sensor units 118, one or more sterilization units 114, one or more survey units 110, one or more transmitting units 116 and/or substantially any combination thereof. In some embodiments, one or more recording units 120 provide for user interaction 124 by one or more users 122. In some embodiments, one or more recording units 120 can receive one or more signals 112. The one or more recording units 120 can record numerous types of information. In some embodiments, one or more recording units 120 record information associated with one or more sterilization protocols assigned to one or more areas 102. In some embodiments, one or more recording units 120 record one or more times when one or more areas 102 were sterilized. In some embodiments, one or more recording units 120 record the identity of one or more sterilization agents 108 that were applied to one or more areas 102. In some embodiments, one or more recording units 120 record the intensity with which one or more areas 102 were sterilized. In some embodiments, one or more recording units 120 record one or more times when one or more areas 102 were sterilized. In some embodiments, one or more recording units 120 record the frequency with which one or more areas 102 are sterilized. Many types of recording devices 120 may be used. Examples of such recording devices include, but are not limited to, many types of memory, optical disks, magnetic disks, magnetic tape, and the like.

User Interaction

The system 100 may provide for user interaction 124. In some embodiments, a user 122 may interact with one or more transmitting units 116, one or more recording units 120, one or more survey units 110, one or more sensor units 118, one or more sterilization units 114 and/or substantially any combination thereof. Such interaction can include, but is not limited to, inputting instructions related to the sterilization of one or more areas with regard to time, place, duration, intensity, priority, identity of one or more sterilization agents and/or substantially any combination thereof. The user 122 can interact through use of numerous technologies. For example, user interaction 124 can occur through use of hardwired methods, such as through use of a keyboard, use of wireless methods, use of the internet, and the like. In some embodiments, a user 122 is not human.

In some embodiments, the sterilization method involves completely sterilizing one or more areas 102, partially sterilizing one or more areas 102, sterilizing one or more objects 104 within one or more areas 102, sterilizing one or more surfaces 106 within one or more areas 102, or substantially any combination thereof. In other embodiments, the method includes avoiding sterilization of one or more areas 102, avoiding sterilization of one or more surfaces 106 within one or more areas 102, avoiding sterilization of one or more objects 104 within one or more areas 102, or substantially any combination thereof. In still other embodiments, the method includes partially sterilizing one or more areas 102, sterilizing one or more surfaces 106 within one or more areas 102, sterilizing one or more objects 104 within one or more areas 102, avoiding sterilization of one or more areas 102, avoiding sterilization of one or more surfaces 106 within one or more areas 102, avoiding sterilization of one or more objects 104 within one or more areas 102, or substantially any combination thereof.

Figure 2:
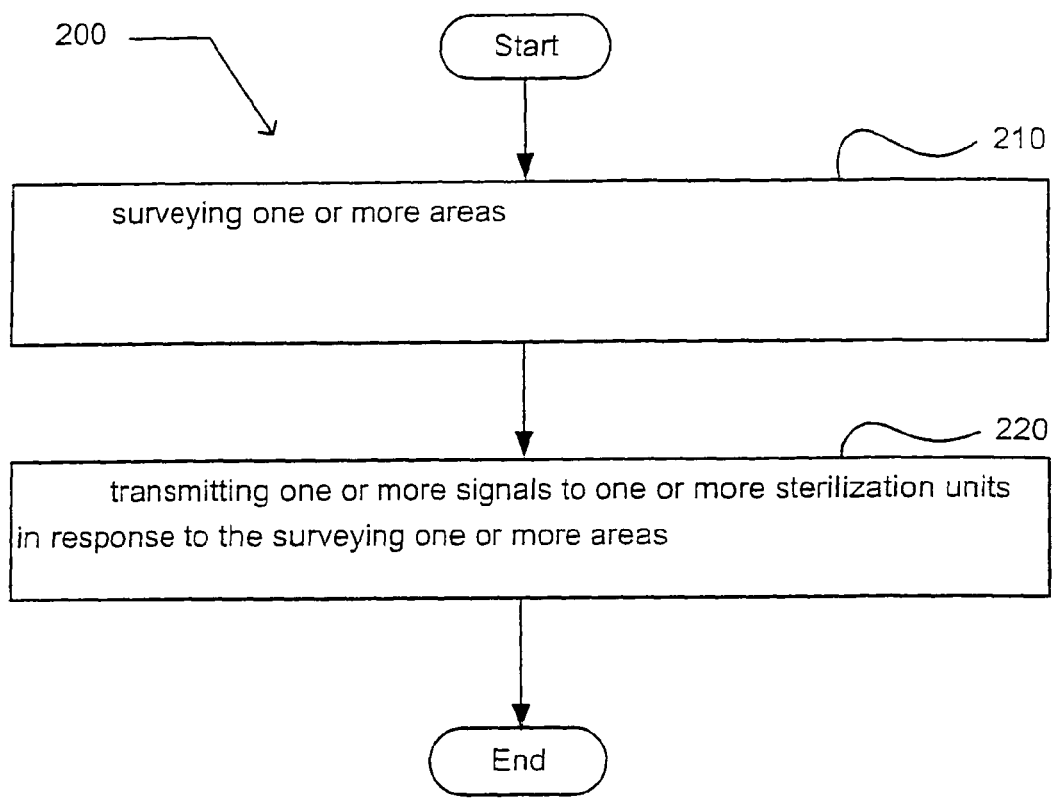
FIG. 2 illustrates an operational flow representing example operations related to sterilization methods.

FIG. 2 illustrates an operational flow 200 representing examples of operations that are related to the performance of a sterilization method. In FIG. 2 and in following figures that include various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes an operation 210 involving surveying one or more areas 102. In some embodiments, one or more survey units 110 are used to survey one or more areas 102. In some embodiments, one survey unit 110 is used to survey one area 102. In some embodiments, one survey unit 110 is used to survey one or more areas 102. In some embodiments, more than one survey unit 110 is used to survey one area 102.

The operational flow 200 also includes a transmitting operation 220 involving transmitting one or more signals to one or more sterilization units in response to the surveying one or more areas 102. In some embodiments, one or more transmitting units 116 transmit one or more signals 112 to one or more sterilization units 114. In some embodiments, one transmitting unit 116 transmits one signal 112 to one sterilization unit 114. In some embodiments, one transmitting unit 116 transmits one or more signals 112 to one sterilization unit 114. In some embodiments, one transmitting unit 116 transmits one signal 112 to one or more sterilization units 114. In some embodiments, one transmitting unit 116 transmits one or more signals 112 to one sterilization unit 114. In some embodiments, one transmitting unit 116 transmits one or more signals 112 to one or more sterilization units 114. In some embodiments, one or more transmitting units 116 transmit one signal 112 to one sterilization unit 114. In some embodiments, one or more transmitting units 116 transmit one or more signals 112 to one sterilization unit 114. In some embodiments, one or more transmitting units 116 transmit one signal 112 to one or more sterilization units 114.

Figure 3:
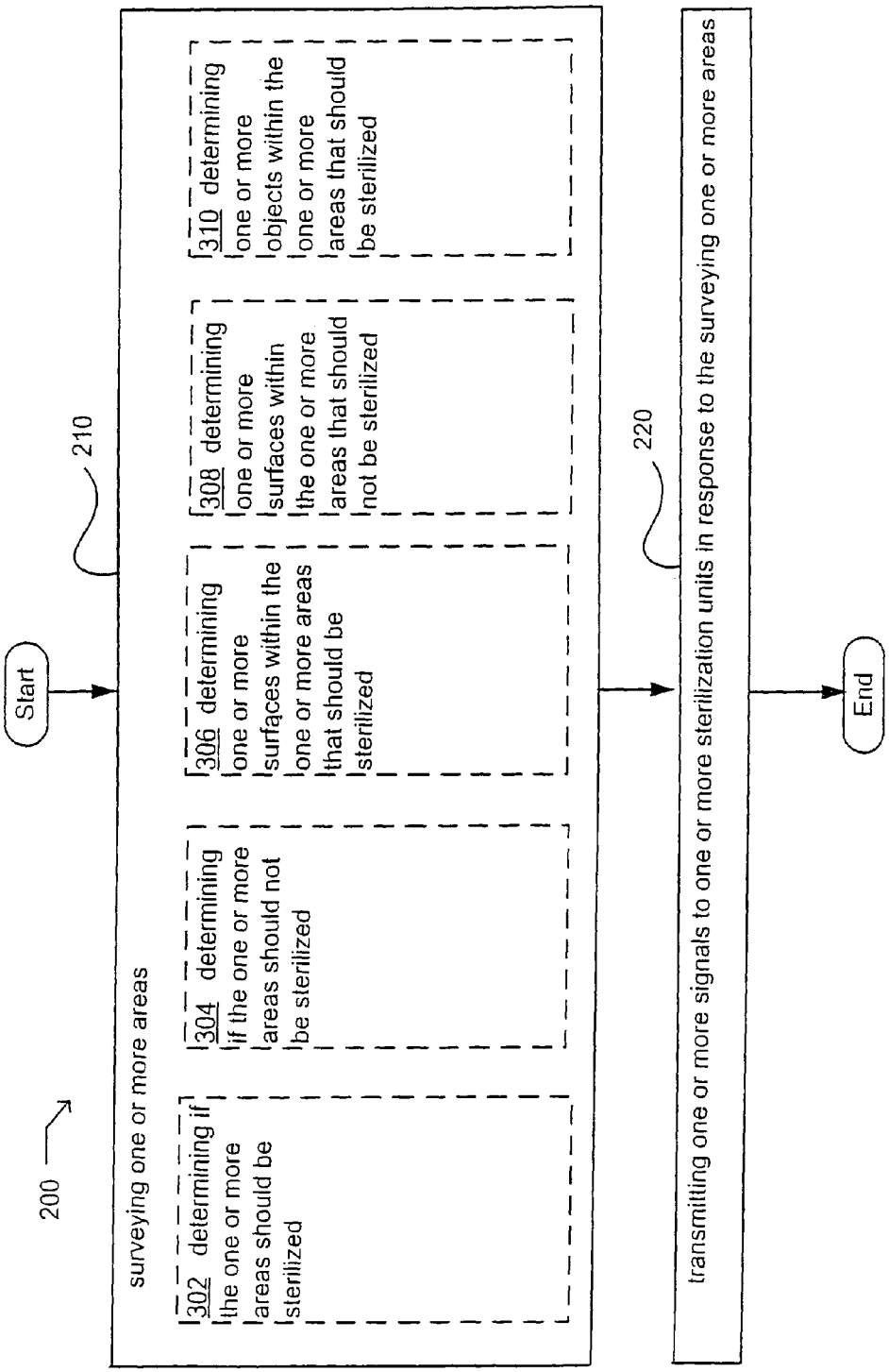
FIG. 3 illustrates an alternative embodiment of the example operation flow of FIG. 2.

FIG. 3 illustrates alternative embodiments of the example operational flow 200 of FIG. 2. FIG. 3 illustrates example embodiments where the surveying operation 210 may include at least one additional operation. Additional operations may include an operation 302, operation 304, operation 306, operation 308 and/or operation 310.

At operation 302, the surveying operation 210 may include determining if one or more areas 102 should be sterilized. In some embodiments, one or more survey units 110 can survey one or more areas 102 to determine if the one or more areas 102 should be sterilized. In some embodiments, one or more survey units 110 can determine if a predetermined amount of time has passed since one or more areas 102 were last sterilized. Accordingly, one or more areas 102 can be sterilized if more than a given amount of time has passed since the one or more areas 102 were last sterilized. In some embodiments, in order to determine when one or more areas 102 were last sterilized, one or more survey units 110 can communicate with one or more sensor units 118 that can communicate when the one or more areas 102 were last sterilized. In other embodiments, one or more survey units 110 can detect phosphorescent emission from one or more phosphorescent materials included within one or more areas 102 to determine when the one or more areas 102 were last sterilized. In some embodiments, one or more survey units 110 can detect the presence, absence and/or concentration of one or more sterilization agents 108 within one or more areas 102 to determine when the one or more areas 102 were last sterilized. In some embodiments, gas chromatography can be used to detect one or more sterilization agents 108. In some embodiments, one or more survey units 110 can communicate with one or more recording units 120 to determine when one or more areas 102 were last sterilized. In some embodiments, one or more survey units 110 can communicate with one or more sterilization units 114 to determine when one or more areas 102 were last sterilized. In some embodiments, one or more survey units 110 can use one or more methods to determine when one or more areas 102 should be sterilized. Numerous additional known methods may be used to determine if one or more areas 102 should be sterilized.

At operation 304, the surveying operation 210 may include determining if one or more areas 102 should not be sterilized. In some embodiments, one or more survey units 110 can survey one or more areas 102 to determine if the one or more areas 102 should not be sterilized. In some embodiments, one or more survey units 110 can determine if a predetermined amount of time has passed since one or more areas 102 were last sterilized. Accordingly, one or more areas 102 may not be sterilized if less than a given amount of time has passed since the one or more areas 102 were last sterilized. In some embodiments, in order to determine when one or more areas 102 were last sterilized, one or more survey units 110 can communicate with one or more sensor units 118 that can communicate when the one or more areas 102 were last sterilized. In other embodiments, one or more survey units 110 can detect phosphorescent emission from one or more phosphorescent materials included within one or more areas 102 to determine when the one or more areas 102 were last sterilized. In some embodiments, one or more survey units 110 can detect the presence, absence and/or concentration of one or more sterilization agents 108 within one or more areas 102 to determine when the one or more areas 102 were last sterilized. In some embodiments, gas chromatography can be use to detect one or more sterilization agents 108. In some embodiments, one or more survey units 110 can communicate with one or more recording units 120 to determine when one or more areas 102 were last sterilized. In some embodiments, one or more survey units 110 can communicate with one or more sterilization units 114 to determine when one or more areas 102 were last sterilized. In some embodiments, one or more survey units 110 can use one or more methods to determine when one or more areas 102 should be sterilized. Numerous additional known methods may be used to determine if one or more areas 102 should be sterilized.

At operation 306, the surveying operation 210 may include determining one or more surfaces 106 within the one or more areas 102 that should be sterilized. In some embodiments, one or more survey units 110 can survey one or more surfaces 106 within one or more areas 102 to determine if the one or more surfaces 106 should be sterilized. In some embodiments, one or more survey units 110 can determine if a predetermined amount of time has passed since one or more surfaces 106 were last sterilized. Accordingly, one or more surfaces 106 may be sterilized if more than a given amount of time has passed since the one or more surfaces 106 were last sterilized. In some embodiments, in order to determine when one or more surfaces 106 were last sterilized, one or more survey units 110 can communicate with one or more sensor units 118 that can communicate when the one or more surfaces 106 were last sterilized. In other embodiments, one or more survey units 110 can detect phosphorescent emission from one or more phosphorescent materials included on or within the one or more surfaces 106 to determine when the one or more surfaces 106 were last sterilized. In some embodiments, one or more survey units 110 can detect the presence, absence and/or concentration of one or more sterilization agents 108 on the one or more surfaces 106 to determine when the one or more surfaces 106 were last sterilized. In some embodiments, gas chromatography can be use to detect one or more sterilization agents 108. In some embodiments, one or more survey units 110 can communicate with one or more recording units 120 to determine when one or more surfaces 106 were last sterilized. In some embodiments, one or more survey units 110 can communicate with one or more sterilization units 114 to determine when one or more surfaces 106 were last sterilized. In some embodiments, one or more survey units 110 can use one or more methods to determine when one or more surfaces 106 should be sterilized. Numerous additional known methods may be used to determine if one or more surfaces 106 should be sterilized.

At operation 308, the surveying operation 210 may include determining one or more surfaces 106 within the one or more areas 102 that should not be sterilized. In some embodiments, one or more survey units 110 can survey one or more surfaces 106 within one or more areas 102 to determine if the one or more surfaces 106 should not be sterilized. In some embodiments, one or more survey units 110 can determine if a predetermined amount of time has passed since one or more surfaces 106 were last sterilized. Accordingly, one or more surfaces 106 may not be not sterilized if less than a given amount of time has passed since the one or more surfaces 106 were last sterilized. In some embodiments, in order to determine when one or more surfaces 106 were last sterilized, one or more survey units 110 can communicate with one or more sensor units 118 that can communicate when the one or more surfaces 106 were last sterilized. In other embodiments, one or more survey units 110 can detect phosphorescent emission from one or more phosphorescent materials included on or within the one or more surfaces 106 to determine when the one or more surfaces 106 were last sterilized. In some embodiments, one or more survey units 110 can detect the presence, absence and/or concentration of one or more sterilization agents 108 on the one or more surfaces 106 to determine when the one or more surfaces 106 were last sterilized. In some embodiments, gas chromatography can be use to detect one or more sterilization agents 108. In some embodiments, one or more survey units 110 can communicate with one or more recording units 120 to determine when one or more surfaces 106 were last sterilized. In some embodiments, one or more survey units 110 can communicate with one or more sterilization units 114 to determine when one or more surfaces 106 were last sterilized. In some embodiments, one or more survey units 110 can use one or more methods to determine when one or more surfaces 106 should be sterilized. Numerous additional known methods may be used to determine if one or more surfaces 106 should not be sterilized.

At operation 310, the surveying operation 210 may include determining one or more objects 104 within the one or more areas 102 that should be sterilized. In some embodiments, one or more survey units 110 can survey one or more objects 104 within one or more areas 102 to determine if the one or more objects 104 should be sterilized. In some embodiments, one or more survey units 110 can determine if a predetermined amount of time has passed since one or more objects 104 were last sterilized. Accordingly, one or more objects 104 may be sterilized if more than a given amount of time has passed since the one or more objects 104 were last sterilized. In some embodiments, in order to determine when one or more objects 104 were last sterilized, one or more survey units 110 can communicate with one or more sensor units 118 that can communicate when the one or more objects 104 were last sterilized. In other embodiments, one or more survey units 110 can detect phosphorescent emission from one or more phosphorescent materials included on or within one or more objects 104 to determine when the one or more objects 104 were last sterilized. In some embodiments, one or more survey units 110 can detect the presence, absence and/or concentration of one or more sterilization agents 108 on the one or more objects 104 to determine when the one or more objects 104 were last sterilized. In some embodiments, gas chromatography can be use to detect one or more sterilization agents 108. In some embodiments, one or more survey units 110 can communicate with one or more recording units 120 to determine when one or more objects 104 were last sterilized. In some embodiments, one or more survey units 110 can communicate with one or more sterilization units 114 to determine when one or more objects 104 were last sterilized. In some embodiments, one or more survey units 110 can use one or more methods to determine when one or more objects 104 should be sterilized. Numerous additional known methods may be used to determine if one or more objects 104 should be sterilized.

Figure 4:
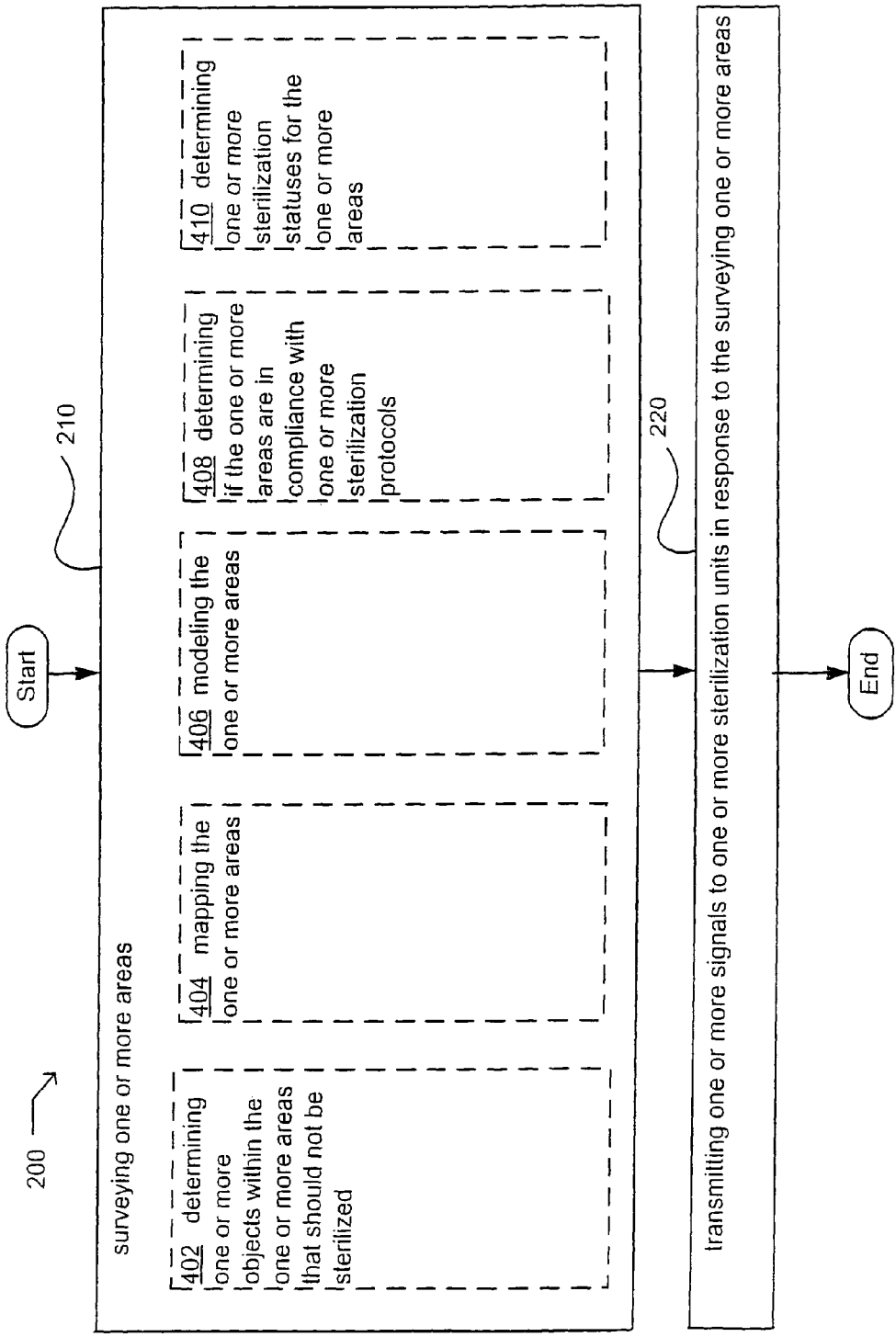
FIG. 4 illustrates an alternative embodiment of the example operation flow of FIG. 2.

FIG. 4 illustrates alternative embodiments of the example operational flow 200 of FIG. 2. FIG. 4 illustrates example embodiments where the surveying operation 210 may include at least one additional operation. Additional operations may include an operation 402, operation 404, operation 406, operation 408 and/or operation 410.

At operation 402, the surveying operation 210 may include determining one or more objects 104 within the one or more areas 102 that should not be sterilized. In some embodiments, one or more survey units 110 can survey one or more objects 104 within one or more areas 102 to determine if the one or more objects 104 should not be sterilized. In some embodiments, one or more survey units 110 can determine if a predetermined amount of time has passed since one or more objects 104 were last sterilized. Accordingly, one or more objects 104 may not be not sterilized if less than a given amount of time has passed since the one or more objects 104 were last sterilized. In some embodiments, in order to determine when one or more objects 104 were last sterilized, one or more survey units 110 can communicate with one or more sensor units 118 that can communicate when the one or more objects 104 were last sterilized. In other embodiments, one or more survey units 110 can detect phosphorescent emission from one or more phosphorescent materials included on or within one or more objects 104 to determine when the one or more objects 104 were last sterilized. In some embodiments, one or more survey units 110 can detect the presence, absence and/or concentration of one or more sterilization agents 108 on the one or more objects 104 to determine when the one or more objects 104 were last sterilized. In some embodiments, gas chromatography can be use to detect one or more sterilization agents 108. In some embodiments, one or more survey units 110 can communicate with one or more recording units 120 to determine when one or more objects 104 were last sterilized. In some embodiments, one or more survey units 110 can communicate with one or more sterilization units 114 to determine when one or more objects 104 were last sterilized. In some embodiments, one or more survey units 110 can use one or more methods to determine when one or more objects 104 should not be sterilized. Numerous additional known methods may be used to determine if one or more objects 104 should not be sterilized.

At operation 404, the surveying operation 210 may include mapping one or more areas 102. In some embodiments, one or more survey units 110 can map one or more areas 102. In some embodiments, one or more survey units 110 can map one or more areas with one or more three dimensional laser scanners. Such three dimensional laser scanners are known and are commercially available (i.e., Callidus 3D laser scanner and GX scanner from Trimble Navigation Limited, Sunnyvale, Calif.; LMS-Z360i from Riegl USA Inc., Orlando, Fla.). In some embodiments, one or more survey units 110 can determine the dimensions of one or more areas 102. In some embodiments, one or more survey units 110 can determine the positions of one or more surfaces 106 and/or one or more objects 104 within the one or more areas 102. In some embodiments, one or more survey units 110 can determine the dimensions of one or more areas 102 and the positions of one or more surfaces 106 and/or one or more objects 104 within the one or more areas 102.

At operation 406, the surveying operation 210 may include modeling one or more areas. In some embodiments, one or more survey units 110 can model one or more areas 102. In some embodiments, one or more survey units 110 can convert information received through mapping of one or more areas 102 and produce one or more models of the one or more areas 102. For example, in some embodiments, models can be produced that include the relative positions and dimensions of surfaces 106 and objects 104 within one or more areas 102. In some embodiments, models may be used to instruct one or more sterilization units 114 where to apply one or more sterilization agents 108 within one or more areas 102. In some embodiments, models may be used to instruct one or more sterilization units 114 where not to apply one or more sterilization agents 108 within one or more areas 102. Accordingly, in some embodiments, one or more areas 102 that include one or more humans can be sterilized without exposing the one or more humans to one or more sterilization agents 108. In some embodiments, one or more sterilization units 114 can sterilize one or more areas 102 that include one or more humans with sterilizing radiation without exposing the one or more humans to the sterilizing radiation.

At operation 408, the surveying operation 210 may include determining if one or more areas 102 are in compliance with one or more sterilization protocols. In some embodiments, one or more survey units 110 can determine if one or more areas 102 are in compliance with one or more sterilization protocols. In some embodiments, one or more sterilization protocols may be assigned to one or more areas 102. In some embodiments, a sterilization protocol may specify the immediacy, latency, intensity and time-integrated intensity of sterilizing radiation that is to be applied within one or more areas 102 as a function of either relative or absolute location within the one or more areas 102. In some embodiments, a sterilization protocol may specify one or more types of sterilization agents 108 that are to be applied to one or more areas 102. In some embodiments, a sterilization protocol may specify one or more types of sterilization agents 108 that are not to be applied to one or more areas 102. In some embodiments, a sterilization protocol may specify the frequency with which one or more sterilization agents 108 are to be applied to one or more areas 102. In some embodiments, a sterilization protocol may specify the intensity and/or concentration that one or more types of sterilization agents 108 that are to be applied to one or more areas 102. Numerous sterilization protocols can be assigned to one or more areas 102. In some embodiments, such protocols can be used to specify the intensity with which one or more areas 102 are sterilized to account for high patient-hazard and/or high infectivity likelihood areas to ensure that such areas receive rigorous and/or frequent sterilization treatment. Accordingly, in some embodiments, one or more survey units 110 can communicate with one or more recording units 120, one or more sensor units 118, one or more sterilization units 114, and substantially any combination thereof to determine if one or more areas 102 have been sterilized in accordance with a sterilization protocol. In some embodiments, one or more survey units 110 can determine how much time has passed since one or more areas 102 were last sterilized. Accordingly, one or more survey units 110 can determine if one or more areas 102 are in compliance with one or more protocols that call for sterilization of the one or more areas 102 at given time intervals. In some embodiments, one or more survey units 110 can communicate with one or more sensor units 118 to determine one or more areas 102 were last sterilized. In other embodiments, one or more survey units 110 can detect phosphorescent emission from one or more phosphorescent materials included within one or more areas 102 to determine when the one or more areas 102 were last sterilized. In some embodiments, one or more survey units 110 can detect the presence, absence and/or concentration of one or more sterilization agents 108 within the one or more areas 102 to determine when the one or more areas 102 were last sterilized. In some embodiments, gas chromatography can be use to detect one or more sterilization agents 108. In some embodiments, one or more survey units 110 can communicate with one or more recording units 120 to determine when one or more areas 102 were last sterilized. In some embodiments, one or more survey units 110 can communicate with one or more sterilization units 114 to determine when one or more areas 102 were last sterilized. One or more survey units 110 can use numerous methods to determine if one or more areas 102 are in compliance with one or more sterilization protocols.

At operation 410, the surveying operation 210 may include determining one or more sterilization statuses for one or more areas 102. In some embodiments, one or more survey units 110 can determine one or more sterilization statuses for one or more areas 102. In some embodiments, the sterilization status of one or more areas 102 can be relative to one or more sterilization levels assigned to the one or more areas 102. For example, some areas may be assigned a very high sterilization level where very high levels of sterility are desired. Examples of areas where a very high level of sterility may be desired include, but are not limited to, hospital operating rooms, pharmaceutical packaging facilities, food packaging facilities, nude mouse facilities, hospital wards, and the like. In other examples, areas where the levels of sterility may not need to be as high can be assigned a lower sterilization level. In some embodiments, one or more sterilization levels that are assigned to one or more areas 102 may include parameters for time of sterilization, frequency of sterilization, type of sterilization agent 108 to be applied, intensity of sterilization, use of multiple sterilization agents 108, risk-level assigned to one or more areas 102, types of contamination occurring within one or more areas 102, disease-state of one or more patients within one or more areas 102, and the like. In some embodiments, one or more survey units 110 can determine one or more sterilization statuses of one or more areas 102 which indicate if the one or more areas 102 need to be sterilized or whether the one or more areas 102 satisfy the desired sterilization level. In some embodiments, one or more survey units 110 can determine when one or more areas 102 that are currently sterile should be sterilized again. In such embodiments, one or more survey units 110 can instruct one or more sterilization units 114 when to sterilize the one or more areas 102. In some embodiment, one or more survey units 110 can determine if the sterilization level assigned to one or more areas 102 has changed and whether the one or more areas 102 satisfy the newly assigned sterilization level. In such embodiments, one or more survey units 110 can instruct one or more sterilization units 114 whether or not to sterilize the one or more areas 102.

Figure 5:
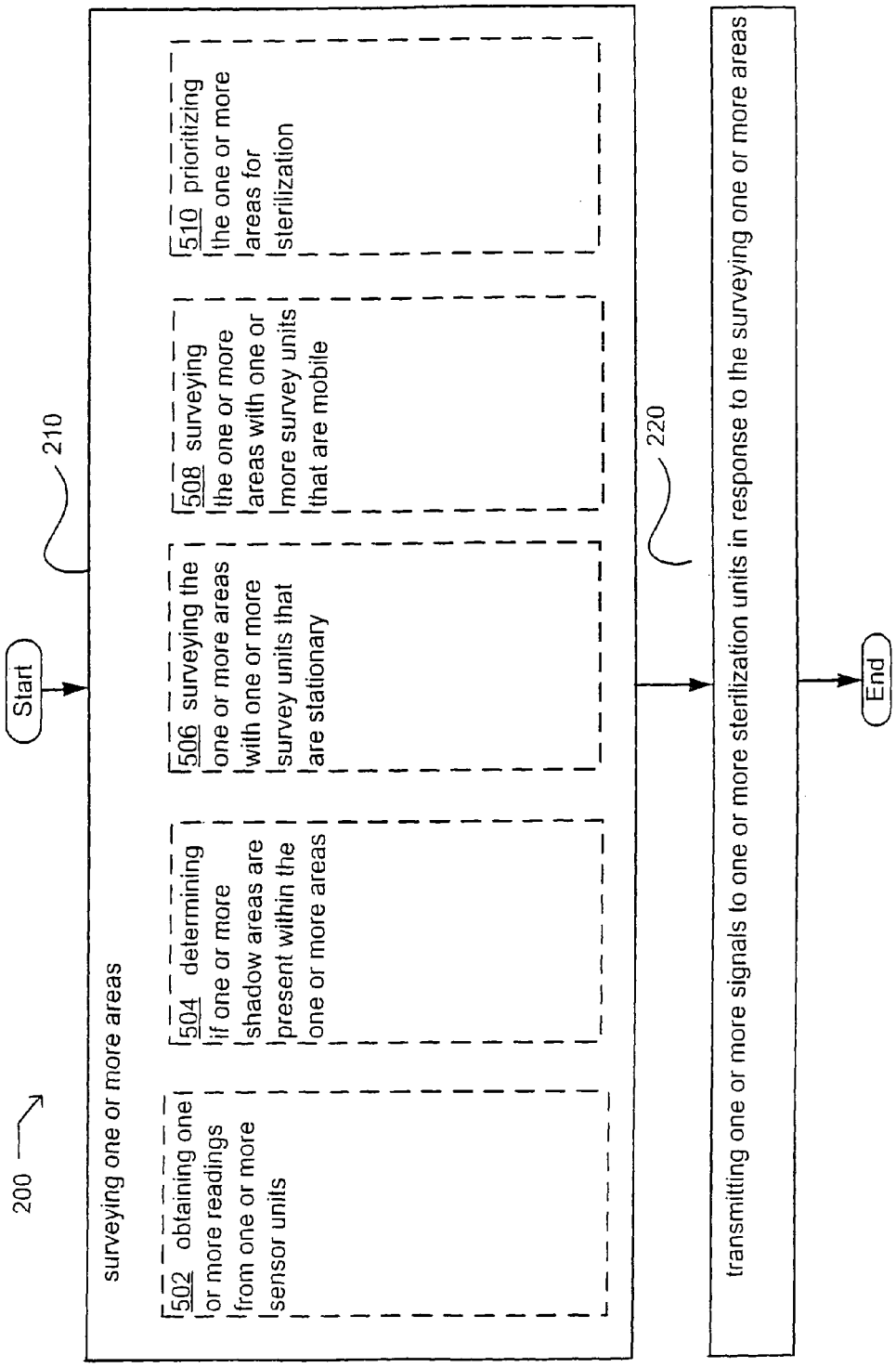
FIG. 5 illustrates an alternative embodiment of the example operation flow of FIG. 2.

FIG. 5 illustrates alternative embodiments of the example operational flow 200 of FIG. 2. FIG. 5 illustrates example embodiments where the surveying operation 210 may include at least one additional operation. Additional operations may include an operation 502, operation 504, operation 506, operation 508 and/or operation 510.

At operation 502, the surveying operation 210 may include obtaining one or more readings from one or more sensor units 118. In some embodiments, one or more survey units 110 can obtain one or more readings from one or more sensor units 118. In some embodiments, one or more survey units 110 can obtain one or more readings from one or more sensor units 118 that indicate one or more times when one or more areas 102 were sterilized. In some embodiments, one or more survey units 110 can obtain one or more readings from one or more sensor units 118 that indicate how often one or more areas 102 are sterilized. In some embodiments, one or more survey units 110 can obtain one or more readings from one or more sensor units 118 that indicate the intensity with which one or more areas 102 are sterilized. In some embodiments, one or more survey units 110 can obtain one or more readings from one or more sensor units 118 that indicate whether or not one or more surfaces 106 within one or more areas 102 have been sterilized. In some embodiments, one or more survey units 110 can obtain one or more readings from one or more sensor units 118 that indicate one or more types of sterilization agents 108 that have been applied within one or more areas 102. In some embodiments, one or more survey units 110 can obtain one or more readings from one or more sensor units 118 that indicate one or more types of sterilization agents 108 that have been applied to one or more surfaces 106 within one or more areas 102. In some embodiments, one or more survey units 110 can obtain one or more readings from one or more sensor units 118 that indicate one or more types of sterilization agents 108 that have been applied to one or more objects 104 within one or more areas 102. In some embodiments, one or more survey units 110 can obtain one or more readings from one or more sensor units 118 that indicate one or more types of sterilization agents 108 that have been applied to one or more objects 104 or one or more surfaces 106 within one or more areas 102.

At operation 504, the surveying operation 210 may include determining if one or more shadow areas are present within one or more areas 102. In some embodiments, one or more survey units 110 can determine if one or more shadow areas are present within one or more areas 102. In some embodiments, shadow areas may occur when radiation is blocked from irradiating one or more shadow areas by one or more objects 104 positioned between one or more sterilization units 114 that emit radiation and the one or more shadow areas. Determining where shadow areas occur allows those shadow areas to be assigned non-sterile status. Alternatively, determining the existence of such shadow areas provides for irradiation of the shadow areas with radiation emitted from another sterilization unit 114 that may be moved into, or next to, the one or more shadow areas. In some embodiments, the position of one or more shadow areas within one or more areas 102 may be determined by irradiating the one or more areas 102 with radiation emitted from one or more sterilization units 114 and then moving one or more survey units 110 around the one or more areas 102 to determine where the radiation does not impinge. In some embodiments, shadow areas can be predicted through use of computer modeling to determine if radiation, such as ultraviolet light, emitted from one or more sterilization units 114 will impinge on one or more areas 102. Additional methods may be used to determine if one or more shadow areas are present within one or more areas 102 that include the use of one or more sensor units 118 positioned throughout the one or more areas, use of indicators that phosphoresce or change color when irradiated, and the like.

At operation 506, the surveying operation 210 may include surveying one or more areas 102 with one or more survey units 110 that are stationary. In some embodiments, one or more survey units 110 that are stationary and one or more survey units 110 that are mobile can be used to survey one or more areas 102. In some embodiments, one or more survey units 110 that are stationary may be permanently positioned within one or more areas 102. In some embodiments, one or more survey units 110 that are stationary may be transiently positioned within one or more areas 102. In some embodiments, one or more survey units 110 that are stationary may be positioned within one or more areas 102 so that the one or more survey units 110 can survey substantially all surfaces 106 and/or substantially all objects 104 within the one or more areas 102.

At operation 508, the surveying operation 210 may include surveying one or more areas 102 with one or more survey units 110 that are mobile. In some embodiments, one or more survey units 110 that are stationary and one or more survey units 110 that are mobile can be used to survey one or more areas 102. In some embodiments, one or more survey units 110 that are mobile may be permanently positioned within one or more areas 102. In some embodiments, one or more survey units 110 that are mobile may be transiently positioned within one or more areas 102. In some embodiments, one or more survey units 110 that are mobile may be moved about one or more areas 102 so that the one or more survey units 110 may survey substantially all surfaces 106 and/or substantially all objects 104 within the one or more areas 102.

At operation 510, the surveying operation 210 may include prioritizing one or more areas 102 for sterilization. In some embodiments, one or more survey units 110 can prioritize one or more areas 102 for sterilization. In some embodiments, one or more areas 102 can be prioritized for sterilization based on the immediacy of the need for sterilization of the one or more areas 102. For example, an operating room may be sterilized before other areas 102 due to the existence of an emergency surgery that is to be done within the operating room. In some embodiments, one or more areas 102 can be prioritized for sterilization based on the presence of a highly infectious agent within the one or more areas 102. For example, an examination room in a hospital may be sterilized before other areas 102 due to the presence of a patient who is infected with smallpox within the examination room. In some embodiments, one or more areas 102 can be prioritized for sterilization based on conformance of the one or more areas 102 with a sterilization protocol. Numerous criteria may be used to prioritize one or more areas 102 for sterilization. In some embodiments, one or more survey units 110 can prioritize one or more areas 102 for sterilization based on one or more surveys done by the one or more survey units 110. In some embodiments, one or more survey units 110 can prioritize one or more areas 102 for sterilization following communication with one or more sensor units 118. In some embodiments, one or more survey units 110 can prioritize one or more areas 102 for sterilization following communication with one or more recording units 120. In some embodiments, one or more survey units 110 can prioritize one or more areas 102 for sterilization following user interaction 124.

Figure 6:
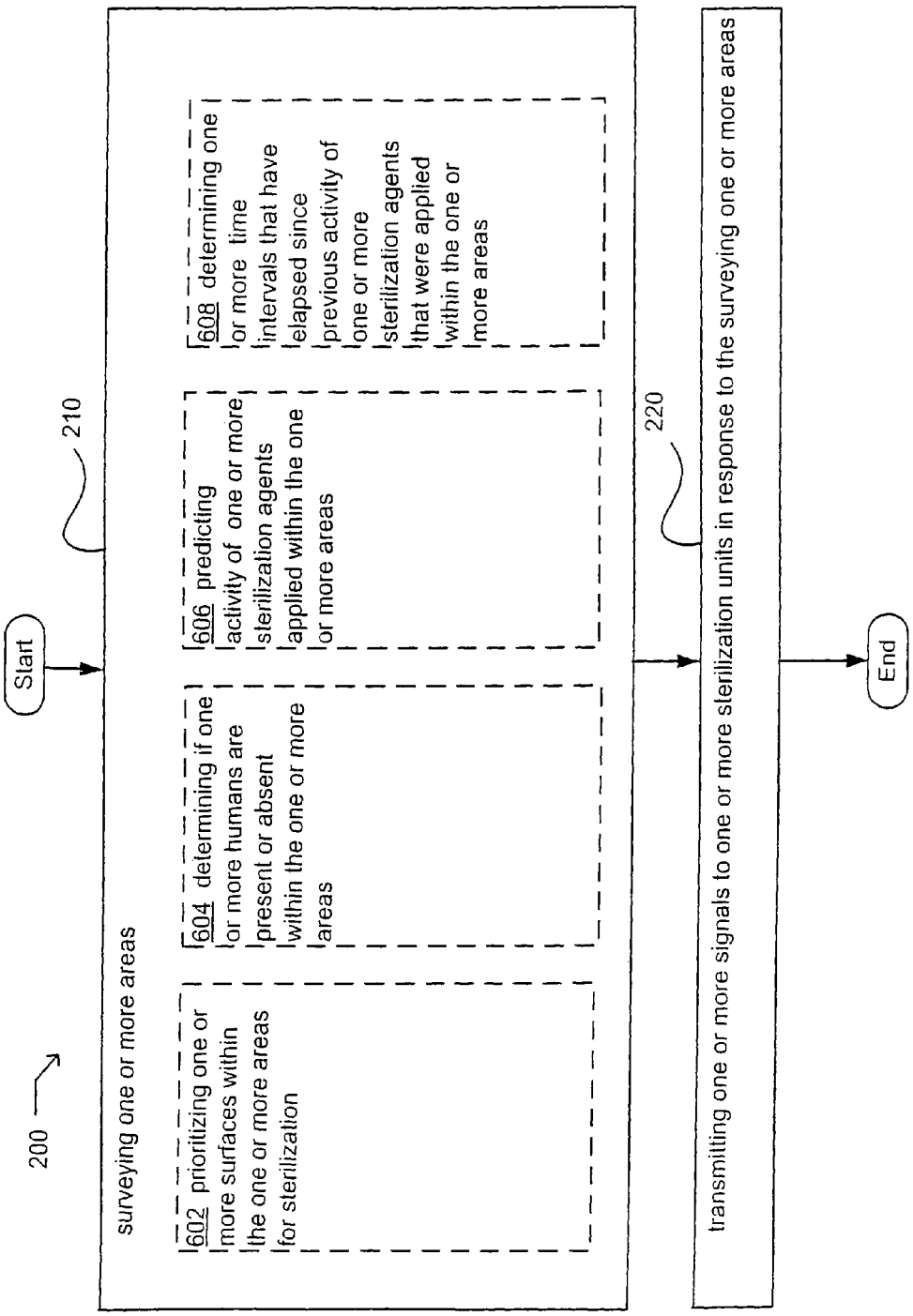
FIG. 6 illustrates an alternative embodiment of the example operation flow of FIG. 2.

FIG. 6 illustrates alternative embodiments of the example operational flow 200 of FIG. 2. FIG. 6 illustrates example embodiments where the surveying operation 210 may include at least one additional operation. Additional operations may include an operation 602, operation 604, operation 606 and/or operation 608.

At operation 602, the surveying operation 210 may include prioritizing one or more surfaces 106 within one or more areas 102 for sterilization. In some embodiments, one or more survey units 110 can prioritize one or more surfaces 106 within one or more areas 102 for sterilization. In some embodiments, one or more surfaces 106 can be prioritized for sterilization based on the immediacy of the need for the one or more surfaces 106 or one or more areas 102 in which the one or more surfaces 106 are included to be sterilized. For example, a surface 106 within an operating room may be sterilized before other areas 102 due to the existence of an emergency surgery that is to be done within the operating room. In some embodiments, one or more surfaces 106 can be prioritized for sterilization based on the presence of a highly infectious agent on and/or within the one or more surfaces 106. For example, a surface 106 within an examination room in a hospital may be sterilized before other areas 102 due to the presence of a patient who is infected with smallpox within the examination room. In some embodiments, one or more surfaces 106 can be prioritized for sterilization based on conformance of the one or more surfaces 106, or one or more areas 102 in which the one or more surfaces 106 are included, with a sterilization protocol. Numerous criteria may be used to prioritize one or more surfaces 106 for sterilization. In some embodiments, one or more survey units 110 can prioritize one or more surfaces 106 for sterilization based on one or more surveys done by the one or more survey units 110. In some embodiments, one or more survey units 110 can prioritize one or more surfaces 106 for sterilization following communication with one or more sensor units 118. In some embodiments, one or more survey units 110 can prioritize one or more surfaces 106 for sterilization following communication with one or more recording units 120. In some embodiments, one or more survey units 110 can prioritize one or more surfaces 106 for sterilization following user interaction 124.

At operation 604, the surveying operation 210 may include determining if one or more humans are present or absent within one or more areas 102. In some embodiments, one or more survey units 110 can detect the presence or absence of one or more humans within one or more areas 102. In some embodiments, one or more survey units 110 can utilize one or more transmitting units 116 to transmit one or more signals 112 to one or more sterilization units 114 to avoid applying one or more sterilization agents 108 onto one or more humans present within one or more areas 102. In some embodiments, one or more survey units 110 can utilize one or more transmitting units 116 to transmit one or more signals 112 to one or more sterilization units 114 to apply one or more sterilization agents 108 onto one or more humans present within one or more areas 102. In some embodiments, one or more survey units 110 can determine an amount of radiation to which one or more humans have been exposed while within one or more areas 102. In some embodiments, the radiation is light. In some embodiments, the radiation is ultraviolet light. In some embodiments, the radiation is infrared radiation. In some embodiments, the radiation is gamma radiation. In some embodiments, the radiation is microwave radiation. In some embodiments, one or more survey units 110 can detect radiation that has been reflected onto one or more humans within one or more areas 102. Examples of such humans include, but are not limited to, hospital patients, dental patients, nurses, physicians, pharmaceutical workers, food workers, transportation workers, and the like. In some embodiments, one or more survey units 110 can determine an amount of radiation that is incident on one or more surfaces 106 that occur on one or more humans. Examples of such surfaces 106 include, but are not limited to, open wounds, eyes, skin, and the like.

At operation 606, the surveying operation 210 may include predicting activity of one or more sterilization agents applied within one or more areas 102. In some embodiments, one or more survey units 110 can predict the activity of one or more sterilization agents 108 that are applied within one or more areas 102. In some embodiments, one or more survey units 110 can utilize the identity, concentration, time of application, and/or substantially any combination thereof of one or more sterilization agents 108 to one or more areas 102 and to determine the activity of the one or more sterilization agents 108 on one or more types of contamination that may or may not be present within the one or more areas 102. In some embodiments, the identity, concentration, time of application, and/or substantially any combination thereof, of one or more sterilization agents 108 to one or more areas 102 may be determined by one or more survey units 110. In some embodiments, one or more sensor units 118, sterilization units 114, recording units 120, users 122, or substantially any combination thereof, may communicate the identity, concentration, time of application, and/or substantially any combination thereof, of one or more sterilization agents 108 that were applied to one or more areas 102 to one or more survey units 110.

At operation 608, the surveying operation 210 may include determining one or more time intervals that have elapsed since previous activity of one or more sterilization agents 108 that were applied within one or more areas 102. In some embodiments, one or more survey units 110 can determine one or more time intervals that have elapsed since previous activity of one or more sterilization agents 108 that were applied within one or more areas 102. In some embodiments, one or more time intervals that have elapsed since previous activity of one or more sterilization agents 108 that were applied by one or more sterilization units 114 within one or more areas 102 can be communicated to one or more survey units 110 by one or more sensor units 118, sterilization units 114, recording units 120, users 122, or substantially any combination thereof. In some embodiments, the one or more sterilization agents 108 may be applied by one or more sterilization units 114.

Figure 7:
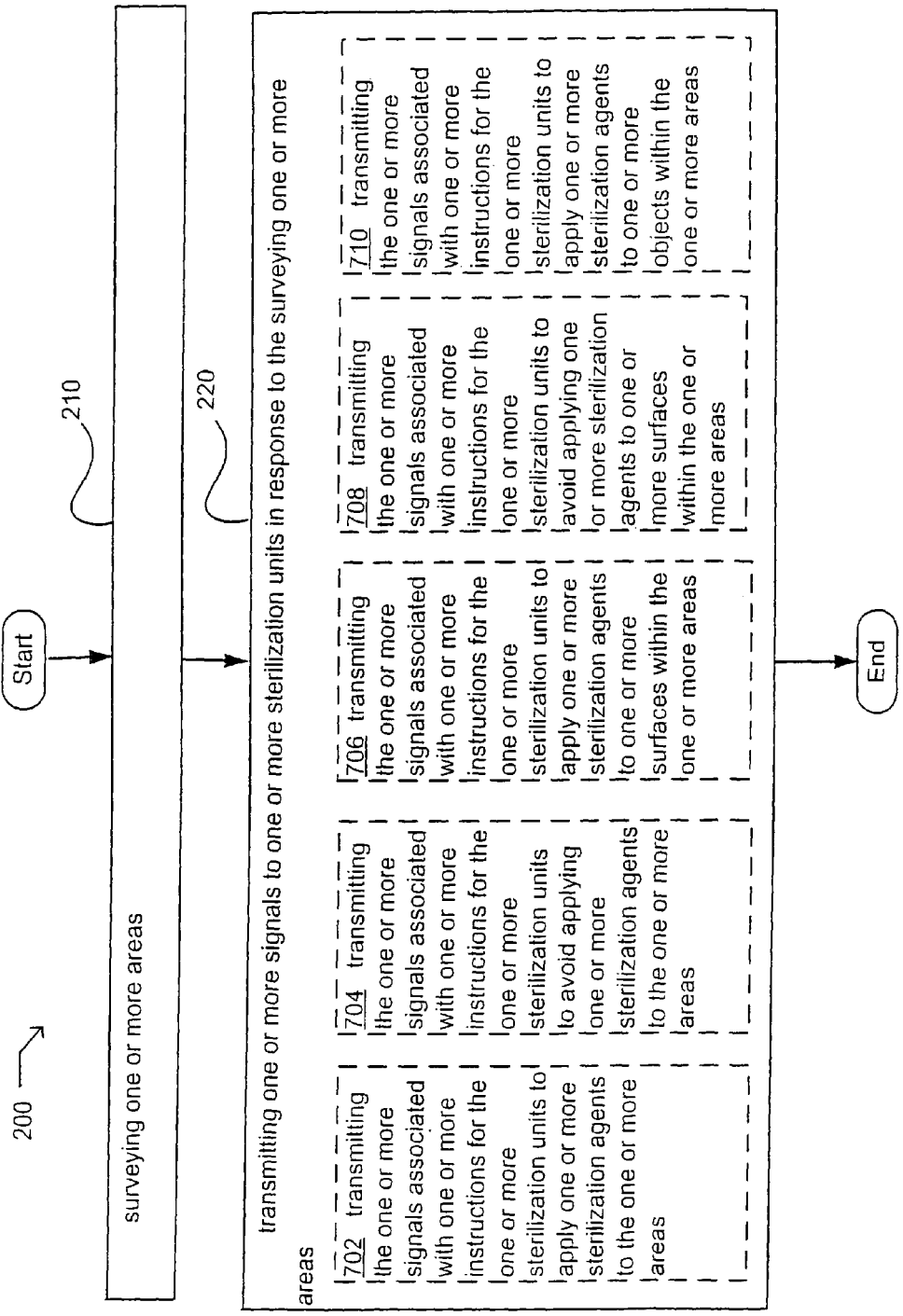
FIG. 7 illustrates an alternative embodiment of the example operation flow of FIG. 2.

FIG. 7 illustrates alternative embodiments of the example operational flow 200 of FIG. 2. FIG. 7 illustrates example embodiments where the transmitting operation 220 may include at least one additional operation. Additional operations may include an operation 702, operation 704, operation 706, operation 708 and/or operation 710.

At operation 702, the transmitting operation 220 may include transmitting one or more signals 112 associated with one or more instructions for one or more sterilization units 114 to apply one or more sterilization agents 108 to one or more areas 102. In some embodiments, one or more transmitting units 116 can transmit one or more signals 112 associated with one or more instructions for one or more sterilization units 114 to apply one or more sterilization agents to one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more areas 102 for sterilization. In some embodiments, one or more signals 112 are associated with one or more humans that are present or absent within one or more areas 102. In some embodiments, one or more signals 112 are associated with one or more instructions for one or more sterilization units 114 to apply one or more sterilization agents 108 that are identified to one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

At operation 704, the transmitting operation 220 may include transmitting one or more signals 112 associated with one or more instructions for one or more sterilization units 114 to avoid applying one or more sterilization agents 108 to one or more areas 102. In some embodiments, one or more transmitting units 116 can transmit one or more signals 112 associated with one or more instructions for one or more sterilization units 114 to avoid applying one or more sterilization agents to one or more areas 102. The one or more signals 112 can include numerous types of information. In some embodiments, one or more signals 112 can include one or more instructions for one or more sterilization units 114 to avoid applying one or more sterilization agents 108 to one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more areas 102 for sterilization. In some embodiments, one or more signals 112 are associated with one or more humans that are present or absent within one or more areas 102. In some embodiments, one or more signals 112 are associated with one or more instructions indicating one or more portions of one or more areas 102 where one or more sterilization units 110 are not to apply one or more sterilization agents 108. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

At operation 706, the transmitting operation 220 may include transmitting one or more signals 112 associated with one or more instructions for one or more sterilization units 114 to apply one or more sterilization agents 108 to one or more surfaces within one or more areas 102. In some embodiments, one or more transmitting units 116 can transmit one or more signals 112 associated with one or more instructions for one or more sterilization units 114 to apply one or more sterilization agents 108 to one or more surfaces 106 within one or more areas 102. The one or more signals 112 can include numerous types of information. In some embodiments, one or more signals 112 can include one or more instructions for one or more sterilization units 114 to apply one or more sterilization agents 108 to one or more surfaces 106 within one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more surfaces 106 within one or more areas 102 for sterilization. In some embodiments, one or more signals 112 are associated with one or more humans that are present or absent within one or more areas 102. In some embodiments, one or more signals 112 are associated with one or more instructions for one or more sterilization units 114 to apply one or more sterilization agents 108 that are identified to one or more surfaces 106 within one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied to one or more surfaces 106 within one or more areas 102.

At operation 708, the transmitting operation 220 may include transmitting one or more signals associated with one or more instructions for one or more sterilization units to avoid applying one or more sterilization agents to one or more surfaces within the one or more areas. In some embodiments, one or more transmitting units 116 can transmit one or more signals 112 associated with one or more instructions for one or more sterilization units 114 to avoid applying one or more sterilization agents 108 to one or more surfaces 106 within one or more areas 102. The one or more signals 112 can include numerous types of information. In some embodiments, one or more signals 112 can include one or more instructions for one or more sterilization units 114 to avoid applying one or more sterilization agents 108 to one or more surfaces 106 within one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more surfaces 106 within one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more surfaces 106 within one or more areas 102 for sterilization. In some embodiments, one or more signals 112 are associated with one or more humans that are present or absent within one or more areas 102. In some embodiments, one or more signals 112 are associated with one or more instructions for one or more sterilization units 114 to apply one or more sterilization agents 108 that are identified to one or more surfaces 106 within one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied to one or more surfaces 106 within one or more areas 102.

At operation 710, the transmitting operation 220 may include transmitting one or more signals 112 associated with one or more instructions for one or more sterilization units 114 to apply one or more sterilization agents 108 to one or more objects 104 within one or more areas 102. In some embodiments, one or more transmitting units 116 can transmit one or more signals 112 associated with one or more instructions for one or more sterilization units 114 to apply one or more sterilization agents 108 to one or more objects 104 within one or more areas 102. The one or more signals 112 can include numerous types of information. In some embodiments, one or more signals 112 can include one or more instructions for one or more sterilization units 114 to apply one or more sterilization agents 108 to one or more objects 104 within one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more objects 104 within one or more areas 102 for sterilization. In some embodiments, one or more signals 112 are associated with one or more humans that are present or absent within one or more areas 102. In some embodiments, one or more signals 112 are associated with one or more instructions for one or more sterilization units 114 to apply one or more sterilization agents 108 that are identified to one or more objects 104 within one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

Figure 8:
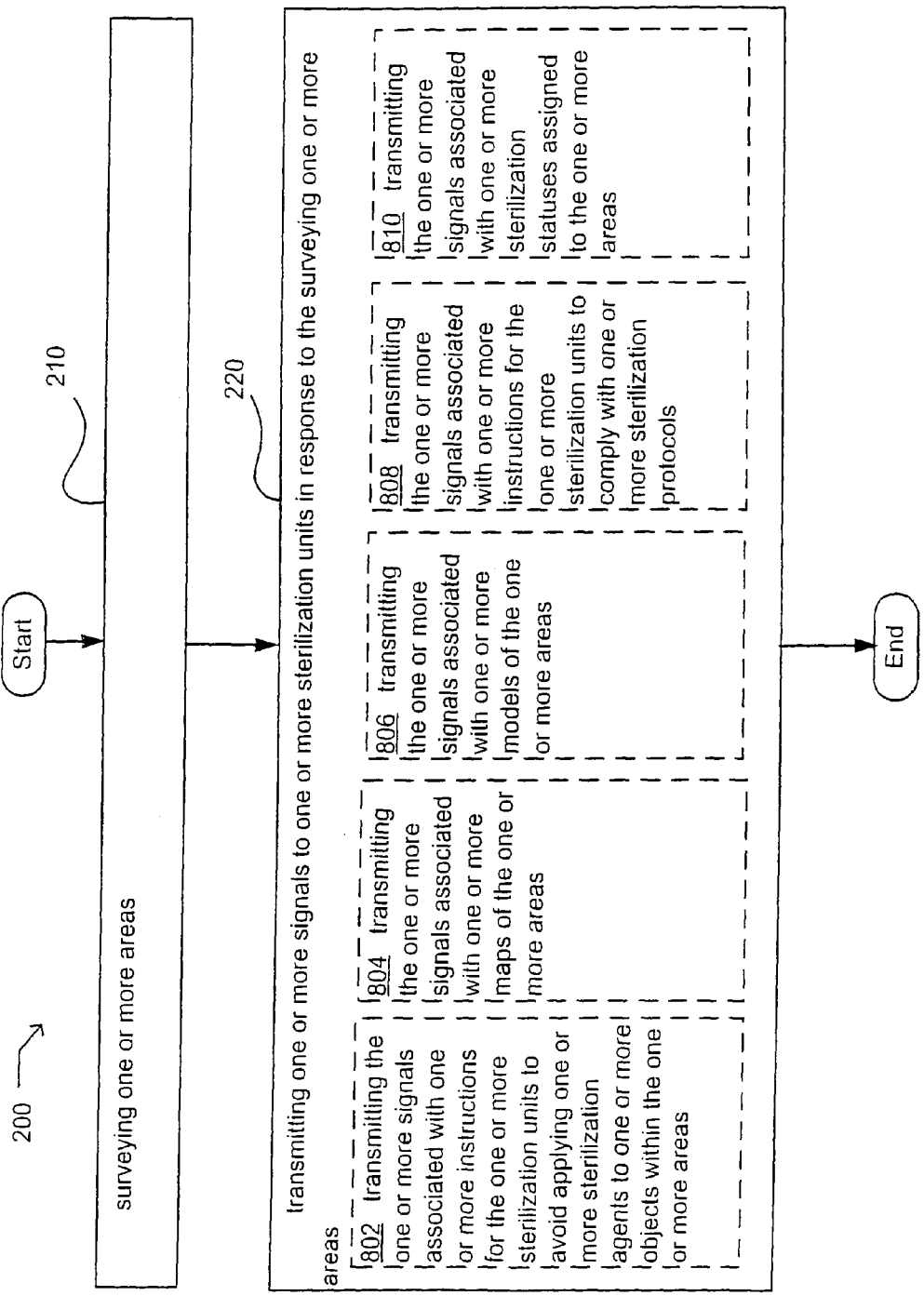
FIG. 8 illustrates an alternative embodiment of the example operation flow of FIG. 2.

FIG. 8 illustrates alternative embodiments of the example operational flow 200 of FIG. 2. FIG. 8 illustrates example embodiments where the transmitting operation 220 may include at least one additional operation. Additional operations may include an operation 802, operation 804, operation 806, operation 808 and/or operation 810.

At operation 802, the transmitting operation 220 may include transmitting one or more signals 112 associated with one or more instructions for the one or more sterilization units 114 to avoid applying one or more sterilization agents 108 to one or more objects within one or more areas 102. In some embodiments, one or more transmitting units 116 can transmit one or more signals 112 associated with one or more instructions for one or more sterilization units 114 to avoid applying one or more sterilization agents 108 to one or more objects 104 within one or more areas 102. The one or more signals 112 can include numerous types of information. In some embodiments, one or more signals 112 can include one or more instructions for one or more sterilization units 114 to avoid applying one or more sterilization agents 108 to one or more objects 104 within one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more objects 104 within one or more areas 102 for sterilization. In some embodiments, one or more signals 112 are associated with one or more humans that are present or absent within one or more areas 102. In some embodiments, one or more signals 112 are associated with one or more instructions for one or more sterilization units 114 to avoid applying one or more sterilization agents 108 that are identified to one or more objects 104 within one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

At operation 804, the transmitting operation 220 may include transmitting one or more signals 112 associated with one or more maps of one or more areas 102. In some embodiments, one or more transmitting units 116 can transmit one or more signals 112 associated with one or more maps of one or more areas 102. In some embodiments, one or more transmitting units 116 can transmit one or more signals 112 associated with the dimensions of one or more areas 102. In some embodiments, one or more transmitting units 116 can transmit one or more signals 112 associated with one or more positions of one or more surfaces 106 and/or one or more objects 104 within one or more areas 102. In some embodiments, one or more transmitting units 116 can transmit one or more signals 112 associated with the dimensions of one or more areas 102 and one or more positions of one or more surfaces 106 and/or one or more objects 104 within one or more areas 102. In some embodiments, one or more signals 112 associated with one or more maps of one or more areas 102 are transmitted to one or more sterilization units 114. The one or more signals 112 can include numerous types of information. In some embodiments, one or more signals 112 can include one or more instructions for one or more sterilization units 114 to apply one or more sterilization agents 108 to one or more areas 102. In some embodiments, the one or more signals 112 can include one or more instructions for one or more sterilization units 114 to avoid applying one or more sterilization agents 108 to one or more areas 102. In some embodiments, one or more signals 112 can include one or more instructions for one or more sterilization units 114 to apply one or more sterilization agents 108 to one or more surfaces 106 within one or more areas 102. In some embodiments, one or more signals 112 can include one or more instructions for one or more sterilization units 114 to avoid applying one or more sterilization agents 108 to one or more surfaces 106 within one or more areas 102. In some embodiments, one or more signals 112 can include one or more instructions for one or more sterilization units 114 to apply one or more sterilization agents 108 to one or more objects 104 within one or more areas 102. In some embodiments, one or more signals 112 can include one or more instructions for one or more sterilization units 114 to avoid applying one or more sterilization agents 108 to one or more objects 104 within one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more areas 102 for sterilization. In some embodiments, one or more signals 112 are associated with prioritizing one or more surfaces 106 within one or more areas 102 for sterilization. In some embodiments, one or more signals 112 are associated with one or more humans that are present or absent within one or more areas 102. In some embodiments, one or more signals 112 are associated with one or more instructions indicating one or more portions of one or more areas 102 where one or more sterilization units 114 are to apply one or more sterilization agents 108. In some embodiments, one or more signals 112 are associated with one or more instructions indicating one or more portions of one or more areas 102 where one or more sterilization units 110 are not to apply one or more sterilization agents 108. In some embodiments, one or more signals 112 are associated with one or more instructions for one or more sterilization units 114 to apply one or more sterilization agents 108 that are identified to one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

At operation 806, the transmitting operation 220 may include transmitting one or more signals associated with one or more models of the one or more areas. In some embodiments, one or more transmitting units 116 can transmit one or more signals 112 associated with one or more models of one or more areas 102. In some embodiments, one or more transmitting units 116 can transmit one or more signals 112 associated with the dimensions of one or more areas 102. In some embodiments, one or more transmitting units 116 can transmit one or more signals 112 associated with one or more positions of one or more surfaces 106 and/or one or more objects 104 within one or more areas 102. In some embodiments, one or more transmitting units 116 can transmit one or more signals 112 associated with the dimensions of one or more areas 102 and one or more positions of one or more surfaces 106 and/or one or more objects 104 within one or more areas 102. In some embodiments, one or more signals 112 associated with one or more models of one or more areas 102 are transmitted to one or more sterilization units 114. The one or more signals 112 can include numerous types of information. In some embodiments, one or more signals 112 can include one or more instructions for one or more sterilization units 114 to apply one or more sterilization agents 108 to one or more areas 102. In some embodiments, the one or more signals 112 can include one or more instructions for one or more sterilization units 114 to avoid applying one or more sterilization agents 108 to one or more areas 102. In some embodiments, one or more signals 112 can include one or more instructions for one or more sterilization units 114 to apply one or more sterilization agents 108 to one or more surfaces 106 within one or more areas 102. In some embodiments, one or more signals 112 can include one or more instructions for one or more sterilization units 114 to avoid applying one or more sterilization agents 108 to one or more surfaces 106 within one or more areas 102. In some embodiments, one or more signals 112 can include one or more instructions for one or more sterilization units 114 to apply one or more sterilization agents 108 to one or more objects 104 within one or more areas 102. In some embodiments, one or more signals 112 can include one or more instructions for one or more sterilization units 114 to avoid applying one or more sterilization agents 108 to one or more objects 104 within one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 from one or more survey units 110 that are stationary. In some embodiments, one or more signals 112 are transmitted to one or more sterilization units 114 from one or more survey units 110 that are mobile. In some embodiments, one or more signals 112 are associated with prioritizing one or more areas 102 for sterilization. In some embodiments, one or more signals 112 are associated with prioritizing one or more surfaces 106 within one or more areas 102 for sterilization. In some embodiments, one or more signals 112 are associated with one or more humans that are present or absent within one or more areas 102. In some embodiments, one or more signals 112 are associated with one or more instructions indicating one or more portions of one or more areas 102 where one or more sterilization units 114 are to apply one or more sterilization agents 108. In some embodiments, one or more signals 112 are associated with one or more instructions indicating one or more portions of one or more areas 102 where one or more sterilization units 110 are not to apply one or more sterilization agents 108. In some embodiments, one or more signals 112 are associated with one or more instructions for one or more sterilization units 114 to apply one or more sterilization agents 108 that are identified to one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

At operation 808, the transmitting operation 220 may include transmitting one or more signals 112 associated with one or more instructions for one or more sterilization units 114 to comply with one or more sterilization protocols. In some embodiments, one or more transmitting units 116 can transmit one or more signals 112 associated with one or more instructions for one or more sterilization units 114 to comply with one or more sterilization protocols. In some embodiments, one or more sterilization protocols may be assigned to one or more areas 102. In some embodiments, a sterilization protocol may specify the immediacy, latency, intensity and time-integrated intensity of sterilizing radiation that is to be applied within one or more areas 102 as a function of either relative or absolute location within the one or more areas 102. In some embodiments, a sterilization protocol may specify one or more types of sterilization agents 108 that are to be applied to one or more areas 102. In some embodiments, a sterilization protocol may specify one or more types of sterilization agents 108 that are not to be applied to one or more areas 102. In some embodiments, a sterilization protocol may specify the frequency with which one or more sterilization agents 108 are to be applied to one or more areas 102. In some embodiments, a sterilization protocol may specify the intensity and/or concentration that one or more types of sterilization agents 108 that are to be applied to one or more areas 102. Numerous sterilization protocols can be assigned to one or more areas 102. In some embodiments, such protocols can be used to specify the intensity with which one or more areas 102 are sterilized to account for high patient-hazard and/or high infectivity likelihood areas to ensure that such areas 102 receive rigorous and/or frequent sterilization treatment. In some embodiments, one or more transmitting units 116 can transmit one or more signals 112 to one or more recording units 120, one or more sensor units 118, one or more sterilization units 114, and substantially any combination thereof that are associated with one or more sterilization protocols. In some embodiments, one or more transmitting units 116 can transmit one or more signals 112 associated with how much time has passed since one or more areas 102 were last sterilized. In some embodiments, one or more transmitting units 116 can transmit one or more signals 112 associated with determining if one or more areas 102 are in compliance with one or more protocols that call for sterilization of the one or more areas 102 at given time intervals.

At operation 810, the transmitting operation 220 may include transmitting one or more signals 112 associated with one or more sterilization statuses assigned to one or more areas 102. In some embodiments, one or more transmitting units 116 can transmit one or more signals 112 associated with one or more sterilization statuses assigned to one or more areas 102. In some embodiments, the sterilization status of one or more areas 102 can be relative to one or more sterilization levels assigned to the one or more areas 102. For example, some areas 102 may be assigned a very high sterilization level where very high levels of sterility are desired. Examples of areas 102 where a very high level of sterility may be desired include, but are not limited to, hospital operating rooms, pharmaceutical packaging facilities, food packaging facilities, nude mouse facilities, hospital wards, and the like. In other examples, areas 102 where the levels of sterility may not need to be as high can be assigned a lower sterilization level. In some embodiments, one or more sterilization levels that are assigned to one or more areas 102 may include parameters for time of sterilization, frequency of sterilization, type of sterilization agent 108 to be applied, intensity of sterilization, use of multiple sterilization agents 108, risk-level assigned to one or more areas 102, types of contamination occurring within one or more areas 102, disease-state of one or more patients within one or more areas 102, and the like. In some embodiments, one or more transmitting units 116 can transmit one or more signals 112 associated with one or more sterilization statuses of one or more areas which indicate if the one or more areas 102 need to be sterilized or whether the one or more areas 102 satisfy the desired sterilization level. In some embodiments, one or more transmitting units 116 can transmit one or more signals 112 associated determining when one or more areas 102 that are currently sterile should be sterilized again. In some embodiments, one or more transmitting units 116 can transmit one or more signals 112 associated with instructing one or more sterilization units 114 when to sterilize the one or more areas 102. In some embodiments, one or more transmitting units 116 can transmit one or more signals 112 associated with determining if one or more sterilization levels assigned to one or more areas 102 have changed and whether the one or more areas 102 satisfy the one or more newly assigned sterilization levels.

Figure 9:
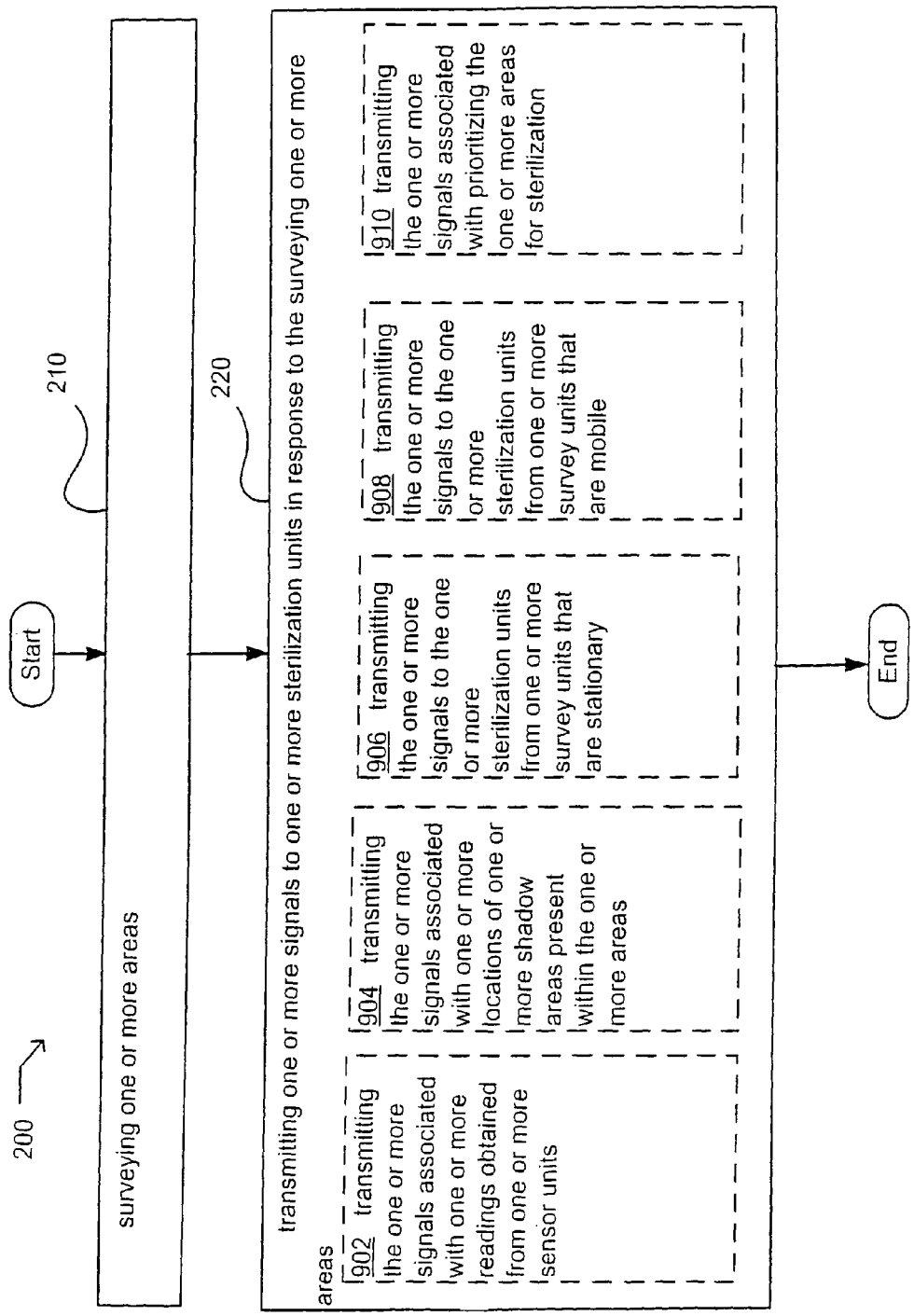
FIG. 9 illustrates an alternative embodiment of the example operation flow of FIG. 2.

FIG. 9 illustrates alternative embodiments of the example operational flow 200 of FIG. 2. FIG. 9 illustrates example embodiments where the transmitting operation 220 may include at least one additional operation. Additional operations may include an operation 902, operation 904, operation 906, operation 908 and/or operation 910.

At operation 902, the transmitting operation 220 may include transmitting one or more signals 112 associated with one or more readings obtained from one or more sensor units 118. In some embodiments, one or more transmitting units 116 can transmit one or more signals 112 associated with one or more readings obtained from one or more sensor units 118. In some embodiments, one or more transmitting units 116 can transmit one or more signals 112 associated with one or more readings obtained from one or more sensor units 118 to one or more sterilization units 114, one or more survey units 110, one or more recording units 120, and substantially any combination thereof. In some embodiments, one or more transmitting units 116 can transmit one or more signals 112 associated with one or more times when one or more areas 102 were sterilized. In some embodiments, one or more transmitting units 116 can transmit one or more signals 112 associated with how often one or more areas 102 are sterilized. In some embodiments, one or more transmitting units 116 can transmit one or more signals 112 associated with the intensity with which one or more areas 102 are sterilized. In some embodiments, one or more transmitting units 116 can transmit one or more signals 112 associated with whether or not one or more surfaces 106 within one or more areas 102 have been sterilized. In some embodiments, one or more transmitting units 116 can transmit one or more signals 112 associated with one or more types of sterilization agents 108 that have been applied within one or more areas 102. In some embodiments, one or more transmitting units 116 can transmit one or more signals 112 associated with one or more types of sterilization agents 108 that have been applied to one or more surfaces 106 within one or more areas 102. In some embodiments, one or more transmitting units 116 can transmit one or more signals 112 associated with one or more types of sterilization agents 108 that have been applied to one or more objects 104 within one or more areas 102. In some embodiments, one or more transmitting units 116 can transmit one or more signals 112 associated with one or more types of sterilization agents 108 that have been applied to one or more objects 104 and/or one or more surfaces 106 within one or more areas 102.

At operation 904, the transmitting operation 220 may include transmitting one or more signals 112 associated with one or more locations of one or more shadow areas present within one or more areas 102. In some embodiments, one or more transmitting units 116 can transmit one or more signals 112 associated with one or more locations of one or more shadow areas present within one or more areas 102. In some embodiments, shadow areas may occur when radiation is blocked from irradiating one or more shadow areas by one or more objects 104 positioned between one or more sterilization units 114 that emit radiation and the one or more shadow areas. In some embodiments, one or more transmitting units 116 can transmit one or more signals 112 associated with assigning non-sterile status to one or more shadow areas. In some embodiments, one or more transmitting units 116 can transmit one or more signals 112 associated with instructing one or more sterilization units 114 to sterilize one or more shadow areas.

At operation 906, the transmitting operation 220 may include transmitting one or more signals 112 to one or more sterilization units 114 from one or more survey units 110 that are stationary. In some embodiments, one or more transmitting units 116 can transmit one or more signals 112 to one or more sterilization units 114 from one or more survey units 110 that are stationary. The one or more signals 112 can include numerous types of information. In some embodiments, one or more signals 112 can include one or more instructions for one or more sterilization units 114 to apply one or more sterilization agents 108 to one or more areas 102. In some embodiments, one or more signals 112 can include one or more instructions for one or more sterilization units 114 to avoid applying one or more sterilization agents 108 to one or more areas 102. In some embodiments, one or more signals 112 can include one or more instructions for one or more sterilization units 114 to apply one or more sterilization agents 108 to one or more surfaces 106 within one or more areas 102. In some embodiments, one or more signals 112 can include one or more instructions for one or more sterilization units 114 to avoid applying one or more sterilization agents 108 to one or more surfaces 106 within one or more areas 102. In some embodiments, one or more signals 112 can include one or more instructions for one or more sterilization units 114 to apply one or more sterilization agents 108 to one or more objects 104 within one or more areas 102. In some embodiments, one or more signals 112 can include one or more instructions for one or more sterilization units 114 to avoid applying one or more sterilization agents 108 to one or more objects 104 within one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 that are stationary. In some embodiments, one or more signals 112 are transmitted to one or more sterilization units 114 that are mobile. In some embodiments, one or more signals 112 are associated with prioritizing one or more areas 102 for sterilization. In some embodiments, one or more signals 112 are associated with prioritizing one or more surfaces 106 within one or more areas 102 for sterilization. In some embodiments, one or more signals 112 are associated with one or more humans that are present or absent within one or more areas 102. In some embodiments, one or more signals 112 are associated with one or more instructions indicating one or more portions of one or more areas 102 where one or more sterilization units 114 are to apply one or more sterilization agents 108. In some embodiments, one or more signals 112 are associated with one or more instructions indicating one or more portions of one or more areas 102 where one or more sterilization units 110 are not to apply one or more sterilization agents 108. In some embodiments, one or more signals 112 are associated with one or more instructions for one or more sterilization units 114 to apply one or more sterilization agents 108 that are identified to one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

At operation 908, the transmitting operation 220 may include transmitting one or more signals to one or more sterilization units from one or more survey units that are mobile. In some embodiments, one or more transmitting units 116 can transmit one or more signals 112 to one or more sterilization units 114 from one or more survey units 110 that are mobile. The one or more signals 112 can include numerous types of information. In some embodiments, one or more signals 112 can include one or more instructions for one or more sterilization units 114 to apply one or more sterilization agents 108 to one or more areas 102. In some embodiments, one or more signals 112 can include one or more instructions for one or more sterilization units 114 to avoid applying one or more sterilization agents 108 to one or more areas 102. In some embodiments, one or more signals 112 can include one or more instructions for one or more sterilization units 114 to apply one or more sterilization agents 108 to one or more surfaces 106 within one or more areas 102. In some embodiments, one or more signals 112 can include one or more instructions for one or more sterilization units 114 to avoid applying one or more sterilization agents 108 to one or more surfaces 106 within one or more areas 102. In some embodiments, one or more signals 112 can include one or more instructions for one or more sterilization units 114 to apply one or more sterilization agents 108 to one or more objects 104 within one or more areas 102. In some embodiments, one or more signals 112 can include one or more instructions for one or more sterilization units 114 to avoid applying one or more sterilization agents 108 to one or more objects 104 within one or more areas 102. In some embodiments, one or more signals 112 are associated with one or more maps of one or more areas 102. In some embodiments, one or more signals 112 are associated with one or more models of one or more areas 102. In some embodiments, one or more signals 112 are associated with one or more instructions for one or more sterilization units 114 to comply with one or more sterilization protocols. In some embodiments, one or more signals 112 are associated with one or more sterilization statuses assigned to one or more areas 102. In some embodiments, one or more signals 112 are associated with one or more readings obtained from one or more sensor units 118. In some embodiments, one or more signals 112 are associated with one or more locations of one or more shadow areas present within one or more areas 102. In some embodiments, one or more signals 112 are transmitted to one or more sterilization units 114 that are stationary. In some embodiments, one or more signals 112 are transmitted to one or more sterilization units 114 that are mobile. In some embodiments, one or more signals 112 are associated with prioritizing one or more areas 102 for sterilization. In some embodiments, one or more signals 112 are associated with prioritizing one or more surfaces 106 within one or more areas 102 for sterilization. In some embodiments, one or more signals 112 are associated with one or more humans that are present or absent within one or more areas 102. In some embodiments, one or more signals 112 are associated with one or more instructions indicating one or more portions of one or more areas 102 where one or more sterilization units 114 are to apply one or more sterilization agents 108. In some embodiments, one or more signals 112 are associated with one or more instructions indicating one or more portions of one or more areas 102 where one or more sterilization units 110 are not to apply one or more sterilization agents 108. In some embodiments, one or more signals 112 are associated with one or more instructions for one or more sterilization units 114 to apply one or more sterilization agents 108 that are identified to one or more areas 102. In some embodiments, one or more signals 112 are associated with one or more instructions for one or more recording units 120. In some embodiments, one or more signals 112 are associated with one or more time intervals that have elapsed since one or more sterilization agents 108 were previously applied within one or more areas 102.

At operation 910, the transmitting operation 220 may include transmitting one or more signals 112 associated with prioritizing one or more areas 102 for sterilization. In some embodiments, one or more transmitting units 116 can transmit one or more signals 112 associated with prioritizing one or more areas 102 for sterilization. In some embodiments, one or more transmitting units 116 can transmit one or more signals 112 associated with the need for sterilization of the one or more areas 102. For example, an operating room may be sterilized before other areas 102 due to the existence of an emergency surgery that is to be done within the operating room. In some embodiments, one or more transmitting units 116 can transmit one or more signals 112 associated the presence of a highly infectious agent within the one or more areas 102. For example, an examination room in a hospital may be sterilized before other areas 102 due to the presence of a patient who is infected with smallpox within the examination room. In some embodiments, one or more transmitting units 116 can transmit one or more signals 112 associated with conformance with a sterilization protocol.

Figure 10:
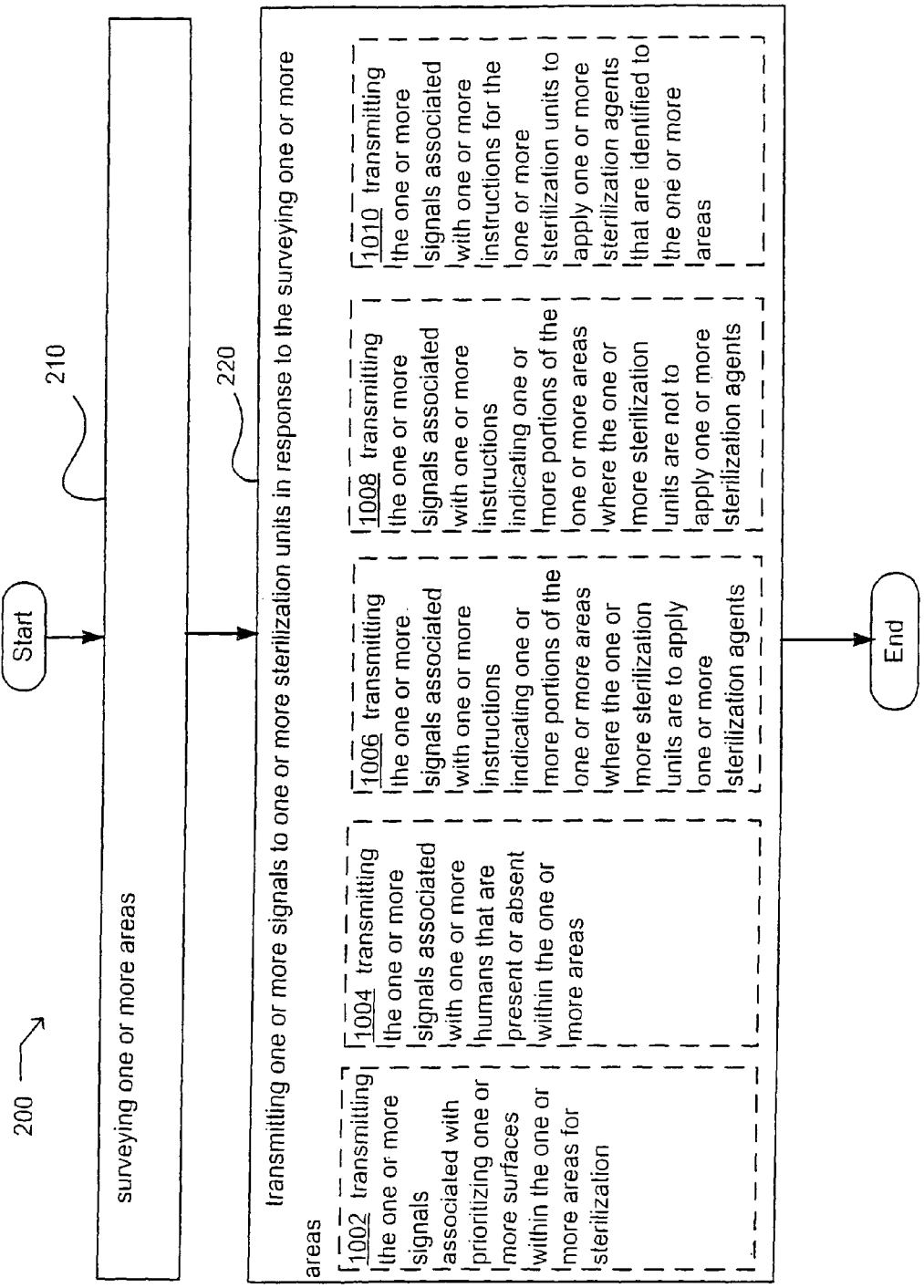
FIG. 10 illustrates an alternative embodiment of the example operation flow of FIG. 2.

FIG. 10 illustrates alternative embodiments of the example operational flow 200 of FIG. 2. FIG. 10 illustrates example embodiments where the transmitting operation 220 may include at least one additional operation. Additional operations may include an operation 1002, operation 1004, operation 1006, operation 1008 and/or operation 1010.

At operation 1002, the transmitting operation 220 may include transmitting one or more signals 112 associated with prioritizing one or more surfaces 106 within one or more areas 102 for sterilization. In some embodiments, one or more transmitting units 116 can transmit one or more signals 112 associated with prioritizing one or more surfaces 106 within one or more areas 102 for sterilization. In some embodiments, one or more transmitting units 116 can transmit one or more signals 112 associated with the need for sterilization of one or more surfaces 106 within one or more areas 102. For example, one or more surfaces 106 within an operating room may be sterilized before other areas 102 due to the existence of an emergency surgery that is to be done within the operating room. In some embodiments, one or more transmitting units 116 can transmit one or more signals 112 associated with the presence of a highly infectious agent within or on one or more surfaces 106 within one or more areas 102. For example, one or more surfaces 106 within an examination room in a hospital may be sterilized before other areas 102 due to the presence of a patient who is infected with smallpox within the examination room. In some embodiments, one or more transmitting units 116 can transmit one or more signals 112 associated with conformance with a sterilization protocol.

At operation 1004, the transmitting operation 220 may include transmitting one or more signals 112 associated with one or more humans that are present or absent within one or more areas 102. In some embodiments, one or more transmitting units 116 can transmit one or more signals 112 associated with one or more humans that are present or absent within one or more areas 102. In some embodiments, one or more transmitting units 116 can transmit one or more signals 112 associated with an amount of radiation, such as ultraviolet light, to which one or more humans have been exposed. In some embodiments, one or more transmitting units 116 can transmit one or more signals 112 associated with an amount of radiation, such as ultraviolet light, to which one or more humans have been exposed through reflection of the radiation onto the one or more humans. Examples of such humans include, but are not limited to, hospital patients, dental patients, nurses, physicians, pharmaceutical workers, food workers, transportation workers, and the like. In some embodiments, one or more transmitting units 116 can transmit one or more signals 112 associated with an amount of light that is incident on one or more surfaces 106 that occur on one or more humans. Examples of such surfaces include, but are not limited to, open wounds, eyes, skin, and the like.

At operation 1006, the transmitting operation 220 may include transmitting one or more signals 112 associated with one or more instructions indicating one or more portions of one or more areas 102 where one or more sterilization units 114 are to apply one or more sterilization agents 108. In some embodiments, one or more transmitting units 116 can transmit one or more signals 112 associated with one or more instructions indicating one or more portions of one or more areas 102 where one or more sterilization units 114 are to apply one or more sterilization agents 108. In some embodiments, one or more sterilization agents 108 may be applied to one or more portions of one or more areas 102. In some embodiments, a first type of sterilization agent 108 is applied to one or more first portions of one or more areas 102 and a second type of sterilization agent 108 is applied to one or more second portions of one or more areas 102. Accordingly, different types of sterilization agents 108 may be applied to different portions of one or more areas 102. In some embodiments, activities may be conducted within one or more portions of one or more areas 102 that involve highly infective agents and/or that produce high levels of contamination within the one or more portions of the one or more areas 102. Accordingly, one or more sterilization agents 108 may be applied to those one or more portions of one or more areas 102 more frequently than to other portions of the one or more areas 102 which are not exposed to high infectivity agents or high levels of contamination. For example, one or more sterilization agents 108 may be applied to one or more benches within a laboratory more frequently than to one or more desks within the laboratory 102.

At operation 1008, the transmitting operation 220 may include transmitting one or more signals associated with one or more instructions indicating one or more portions of one or more areas 102 where the one or more sterilization units 114 are not to apply one or more sterilization agents 108. In some embodiments, one or more transmitting units 116 can transmit one or more signals 112 associated with one or more instructions indicating one or more portions of one or more areas 102 where one or more sterilization units 114 are not to apply one or more sterilization agents 108. In some embodiments, one or more sterilization agents 108 are not applied to one or more portions of one or more areas 102. For example, in some embodiments, one or more sterilization agents 108 are not applied to one or more portions of one or more areas 102 in which laboratory specimens are cultured. Examples of such areas may be found in hospital laboratories, research laboratories, tissue culture laboratories, and the like. In some embodiments, one or more types of sterilization agents 108 are not applied to one more first portions of one or more areas 102 but other types of sterilization agents 108 can be applied to the one or more first portions of the one or more areas 102. For example, in some embodiments, one or more sterilization agents 108 that would damage one or more portions of one or more areas 102 are not applied to the one or more portions of the one or more areas 102.

At operation 1010, the transmitting operation 220 may include transmitting one or more signals 112 associated with one or more instructions for one or more sterilization units 114 to apply one or more sterilization agents 108 that are identified to one or more areas 102. In some embodiments, one or more transmitting units 116 can transmit one or more signals 112 associated with one or more instructions for one or more sterilization units 114 to apply one or more sterilization agents 108 that are identified to one or more areas 102. In some embodiments, one or more areas 102 may include one or more types of contaminants that are preferably treated with one or more types of sterilization agents 108 as compared to other types of sterilization agents 108. Accordingly, in some embodiments, one or more types of sterilization agents 108 that are identified are selected for application within one or more areas 102 based on the identity of one or more contaminants for which the one or more sterilization agents 108 are to be used. In some embodiments, one or more types of sterilization agents 108 that are identified are selected for application within one or more areas 102 based on the characteristics of the one or more areas 102, the characteristics of one or more objects 104 within the one or more areas 102, the characteristics of one or more surfaces 106 within the one or more areas 102, and the like. For example, in some embodiments, one or more sterilization agents 108 that are identified are selected which will not be harmful to one or more areas 102. For example, one or more sterilization agents 108 will be selected that will not dissolve one or more objects 104 within one or more areas 102 to which the one or more sterilization agents 108 are to be applied. In some embodiments, one or more sterilization agents 108 that are identified are selected which will have greater effectiveness in sterilizing one or more areas 102. For example, a sterilization agent 108 that is a gas, such as ethylene oxide, may be applied to one or more areas 102 that are porous.

Figure 11:
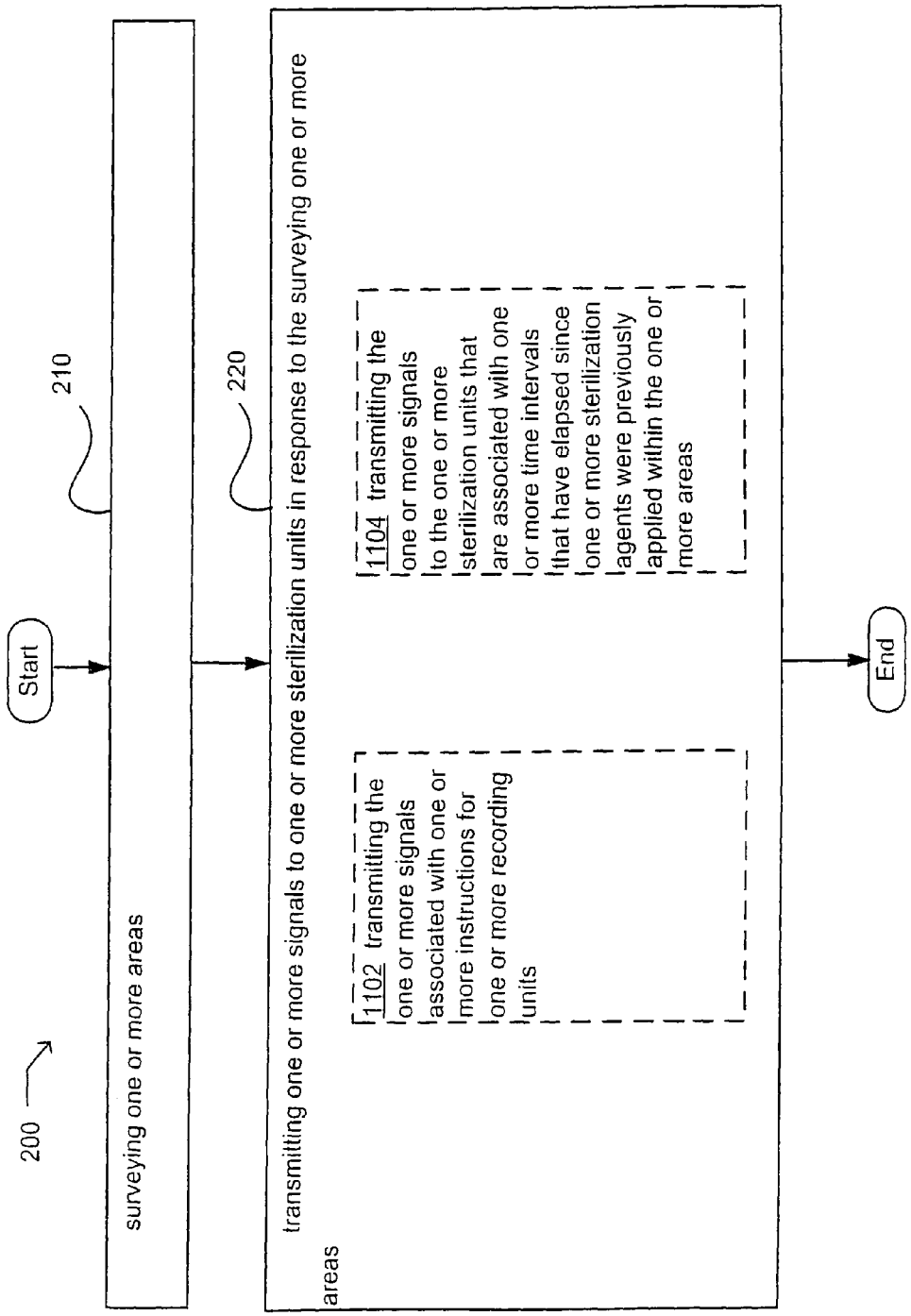
FIG. 11 illustrates an alternative embodiment of the example operation flow of FIG. 2.

FIG. 11 illustrates alternative embodiments of the example operational flow 200 of FIG. 2. FIG. 11 illustrates example embodiments where the transmitting operation 220 may include at least one additional operation. Additional operations may include an operation 1102 and/or operation 1104.

At operation 1102, the transmitting operation 220 may include transmitting one or more signals 112 associated with one or more instructions for one or more recording units 120. In some embodiments, one or more transmitting units 116 can transmit one or more signals 112 associated with one or more instructions for one or more recording units 120. In some embodiments, one or more transmitting units 116 can transmit one or more signals 112 associated with one or more sterilization protocols assigned to one or more areas 102. In some embodiments, one or more transmitting units 116 can transmit one or more signals 112 associated with one or more times when one or more areas 102 were, and/or are to be, sterilized. In some embodiments, one or more transmitting units 116 can transmit one or more signals 112 associated with the identity of one or more sterilization agents 108 that were, and/or are to be, applied to one or more areas 102. In some embodiments, one or more transmitting units 116 can transmit one or more signals 112 associated with the intensity with which one or more areas 102 were, and/or are to be, sterilized. In some embodiments, one or more transmitting units 116 can transmit one or more signals 112 associated with the frequency with which one or more areas 102 were, and/or are to be, sterilized.

At operation 1104, the transmitting operation 220 may include transmitting one or more signals 112 to one or more sterilization units 114 that are associated with one or more time intervals that have elapsed since one or more sterilization agents 108 were previously applied within one or more areas 102. In some embodiments, one or more transmitting units 116 can transmit one or more signals 112 associated with one or more time intervals that have elapsed since one or more sterilization agents 108 were previously applied within one or more areas 102. In some embodiments, the one or more signals 112 associated with one or more time intervals that have elapsed since one or more sterilization agents 108 were previously applied within one or more areas 102 can indicate that the one or more areas 102 are in compliance with one or more sterilization protocols assigned to the one or more areas 102. In some embodiments, the one or more signals 112 associated with one or more time intervals that have elapsed since one or more sterilization agents 108 were previously applied within one or more areas 102 can indicate that the one or more areas 102 are not in compliance with one or more sterilization protocols assigned to the one or more areas 102. In some embodiments, the one or more signals 112 associated with one or more time intervals that have elapsed since one or more sterilization agents 108 were previously applied within one or more areas 102 can indicate that one or more sterilization agents 108 should be applied to the one or more areas 102. In some embodiments, the one or more signals 112 associated with one or more time intervals that have elapsed since one or more sterilization agents 108 were previously applied within one or more areas 102 can indicate that one or more sterilization agents 108 should not be applied to the one or more areas 102. In some embodiments, the one or more signals 112 associated with one or more time intervals that have elapsed since one or more sterilization agents 108 were previously applied within one or more areas 102 can indicate when one or more sterilization agents 108 should be applied to the one or more areas 102. In some embodiments, the one or more signals 112 associated with one or more time intervals that have elapsed since one or more sterilization agents 108 were previously applied within one or more areas 102 can indicate what type or types of sterilization agents 108 should be applied to the one or more areas 102. In some embodiments, the one or more signals 112 associated with one or more time intervals that have elapsed since one or more sterilization agents 108 were previously applied within one or more areas 102 can indicate what type or types of sterilization agents 108 should not be applied to the one or more areas 102.

Figure 12:
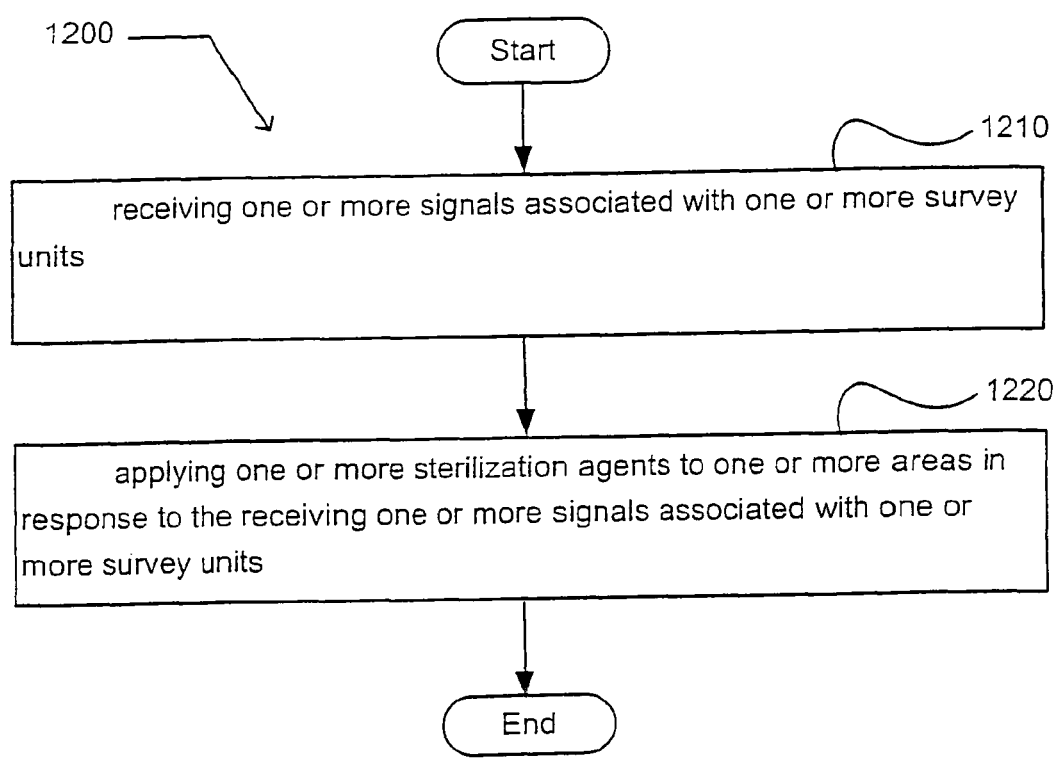
FIG. 12 illustrates an operational flow representing example operations related to sterilization methods.

FIG. 12 illustrates an operational flow 1200 representing examples of operations that are related to the performance of a sterilization method. In FIG. 12 and in following figures that include various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1200 includes an operation 1210 involving receiving one or more signals associated with one or more survey units 110. In some embodiments, one or more sterilization units 114 receive one or more signals 112 associated with one or more survey units 110. In some embodiments, one sterilization unit 114 receives one signal 112 associated with one survey unit 110. In some embodiments, one sterilization unit 114 receives one or more signals 112 associated with one survey unit 110. In some embodiments, one sterilization unit 114 receives one signal 112 associated with one or more survey units 110. In some embodiments, one sterilization unit 114 receives one or more signals 112 associated with one survey unit 110. In some embodiments, one sterilization unit 114 receives one or more signals 112 associated with one or more survey units 110. In some embodiments, one or more sterilization units 114 receive one signal 112 associated with one survey unit 110. In some embodiments, one or more sterilization units 114 receive one or more signals 112 associated with one survey unit 110. In some embodiments, one or more sterilization units 114 receive one signal 112 associated with one or more survey units 110.

The operational flow 1200 also includes an applying operation 1220 involving applying one or more sterilization agents to one or more areas in response to the receiving one or more signals associated with one or more survey units 110. In some embodiments, one or more sterilization units 114 apply one or more sterilization agents 108 to one or more areas 102 in response to receiving one or more signals 112 associated with one or more survey units 110. In some embodiments, one sterilization unit 114 applies one sterilization agent 108 to one area 102 in response to receiving one signal 112 associated with one survey unit 110. In some embodiments, one or more sterilization units 114 apply one sterilization agent 108 to one area 102 in response to receiving one signal 112 associated with one survey unit 110. In some embodiments, one or more sterilization units 114 apply one or more sterilization agents 108 to one area 102 in response to receiving one signal 112 associated with one survey unit 110. In some embodiments, one or more sterilization units 114 apply one or more sterilization agents 108 to one or more areas 102 in response to receiving one or more signals 112 associated with one survey unit 110. In some embodiments, one sterilization unit 114 applies one or more sterilization agents 108 to one or more areas 102 in response to receiving one or more signals 112 associated with one or more survey units 110. In some embodiments, one or more sterilization units 114 apply one sterilization agent 108 to one or more areas 102 in response to receiving one or more signals 112 associated with one or more survey units 114. In some embodiments, one or more sterilization units 114 apply one or more sterilization agents 108 to one area 102 in response to receiving one or more signals 112 associated with one or more survey units 110. In some embodiments, one or more sterilization units 114 apply one or more sterilization agents 108 to one or more areas 102 in response to receiving one signal 112 associated with one or more survey units 110.

Figure 13:
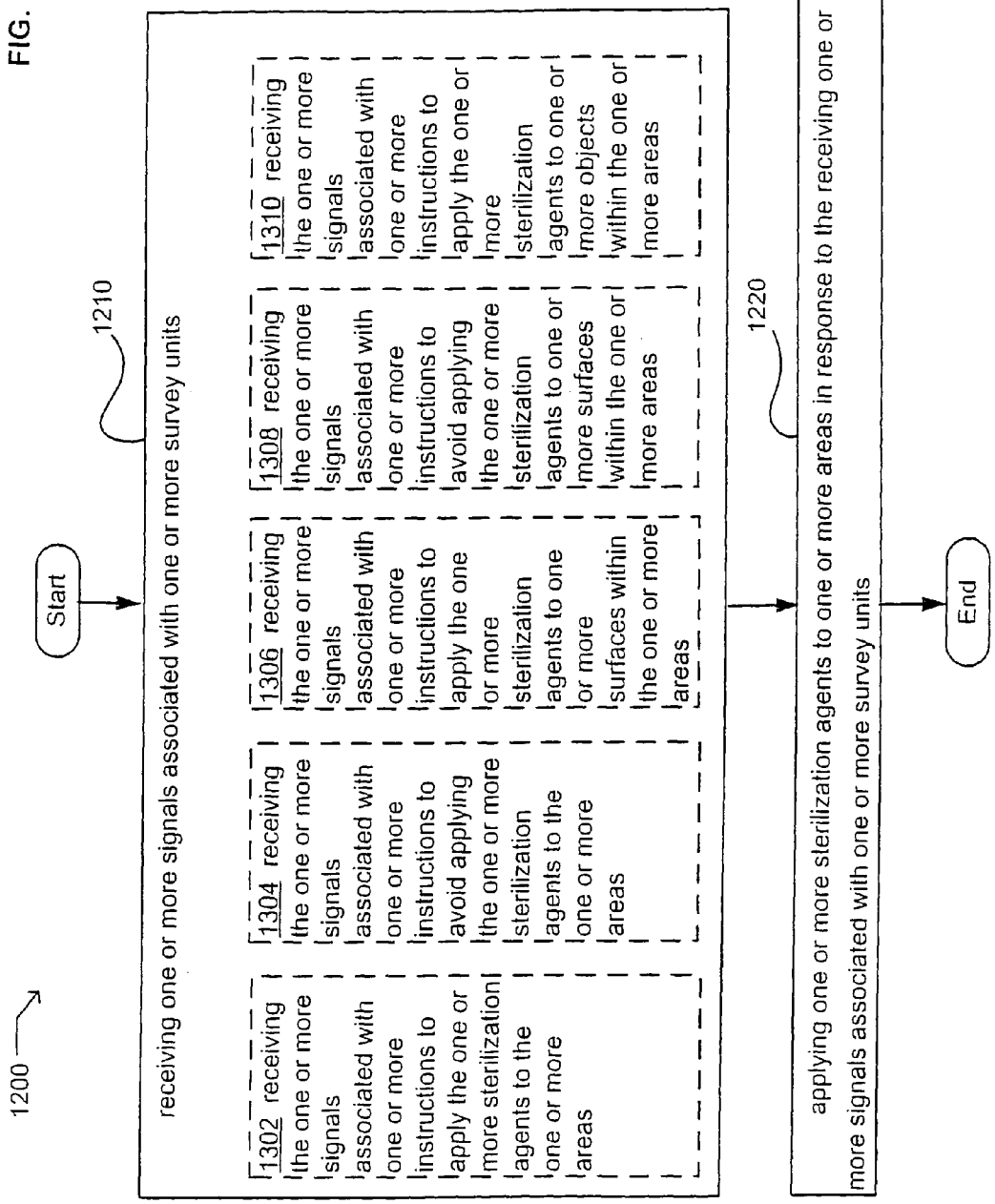
FIG. 13 illustrates an alternative embodiment of the example operation flow of FIG. 12.

FIG. 13 illustrates alternative embodiments of the example operational flow 1200 of FIG. 12. FIG. 13 illustrates example embodiments where the receiving operation 1210 may include at least one additional operation. Additional operations may include an operation 1302, operation 1304, operation 1306, operation 1308 and/or operation 1310.

At operation 1302, the receiving operation 1210 may include receiving one or more signals 112 associated with one or more instructions to apply one or more sterilization agents 108 to one or more areas 102. In some embodiments, one or more sterilization units 114 receive one or more signals 112 associated with one or more instructions to apply one or more sterilization agents 108 to one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 associated with one or more instructions for the one or more sterilization units 114 to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with one or more survey units 110 that are stationary. In some embodiments, one or more sterilization units 114 receive one or more signals 112 associated with one or more survey units 110 that are mobile. In some embodiments, one or more sterilization units 114 receive one or more signals 112 associated with prioritizing one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions for the one or more sterilization units 114 to apply one or more sterilization agents 108 that are identified to one or more areas 102. In some embodiments, one or more sterilization units 114 receive one or more signals 112 associated with one or more time intervals that have elapsed since one or more sterilization agents 108 were previously applied within one or more areas 102.

At operation 1304, the receiving operation 1210 may include receiving one or more signals 112 associated with one or more instructions to avoid applying one or more sterilization agents 108 to one or more areas 102. In some embodiments, one or more sterilization units 114 receive one or more signals 112 associated with one or more instructions to avoid applying one or more sterilization agents to one or more areas 102. The one or more signals 112 can include numerous types of information. In some embodiments, one or more sterilization units 114 receive one or more signals 112 that can include one or more instructions for the one or more sterilization units 114 to avoid applying one or more sterilization agents 108 to one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 associated with one or more instructions for the one or more sterilization units 114 to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with one or more survey units 110 that are stationary. In some embodiments, one or more sterilization units 114 receive one or more signals 112 associated with one or more survey units 110 that are mobile. In some embodiments, one or more sterilization units 114 receive one or more signals 112 associated with prioritizing one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions indicating one or more portions of one or more areas 102 where the one or more sterilization units 110 are not to apply one or more sterilization agents 108. In some embodiments, one or more sterilization units 114 receive one or more signals 112 associated with one or more time intervals that have elapsed since one or more sterilization agents 108 were previously applied within one or more areas 102.

At operation 1306, the receiving operation 1210 may include receiving one or more signals 112 associated with one or more instructions to apply one or more sterilization agents 108 to one or more surfaces 106 within one or more areas 102. In some embodiments, one or more sterilization units 114 receive one or more signals 112 associated with one or more instructions to apply one or more sterilization agents 108 to one or more surfaces 106 within one or more areas 102. The one or more signals 112 can include numerous types of information. In some embodiments, one or more sterilization units 114 receive one or more signals 112 that can include one or more instructions for the one or more sterilization units 114 to apply one or more sterilization agents 108 to one or more surfaces 106 within one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 associated with one or more instructions for the one or more sterilization units 114 to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with one or more survey units 110 that are stationary. In some embodiments, one or more sterilization units 114 receive one or more signals 112 associated with one or more survey units 110 that are mobile. In some embodiments, one or more sterilization units 114 receive one or more signals 112 associated with prioritizing one or more surfaces 106 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions for the one or more sterilization units 114 to apply one or more sterilization agents 108 that are identified to one or more surfaces 106 within one or more areas 102. In some embodiments, one or more sterilization units 114 receive one or more signals 112 associated with one or more time intervals that have elapsed since one or more sterilization agents 108 were previously applied to one or more surfaces 106 within one or more areas 102.

At operation 1308, the receiving operation 1210 may include receiving one or more signals 112 associated with one or more instructions to avoid applying one or more sterilization agents 108 to one or more surfaces 106 within one or more areas 102. In some embodiments, one or more sterilization units 114 receive one or more signals 112 associated with one or more instructions to avoid applying one or more sterilization agents 108 to one or more surfaces 106 within one or more areas 102. The one or more signals 112 can include numerous types of information. In some embodiments, one or more sterilization units 114 receive one or more signals 112 that can include one or more instructions for the one or more sterilization units 114 to avoid applying one or more sterilization agents 108 to one or more surfaces 106 within one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 associated with one or more instructions for the one or more sterilization units 114 to comply with one or more sterilization protocols. In some embodiments, one or more sterilization units 114 receive one or more signals 112 associated with one or more sterilization statuses assigned to one or more surfaces 106 within one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 that are associated with one or more survey units 110 that are stationary. In some embodiments, one or more sterilization units 114 receive one or more signals 112 that are associated with one or more survey units 110 that are mobile. In some embodiments, one or more sterilization units 114 receive one or more signals 112 associated with prioritizing one or more surfaces 106 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions for the one or more sterilization units 114 to apply one or more sterilization agents 108 that are identified to one or more surfaces 106 within one or more areas 102. In some embodiments, one or more sterilization units 114 receive one or more signals 112 associated with one or more time intervals that have elapsed since one or more sterilization agents 108 were previously applied to one or more surfaces 106 within one or more areas 102.

At operation 1310, the receiving operation 1210 may include receiving one or more signals 112 associated with one or more instructions to apply one or more sterilization agents 108 to one or more objects 104 within one or more areas 102. In some embodiments, one or more sterilization units 114 receive one or more signals 112 associated with one or more instructions to apply one or more sterilization agents 108 to one or more objects 104 within one or more areas 102. The one or more signals 112 can include numerous types of information. In some embodiments, one or more sterilization units 114 receive one or more signals 112 that can include one or more instructions for the one or more sterilization units 114 to apply one or more sterilization agents 108 to one or more objects 104 within one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 associated with one or more instructions for the one or more sterilization units 114 to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 that are associated with one or more survey units 110 that are stationary. In some embodiments, one or more sterilization units 114 receive one or more signals 112 that are associated with one or more survey units 110 that are mobile. In some embodiments, one or more sterilization units 114 receive one or more signals 112 associated with prioritizing one or more objects 104 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions for the one or more sterilization units 114 to apply one or more sterilization agents 108 that are identified to one or more objects 104 within one or more areas 102. In some embodiments, one or more sterilization units 114 receive one or more signals 112 associated with one or more time intervals that have elapsed since one or more sterilization agents 108 were previously applied within one or more areas 102.

Figure 14:
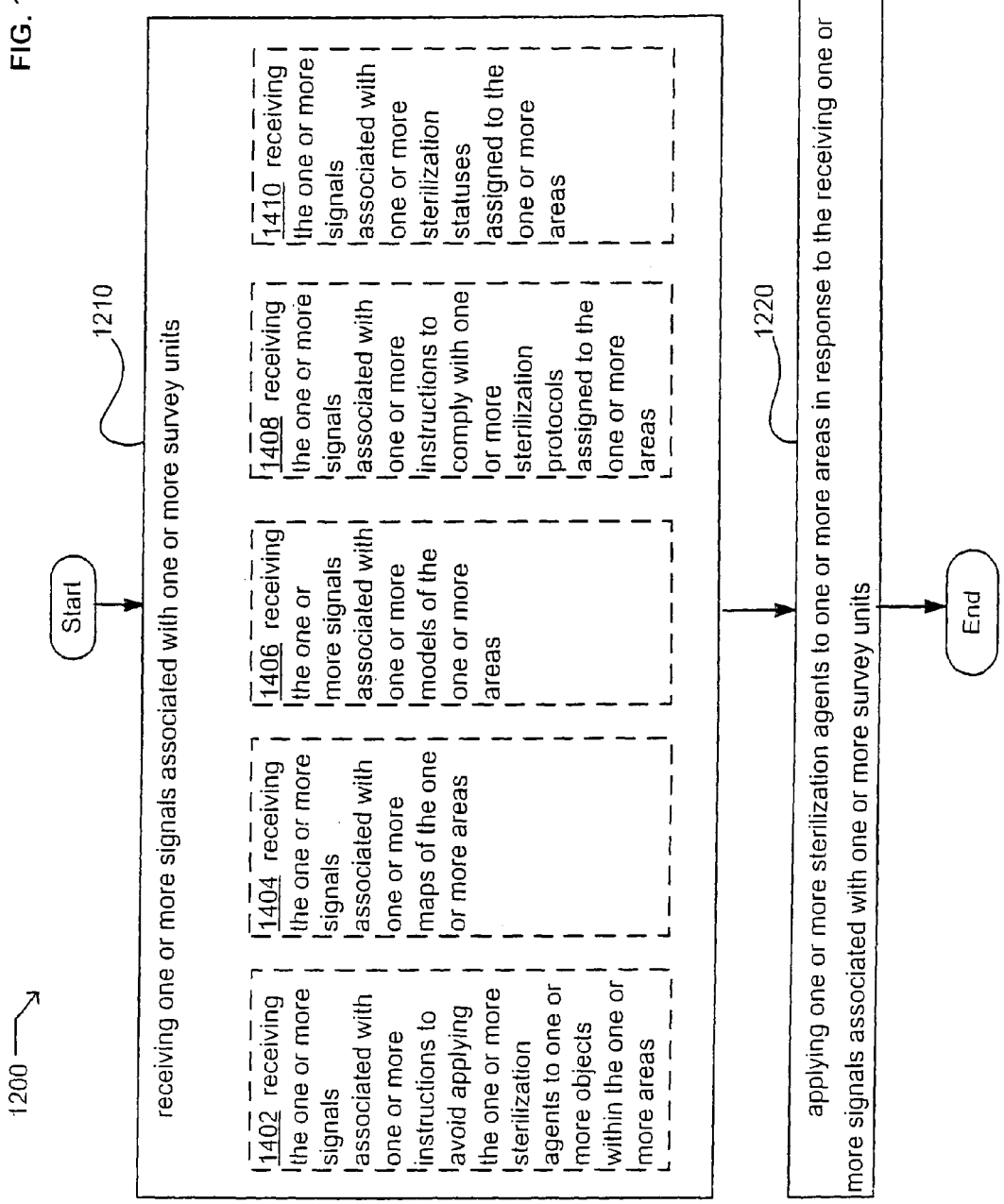
FIG. 14 illustrates an alternative embodiment of the example operation flow of FIG. 12.

FIG. 14 illustrates alternative embodiments of the example operational flow 1200 of FIG. 12. FIG. 14 illustrates example embodiments where the receiving operation 1210 may include at least one additional operation. Additional operations may include an operation 1402, operation 1404, operation 1406, operation 1408 and/or operation 1410.

At operation 1402, the receiving operation 1210 may include receiving one or more signals 112 associated with one or more instructions to avoid applying one or more sterilization agents 108 to one or more objects within one or more areas 102. In some embodiments, one or more sterilization units 114 receive one or more signals 112 associated with one or more instructions to avoid applying one or more sterilization agents 108 to one or more objects 104 within one or more areas 102. The one or more signals 112 can include numerous types of information. In some embodiments, one or more sterilization units 114 receive one or more signals 112 to avoid applying one or more sterilization agents 108 to one or more objects 104 within one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 associated with one or more instructions to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with one or more survey units 110 that are stationary. In some embodiments, one or more sterilization units 114 receive one or more signals 112 associated with one or more survey units 110 that are mobile. In some embodiments, one or more sterilization units 114 receive one or more signals 112 associated with prioritizing one or more objects 104 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions to avoid applying one or more sterilization agents 108 that are identified to one or more objects 104 within one or more areas 102. In some embodiments, one or more sterilization units 114 receive one or more signals 112 associated with one or more time intervals that have elapsed since one or more sterilization agents 108 were previously applied within one or more areas 102.

At operation 1404, the receiving operation 1210 may include receiving one or more signals 112 associated with one or more maps of one or more areas 102. In some embodiments, one or more sterilization units 114 receive one or more signals 112 associated with one or more maps of one or more areas 102. In some embodiments, one or more sterilization units 114 receive one or more signals 112 associated with the dimensions of one or more areas 102. In some embodiments, one or more sterilization units 114 receive one or more signals 112 associated with one or more positions of one or more surfaces 106 and/or one or more objects 104 within one or more areas 102. In some embodiments, one or more sterilization units 114 receive one or more signals 112 associated with the dimensions of one or more areas 102 and one or more positions of one or more surfaces 106 and/or one or more objects 104 within one or more areas 102. In some embodiments, one or more sterilization units 114 receive one or more signals 112 associated with one or more maps of one or more areas 102. The one or more signals 112 can include numerous types of information. In some embodiments, one or more sterilization units 114 receive one or more signals 112 that can include one or more instructions to apply one or more sterilization agents 108 to one or more areas 102. In some embodiments, one or more sterilization units 114 receive one or more signals 112 that can include one or more instructions to avoid applying one or more sterilization agents 108 to one or more areas 102. In some embodiments, one or more sterilization units 114 receive one or more signals 112 that can include one or more instructions to apply one or more sterilization agents 108 to one or more surfaces 106 within one or more areas 102. In some embodiments, one or more sterilization units 114 receive one or more signals 112 that can include one or more instructions to avoid applying one or more sterilization agents 108 to one or more surfaces 106 within one or more areas 102. In some embodiments, one or more sterilization units 114 receive one or more signals 112 that can include one or more instructions to apply one or more sterilization agents 108 to one or more objects 104 within one or more areas 102. In some embodiments, one or more sterilization units 114 receive one or more signals 112 that can include one or more instructions to avoid applying one or more sterilization agents 108 to one or more objects 104 within one or more areas 102. In some embodiments, one or more sterilization units 114 receive one or more signals 112 associated with one or more instructions to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with one or more survey units 110 that are stationary. In some embodiments, one or more sterilization units 114 receive one or more signals 112 associated with one or more survey units 110 that are mobile. In some embodiments, one or more sterilization units 114 receive one or more signals 112 associated with prioritizing one or more areas 102 for sterilization. In some embodiments, one or more sterilization units 114 receive one or more signals 112 associated with prioritizing one or more surfaces 106 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions indicating one or more portions of one or more areas 102 where the one or more sterilization units 114 are to apply one or more sterilization agents 108. In some embodiments, one or more sterilization units 114 receive one or more signals 112 associated with one or more instructions indicating one or more portions of one or more areas 102 where the one or more sterilization units 110 are not to apply one or more sterilization agents 108. In some embodiments, one or more sterilization units 114 receive one or more signals 112 associated with one or more instructions to apply one or more sterilization agents 108 that are identified to one or more areas 102. In some embodiments, one or more sterilization units 114 receive one or more signals 112 associated with one or more time intervals that have elapsed since one or more sterilization agents 108 were previously applied within one or more areas 102.

At operation 1406, the receiving operation 1210 may include receiving one or more signals 112 associated with one or more models of one or more areas 102. In some embodiments, one or more sterilization units 114 receive one or more signals 112 associated with one or more models of one or more areas 102. In some embodiments, one or more sterilization units 114 receive one or more signals 112 associated with the dimensions of one or more areas 102. In some embodiments, one or more sterilization units 114 receive one or more signals 112 associated with one or more positions of one or more surfaces 106 and/or one or more objects 104 within one or more areas 102. In some embodiments, one or more sterilization units 114 receive one or more signals 112 associated with the dimensions of one or more areas 102 and one or more positions of one or more surfaces 106 and/or one or more objects 104 within one or more areas 102. In some embodiments, one or more sterilization units 114 receive one or more signals 112 that can include one or more instructions to apply one or more sterilization agents 108 to one or more areas 102. In some embodiments, one or more sterilization units 114 receive one or more signals 112 that can include one or more instructions to avoid applying one or more sterilization agents 108 to one or more areas 102. In some embodiments, one or more sterilization units 114 receive one or more signals 112 that can include one or more instructions to apply one or more sterilization agents 108 to one or more surfaces 106 within one or more areas 102. In some embodiments, one or more sterilization units 114 receive one or more signals 112 that can include one or more instructions to avoid applying one or more sterilization agents 108 to one or more surfaces 106 within one or more areas 102. In some embodiments, one or more sterilization units 114 receive one or more signals 112 that can include one or more instructions to apply one or more sterilization agents 108 to one or more objects 104 within one or more areas 102. In some embodiments, one or more sterilization units 114 receive one or more signals 112 that can include one or more instructions to avoid applying one or more sterilization agents 108 to one or more objects 104 within one or more areas 102. In some embodiments, one or more sterilization units 114 receive one or more signals 112 associated with one or more instructions to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with one or more survey units 110 that are stationary. In some embodiments, one or more sterilization units 114 receive one or more signals 112 associated with one or more survey units 110 that are mobile. In some embodiments, one or more sterilization units 114 receive one or more signals 112 associated with prioritizing one or more areas 102 for sterilization. In some embodiments, one or more sterilization units 114 receive one or more signals 112 associated with prioritizing one or more surfaces 106 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions indicating one or more portions of one or more areas 102 to apply one or more sterilization agents 108. In some embodiments, one or more sterilization units 114 receive one or more signals 112 associated with one or more instructions indicating one or more portions of one or more areas 102 not to apply one or more sterilization agents 108. In some embodiments, one or more sterilization units 114 receive one or more signals 112 associated with one or more instructions to apply one or more sterilization agents 108 that are identified to one or more areas 102. In some embodiments, one or more sterilization units 114 receive one or more signals 112 associated with one or more time intervals that have elapsed since one or more sterilization agents 108 were previously applied within one or more areas 102.

At operation 1408, the receiving operation 1210 may include receiving one or more signals 112 associated with one or more instructions to comply with one or more sterilization protocols assigned to one or more areas 102. In some embodiments, one or more sterilization units 114 receive one or more signals 112 associated with one or more instructions to comply with one or more sterilization protocols. In some embodiments, one or more sterilization protocols may be assigned to one or more areas 102. In some embodiments, a sterilization protocol may specify the immediacy, latency, intensity and time-integrated intensity of sterilizing radiation that is to be applied within one or more areas 102 as a function of either relative or absolute location within the one or more areas 102. In some embodiments, a sterilization protocol may specify one or more types of sterilization agents 108 that are to be applied to one or more areas 102. In some embodiments, a sterilization protocol may specify one or more types of sterilization agents 108 that are not to be applied to one or more areas 102. In some embodiments, a sterilization protocol may specify the frequency with which one or more sterilization agents 108 are to be applied to one or more areas 102. In some embodiments, a sterilization protocol may specify the intensity and/or concentration that one or more types of sterilization agents 108 are to be applied to one or more areas 102. Numerous sterilization protocols can be assigned to one or more areas 102. In some embodiments, such protocols can be used to specify the intensity with which one or more areas 102 are sterilized to account for high patient-hazard and/or high infectivity likelihood areas to ensure that such areas 102 receive rigorous and/or frequent sterilization treatment. In some embodiments, one or more sterilization units 114 receive one or more signals 112 associated with how much time has passed since one or more areas 102 were last sterilized. In some embodiments, one or more sterilization units 114 receive one or more signals 112 associated with determining if one or more areas 102 are in compliance with one or more protocols that call for sterilization of the one or more areas 102 at given time intervals.

At operation 1410, the receiving operation 1210 may include receiving one or more signals 112 associated with one or more sterilization statuses assigned to one or more areas 102. In some embodiments, one or more sterilization units 114 receive one or more signals 112 associated with one or more sterilization statuses assigned to one or more areas 102. In some embodiments, the sterilization status of one or more areas 102 can be relative to one or more sterilization levels assigned to the one or more areas 102. For example, some areas 102 may be assigned a very high sterilization level where very high levels of sterility are desired. Examples of areas 102 where a very high level of sterility may be desired include, but are not limited to, hospital operating rooms, pharmaceutical packaging facilities, food packaging facilities, nude mouse facilities, hospital wards, and the like. In other examples, areas 102 where the levels of sterility may not need to be as high can be assigned a lower sterilization level. In some embodiments, one or more sterilization levels that are assigned to one or more areas 102 may include parameters for time of sterilization, frequency of sterilization, type of sterilization agent 108 to be applied, intensity of sterilization, use of multiple sterilization agents 108, risk-level assigned to one or more areas 102, types of contamination occurring within one or more areas 102, disease-state of one or more patients within one or more areas 102, and the like. In some embodiments, one or more sterilization units 114 receive one or more signals 112 associated with one or more sterilization statuses of one or more areas 102 which indicate if the one or more areas 102 need to be sterilized or whether the one or more areas 102 satisfy the desired sterilization level. In some embodiments, one or more sterilization units 114 receive one or more signals 112 associated with determining when one or more areas 102 that are currently sterile should be sterilized again. In some embodiments, one or more sterilization units 114 receive one or more signals 112 associated with one or more instructions indicating when to sterilize one or more areas 102. In some embodiments, one or more sterilization units 114 receive one or more signals 112 associated with determining if one or more sterilization levels assigned to one or more areas 102 have changed and whether the one or more areas 102 satisfy the one or more newly assigned sterilization levels.

Figure 15:
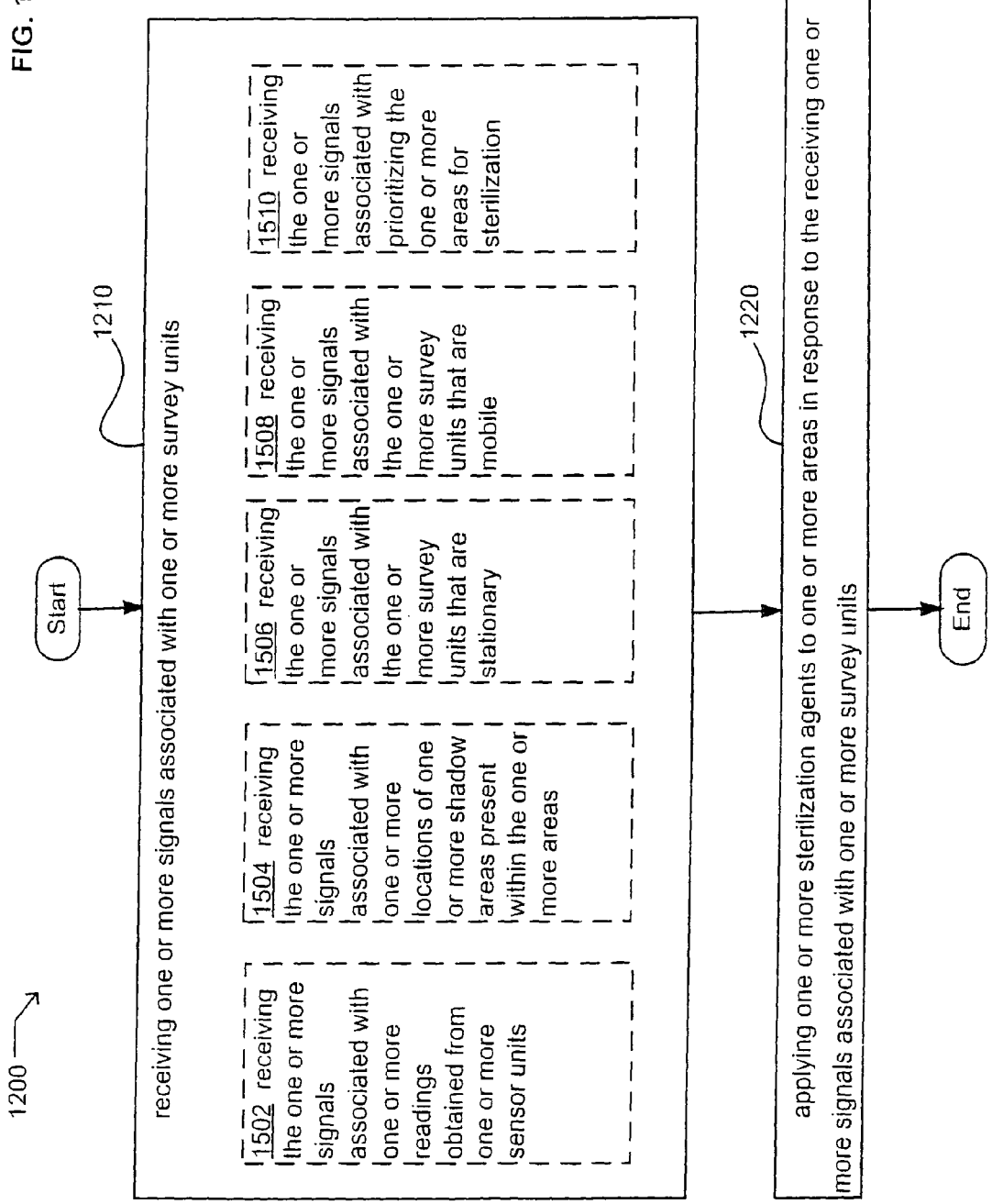
FIG. 15 illustrates an alternative embodiment of the example operation flow of FIG. 12.

FIG. 15 illustrates alternative embodiments of the example operational flow 1200 of FIG. 12. FIG. 15 illustrates example embodiments where the receiving operation 1210 may include at least one additional operation. Additional operations may include an operation 1502, operation 1504, operation 1506, operation 1508 and/or operation 1510.

At operation 1502, the receiving operation 1210 may include receiving one or more signals 112 associated with one or more readings obtained from one or more sensor units 118. In some embodiments, one or more sterilization units 114 receive one or more signals 112 associated with one or more readings obtained from one or more sensor units 118. In some embodiments, one or more sterilization units 114 receive one or more signals 112 associated with one or more times when one or more areas 102 were sterilized. In some embodiments, one or more sterilization units 114 receive one or more signals 112 associated with how often one or more areas 102 are sterilized. In some embodiments, one or more sterilization units 114 receive one or more signals 112 associated with the intensity with which one or more areas 102 are sterilized. In some embodiments, one or more sterilization units 114 receive one or more signals 112 associated with whether or not one or more surfaces 106 within one or more areas 102 have been sterilized. In some embodiments, one or more sterilization units 114 receive one or more signals 112 associated with one or more types of sterilization agents 108 that have been applied within one or more areas 102. In some embodiments, one or more sterilization units 114 receive one or more signals 112 associated with one or more types of sterilization agents 108 that have been applied to one or more surfaces 106 within one or more areas 102. In some embodiments, one or more sterilization units 114 receive one or more signals 112 associated with one or more types of sterilization agents 108 that have been applied to one or more objects 104 within one or more areas 102. In some embodiments, one or more sterilization units 114 receive one or more signals 112 associated with one or more types of sterilization agents 108 that have been applied to one or more objects 104 and/or one or more surfaces 106 within one or more areas 102.

At operation 1504, the receiving operation 1210 may include receiving one or more signals 112 associated with one or more locations of one or more shadow areas present within one or more areas 102. In some embodiments, one or more sterilization units 114 receive one or more signals 112 associated with one or more locations of one or more shadow areas present within one or more areas 102. In some embodiments, shadow areas may occur when radiation is blocked from reaching one or more shadow areas by one or more objects 104 positioned between one or more sterilization units 114 that emit radiation and the one or more shadow areas. In some embodiments, one or more sterilization units 114 receive one or more signals 112 associated with assigning non-sterile status to one or more shadow areas. In some embodiments, one or more sterilization units 114 receive one or more signals 112 associated with instructing the one or more sterilization units 114 to sterilize one or more shadow areas.

At operation 1506, the receiving operation 1210 may include receiving one or more signals 112 associated with one or more survey units 110 that are stationary. In some embodiments, one or more sterilization units 114 receive one or more signals 112 associated with one or more survey units 110 that are stationary. The one or more signals 112 can include numerous types of information. In some embodiments, one or more sterilization units 114 receive one or more signals 112 that can include one or more instructions to apply one or more sterilization agents 108 to one or more areas 102. In some embodiments, one or more sterilization units 114 receive one or more signals 112 that can include one or more instructions to avoid applying one or more sterilization agents 108 to one or more areas 102. In some embodiments, one or more sterilization units 114 receive one or more signals 112 that can include one or more instructions to apply one or more sterilization agents 108 to one or more surfaces 106 within one or more areas 102. In some embodiments, one or more sterilization units 114 receive one or more signals 112 that can include one or more instructions to avoid applying one or more sterilization agents 108 to one or more surfaces 106 within one or more areas 102. In some embodiments, one or more sterilization units 114 receive one or more signals 112 that can include one or more instructions to apply one or more sterilization agents 108 to one or more objects 104 within one or more areas 102. In some embodiments, one or more sterilization units 114 receive one or more signals 112 that can include one or more instructions to avoid applying one or more sterilization agents 108 to one or more objects 104 within one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 that are associated with one or more instructions to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with prioritizing one or more areas 102 for sterilization. In some embodiments, one or more sterilization units 114 receive one or more signals 112 associated with prioritizing one or more surfaces 106 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions indicating one or more portions of one or more areas 102 to apply one or more sterilization agents 108. In some embodiments, one or more sterilization units 114 receive one or more signals 112 associated with one or more instructions indicating one or more portions of one or more areas 102 to apply one or more sterilization agents 108. In some embodiments, one or more sterilization units 114 receive one or more signals 112 associated with one or more instructions to apply one or more sterilization agents 108 that are identified to one or more areas 102. In some embodiments, one or more sterilization units 114 receive one or more signals 112 associated with one or more time intervals that have elapsed since one or more sterilization agents 108 were previously applied within one or more areas 102.

At operation 1508, the receiving operation 1210 may include receiving one or more signals 112 associated with one or more survey units 110 that are mobile. In some embodiments, one or more sterilization units 114 receive one or more signals 112 associated with one or more survey units 110 that are mobile. The one or more signals 112 can include numerous types of information. In some embodiments, one or more sterilization units 114 receive one or more signals 112 that can include one or more instructions to apply one or more sterilization agents 108 to one or more areas 102. In some embodiments, one or more sterilization units 114 receive one or more signals 112 that can include one or more instructions to avoid applying one or more sterilization agents 108 to one or more areas 102. In some embodiments, one or more sterilization units 114 receive one or more signals 112 that can include one or more instructions to apply one or more sterilization agents 108 to one or more surfaces 106 within one or more areas 102. In some embodiments, one or more sterilization units 114 receive one or more signals 112 that can include one or more instructions to avoid applying one or more sterilization agents 108 to one or more surfaces 106 within one or more areas 102. In some embodiments, one or more sterilization units 114 receive one or more signals 112 that can include one or more instructions to apply one or more sterilization agents 108 to one or more objects 104 within one or more areas 102. In some embodiments, one or more sterilization units 114 receive one or more signals 112 that can include one or more instructions to avoid applying one or more sterilization agents 108 to one or more objects 104 within one or more areas 102. In some embodiments, one or more sterilization units 114 receive one or more signals 112 associated with one or more maps of one or more areas 102. In some embodiments, one or more sterilization units 114 receive one or more signals 112 associated with one or more models of one or more areas 102. In some embodiments, one or more sterilization units 114 receive one or more signals 112 that are associated with one or more instructions to comply with one or more sterilization protocols. In some embodiments, one or more sterilization units 114 receive one or more signals 112 associated with one or more sterilization statuses assigned to one or more areas 102. In some embodiments, one or more sterilization units 114 receive one or more signals 112 associated with one or more readings obtained from one or more sensor units 118. In some embodiments, one or more sterilization units 114 receive one or more signals 112 associated with one or more locations of one or more shadow areas present within one or more areas 102. In some embodiments, one or more sterilization units 114 receive one or more signals 112 associated with prioritizing one or more areas 102 for sterilization. In some embodiments, one or more sterilization units 114 receive one or more signals 112 associated with prioritizing one or more surfaces 106 within one or more areas 102 for sterilization. In some embodiments, one or more sterilization units 114 receive one or more signals 112 associated with one or more humans that are present or absent within one or more areas 102. In some embodiments, one or more sterilization units 114 receive one or more signals 112 associated with one or more instructions indicating one or more portions of one or more areas 102 to apply one or more sterilization agents 108. In some embodiments, one or more sterilization units 114 receive one or more signals 112 associated with one or more instructions indicating one or more portions of one or more areas 102 to apply one or more sterilization agents 108. In some embodiments, one or more sterilization units 114 receive one or more signals 112 associated with one or more instructions to apply one or more sterilization agents 108 that are identified to one or more areas 102. In some embodiments, one or more sterilization units 114 receive one or more signals 112 associated with one or more time intervals that have elapsed since one or more sterilization agents 108 were previously applied within one or more areas 102.

At operation 1510, the receiving operation 1210 may include receiving one or more signals associated with prioritizing one or more areas 102 for sterilization. In some embodiments, one or more sterilization units 114 receive one or more signals 112 associated with prioritizing one or more areas 102 for sterilization. In some embodiments, one or more sterilization units 114 receive one or more signals 112 associated with the need for sterilization of the one or more areas 102. For example, an operating room may be sterilized before other areas 102 due to the existence of an emergency surgery that is to be done within the operating room. In some embodiments, one or more sterilization units 114 receive one or more signals 112 associated the presence of a highly infectious agent within one or more areas 102. For example, an examination room in a hospital may be sterilized before other areas 102 due to the presence of a patient who is infected with smallpox within the examination room. In some embodiments, one or more sterilization units 114 receive one or more signals 112 associated with conformance with a sterilization protocol.

Figure 16:
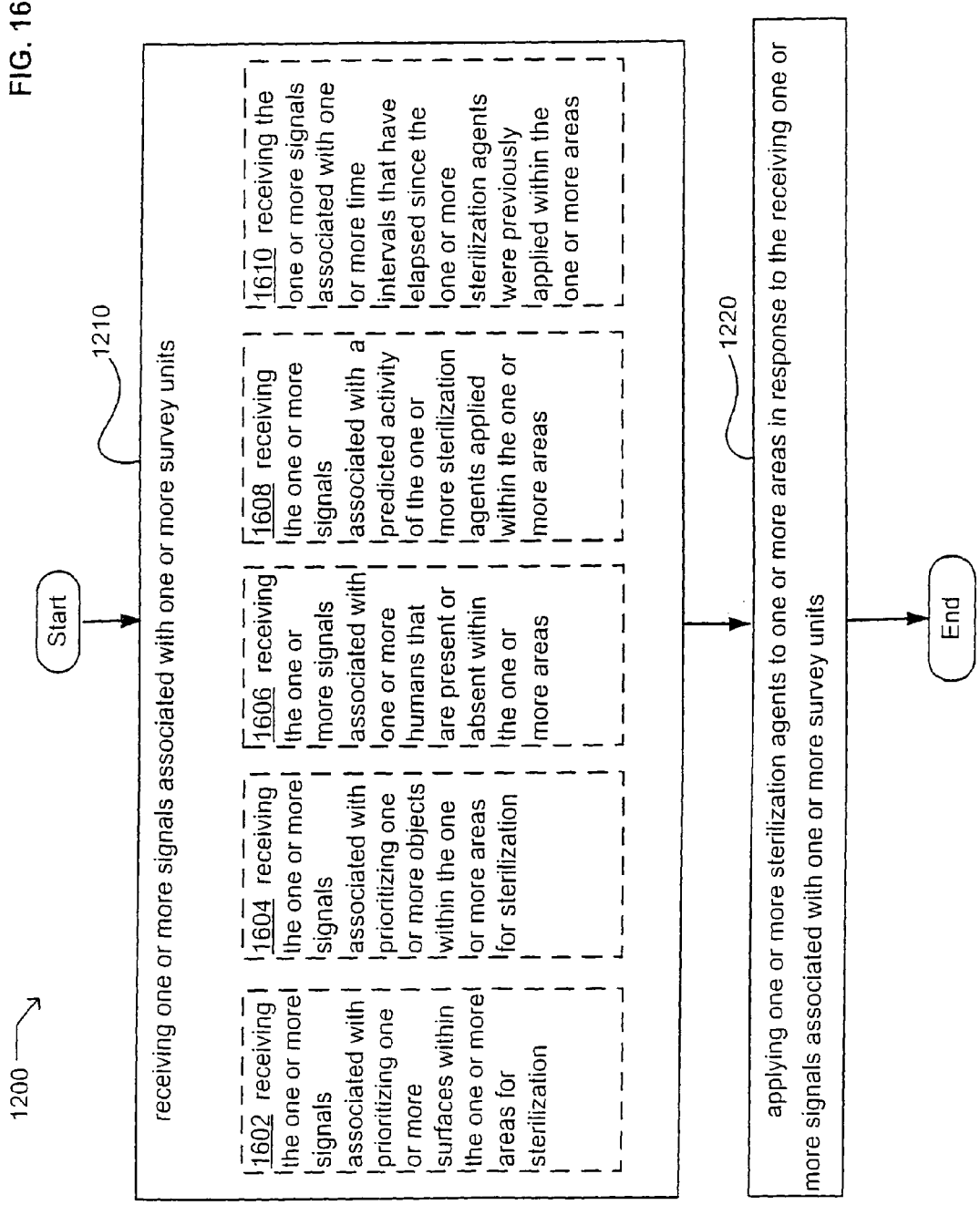
FIG. 16 illustrates an alternative embodiment of the example operation flow of FIG. 12.

FIG. 16 illustrates alternative embodiments of the example operational flow 1200 of FIG. 12. FIG. 16 illustrates example embodiments where the receiving operation 1210 may include at least one additional operation. Additional operations may include an operation 1602, operation 1604, operation 1606, operation 1608 and/or operation 1610.

At operation 1602, the receiving operation 1210 may include receiving one or more signals 112 associated with prioritizing one or more surfaces within one or more areas 102 for sterilization. In some embodiments, one or more sterilization units 114 receive one or more signals 112 associated with prioritizing one or more surfaces 106 within one or more areas 102 for sterilization. In some embodiments, one or more sterilization units 114 receive one or more signals 112 associated with the need for sterilization of one or more surfaces 106 within one or more areas 102. For example, one or more surfaces 106 within an operating room may be sterilized before other areas 102 due to the existence of an emergency surgery that is to be done within the operating room. In some embodiments, one or more sterilization units 114 receive one or more signals 112 associated with the presence of a highly infectious agent within or on one or more surfaces 106 within one or more areas 102. For example, one or more surfaces 106 within an examination room in a hospital may be sterilized before other areas 102 due to the presence of a patient who is infected with smallpox within the examination room. In some embodiments, one or more sterilization units 114 receive one or more signals 112 associated with conformance with a sterilization protocol.

At operation 1604, the receiving operation 1210 may include receiving one or more signals 112 associated with prioritizing one or more objects 104 within one or more areas 102 for sterilization. In some embodiments, one or more sterilization units 114 receive one or more signals 112 associated with prioritizing one or more objects 104 within one or more areas 102 for sterilization. In some embodiments, one or more sterilization units 114 receive one or more signals 112 associated with the need for sterilization of one or more objects 104 within one or more areas 102. For example, one or more objects 104, such as surgical instruments, may be sterilized substantially immediately due to the existence of an emergency surgery that is to be done with the surgical instruments. In some embodiments, one or more sterilization units 114 receive one or more signals 112 associated with the presence of a highly infectious agent on one or more objects 104. For example, one or more objects 104 within a hospital may be sterilized before other objects 104 due to use of the objects 104 to treat a patient who is infected with smallpox. In some embodiments, one or more sterilization units 114 receive one or more signals 112 associated with conformance with a sterilization protocol.

At operation 1606, the receiving operation 1210 may include receiving one or more signals 112 associated with one or more humans that are present or absent within one or more areas 102. In some embodiments, one or more sterilization units 114 receive one or more signals 112 associated with one or more humans that are present or absent within one or more areas 102. In some embodiments, one or more sterilization units 114 receive one or more signals 112 associated with an amount of radiation, such as ultraviolet light, to which one or more humans have been exposed. In some embodiments, one or more sterilization units 114 receive one or more signals 112 associated with an amount of radiation, such as ultraviolet light, to which one or more humans have been exposed through reflection of the radiation onto the one or more humans. Examples of such humans include, but are not limited to, hospital patients, dental patients, nurses, physicians, pharmaceutical workers, food workers, transportation workers, and the like. In some embodiments, one or more sterilization units 114 receive one or more signals 112 associated with an amount of light that is incident on one or more surfaces 106 that occur on one or more humans. Examples of such surfaces include, but are not limited to, open wounds, eyes, skin, and the like.

At operation 1608, the receiving operation 1210 may include receiving one or more signals 112 associated with a predicted activity of one or more sterilization agents 108 applied within one or more areas 102. In some embodiments, one or more sterilization units 114 receive one or more signals 112 associated with a predicted activity of one or more sterilization agents 108 applied within one or more areas 102. In some embodiments, one or more sterilization units 114 receive one or more signals 112 associated with one or more survey units 110 that can predict the activity of one or more sterilization agents 108 that are applied within one or more areas 102. In some embodiments, one or more survey units 110 can utilize the identity, concentration, time of application, and/or substantially any combination thereof of one or more sterilization agents 108 to be applied to one or more areas 102 to predict the activity of the one or more sterilization agents 108 on one or more types of contamination that may or may not be present within the one or more areas 102. In some embodiments, the identity, concentration, time of application, and/or substantially any combination thereof, of one or more sterilization agents 108 to one or more areas 102 may be determined by one or more survey units 110. In some embodiments, the one or more sterilizing agents 108 were previously applied within the one or more areas 102 by one or more sterilization units 114.

At operation 1610, the receiving operation 1210 may include receiving one or more signals 112 associated with one or more time intervals that have elapsed since one or more sterilization agents 108 were previously applied within one or more areas 102. In some embodiments, one or more sterilization units 114 receive one or more signals 112 associated with one or more time intervals that have elapsed since one or more sterilization agents 108 were previously applied within one or more areas 102. In some embodiments, the one or more signals 112 associated with one or more time intervals that have elapsed since one or more sterilization agents 108 were previously applied within one or more areas 102 can indicate that the one or more areas 102 are in compliance with one or more sterilization protocols assigned to the one or more areas 102. In some embodiments, the one or more signals 112 associated with one or more time intervals that have elapsed since one or more sterilization agents 108 were previously applied within one or more areas 102 can indicate that the one or more areas 102 are not in compliance with one or more sterilization protocols assigned to the one or more areas 102. In some embodiments, the one or more signals 112 associated with one or more time intervals that have elapsed since one or more sterilization agents 108 were previously applied within one or more areas 102 can indicate that one or more sterilization agents 108 should be applied to the one or more areas 102. In some embodiments, the one or more signals 112 associated with one or more time intervals that have elapsed since one or more sterilization agents 108 were previously applied within one or more areas 102 can indicate that one or more sterilization agents 108 should not be applied to the one or more areas 102. In some embodiments, the one or more signals 112 associated with one or more time intervals that have elapsed since one or more sterilization agents 108 were previously applied within one or more areas 102 can indicate when one or more sterilization agents 108 should be applied to the one or more areas 102. In some embodiments, the one or more signals 112 associated with one or more time intervals that have elapsed since one or more sterilization agents 108 were previously applied within one or more areas 102 can indicate what type or types of sterilization agents 108 should be applied to the one or more areas 102. In some embodiments, the one or more signals 112 associated with one or more time intervals that have elapsed since one or more sterilization agents 108 were previously applied within one or more areas 102 can indicate what type or types of sterilization agents 108 should not be applied to the one or more areas 102. In some embodiments, the one or more sterilizing agents 108 were previously applied within the one or more areas 102 by one or more sterilization units 114.

Figure 17:
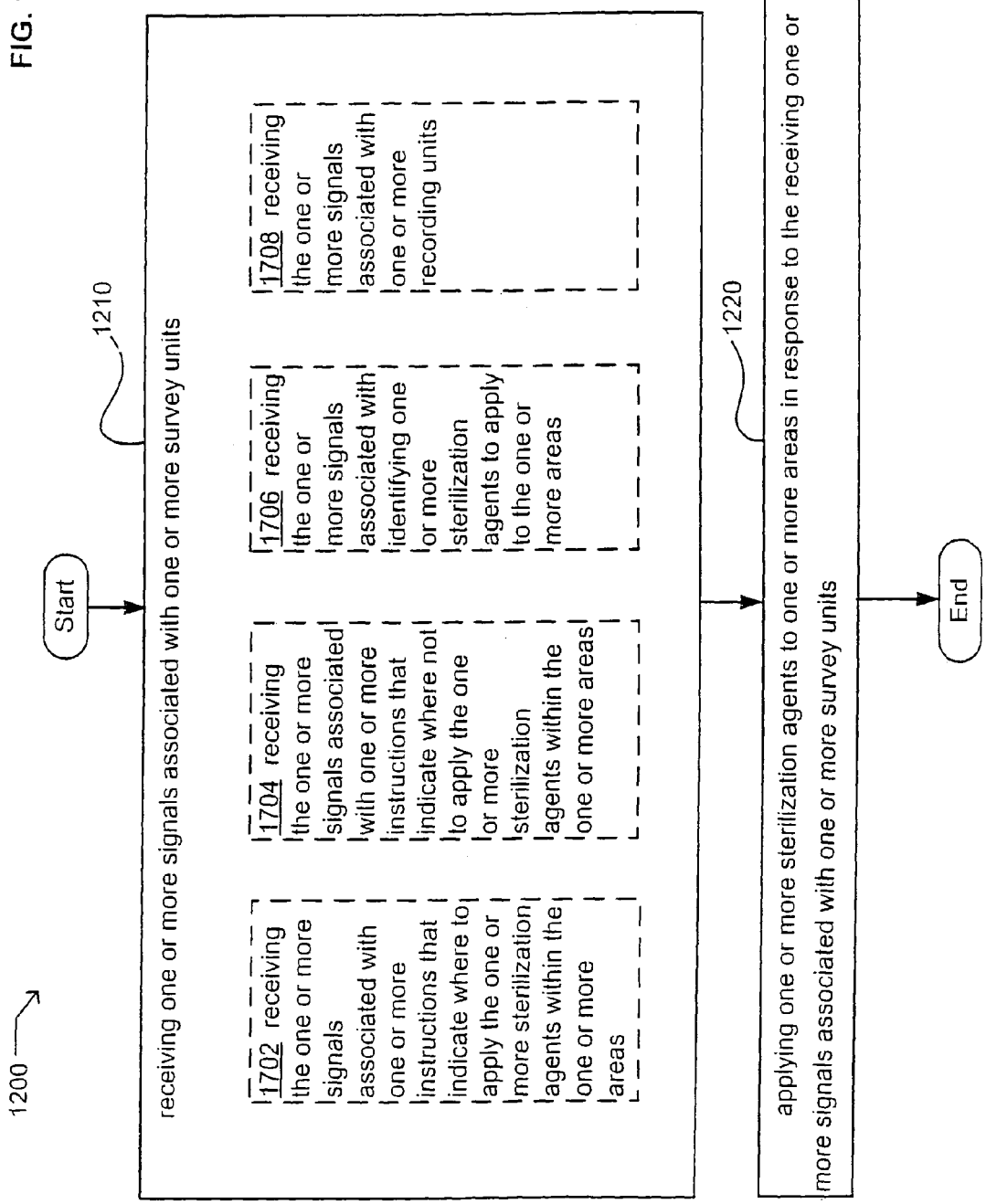
FIG. 17 illustrates an alternative embodiment of the example operation flow of FIG. 12.

FIG. 17 illustrates alternative embodiments of the example operational flow 1200 of FIG. 12. FIG. 17 illustrates example embodiments where the receiving operation 1210 may include at least one additional operation. Additional operations may include an operation 1702, operation 1704, operation 1706 and/or operation 1708.

At operation 1702, the receiving operation 1210 may include receiving one or more signals 112 associated with one or more instructions that indicate where to apply one or more sterilization agents 108 within one or more areas 102. In some embodiments, one or more sterilization units 114 can receive one or more signals 112 associated with one or more instructions that indicate where to apply one or more sterilization agents 108 within one or more areas 102. In some embodiments, one or more sterilization units 114 can receive one or more signals 112 associated with one or more instructions that indicate one or more portions of one or more areas 102 where one or more sterilization agents 108 are to be applied. In some embodiments, one or more sterilization units 114 can receive one or more signals 112 associated with one or more instructions indicating that one or more sterilization agents 108 may be applied to one or more portions of one or more areas 102. In some embodiments, one or more sterilization units 114 can receive one or more signals 112 associated with one or more instructions indicating that a first type of sterilization agent 108 can be applied to one or more first portions of one or more areas 102 and a second type of sterilization agent 108 can be applied to one or more second portions of one or more areas 102. Accordingly, different types of sterilization agents 108 may be applied to different portions of one or more areas 102.

At operation 1704, the receiving operation 1210 may include receiving one or more signals 112 associated with one or more instructions that indicate where not to apply one or more sterilization agents 108 within one or more areas 102. In some embodiments, one or more sterilization units 114 can receive one or more signals 112 associated with one or more instructions that indicate where not to apply one or more sterilization agents 108 within one or more areas 102. In some embodiments, one or more sterilization units 114 can receive one or more signals 112 associated with one or more instructions indicating one or more portions of one or more areas 102 where one or more sterilization agents 108 should not be applied. For example, in some embodiments, one or more sterilization agents 108 should not to be applied to one or more portions of one or more areas 102 in which laboratory specimens are cultured. Examples of such areas may be found in hospital laboratories, research laboratories, tissue culture laboratories, and the like. In some embodiments, one or more sterilization agents 108 that would damage one or more portions of one or more areas 102 should not be applied to the one or more portions of the one or more areas 102.

At operation 1706, the receiving operation 1210 may include receiving one or more signals 112 associated with identifying one or more sterilization agents 108 to apply to one or more areas 102. In some embodiments, one or more sterilization units 114 can receive one or more signals 112 associated with identifying one or more sterilization agents 108 to apply to one or more areas 102. In some embodiments, one or more sterilization units 114 can receive one or more signals 112 associated with one or more instructions to apply one or more sterilization agents 108 that are identified to one or more areas 102. In some embodiments, one or more areas 102 may include one or more types of contaminants that are preferably treated with one or more types of sterilization agents 108 as compared to other types of sterilization agents 108. Accordingly, in some embodiments, one or more types of sterilization agents 108 that are identified are selected for application within one or more areas 102 based on the identity of one or more contaminants for which the one or more sterilization agents 108 are to be used. In some embodiments, one or more types of sterilization agents 108 that are identified are selected for application within one or more areas 102 based on characteristics of the one or more areas 102, characteristics of one or more objects 104 within the one or more areas 102, characteristics of one or more surfaces 106 within the one or more areas 102, and the like. For example, in some embodiments, one or more sterilization units 114 can receive more signals 112 associated with one or more sterilization agents 108 that will not harm one or more areas 102. For example, one or more sterilization agents 108 may be selected that will not dissolve one or more objects 104 within one or more areas 102 to which one or more sterilization agents 108 are to be applied. In some embodiments, one or more sterilization units 114 can receive more signals 112 associated with one or more sterilization agents 108 which may have greater effectiveness in sterilizing one or more areas 102. For example, a sterilization agent 108 that is a gas, such as ethylene oxide, may be applied to one or more areas 102 that are porous.

At operation 1708, the receiving operation 1210 may include receiving one or more signals 112 associated with one or more recording units 120. In some embodiments, one or more sterilization units 114 can receive one or more signals 112 associated with one or more recording units 120. In some embodiments, one or more sterilization units 114 can receive one or more signals 112 associated with one or more sterilization protocols assigned to one or more areas 102. In some embodiments, one or more sterilization units 114 can receive one or more signals 112 associated with one or more times when one or more areas 102 were, and/or are to be, sterilized. In some embodiments, one or more sterilization units 114 can receive one or more signals 112 associated with the identity of one or more sterilization agents 108 that were, and/or are to be, applied to one or more areas 102. In some embodiments, one or more sterilization units 114 can receive one or more signals 112 associated with the intensity with which one or more areas 102 were, and/or are to be, sterilized. In some embodiments, one or more sterilization units 114 can receive one or more signals 112 associated with the frequency with which one or more areas 102 were, and/or are to be, sterilized.

Figure 18:
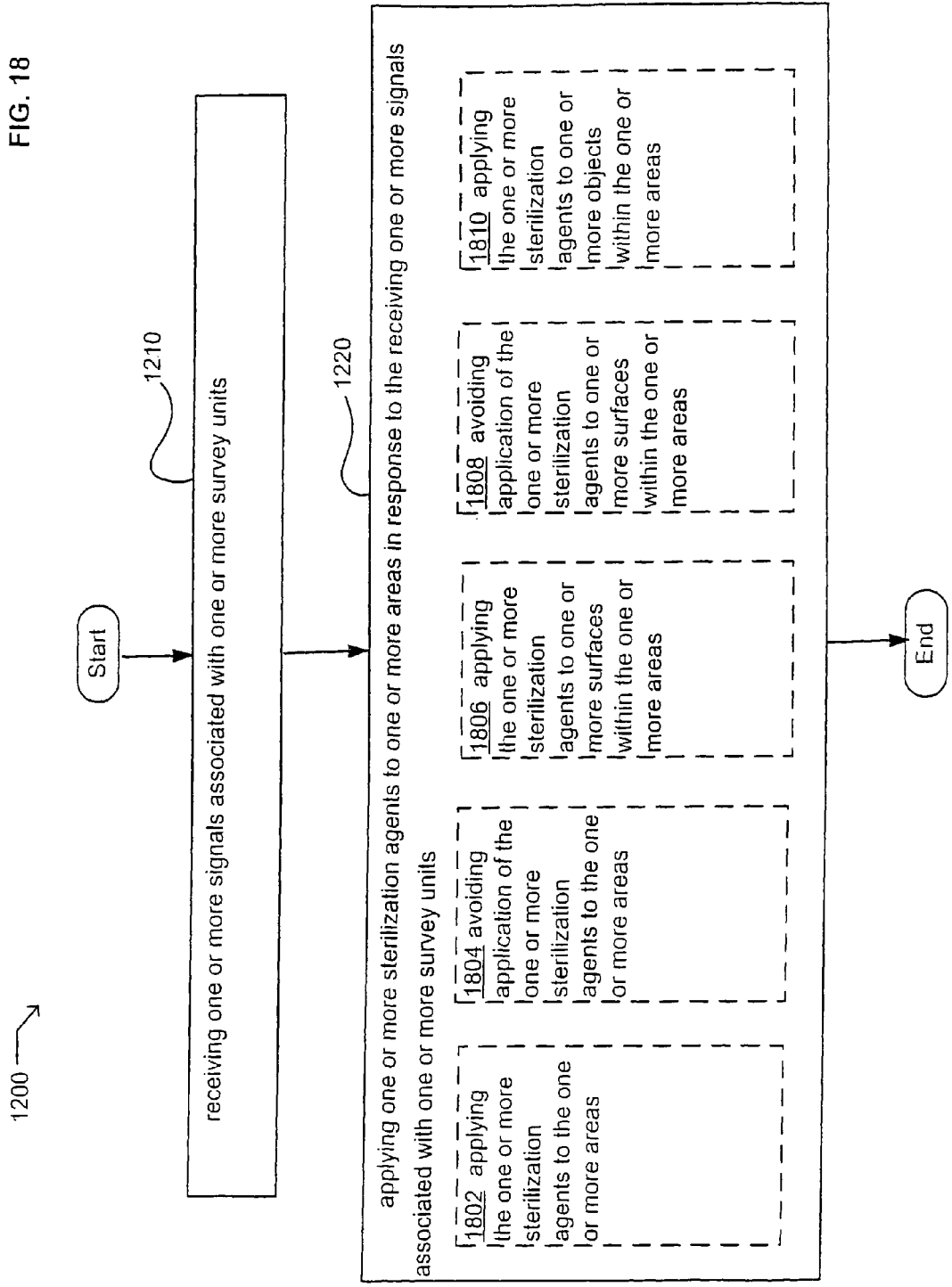
FIG. 18 illustrates an alternative embodiment of the example operation flow of FIG. 12.

FIG. 18 illustrates alternative embodiments of the example operational flow 1200 of FIG. 12. FIG. 18 illustrates example embodiments where the applying operation 1220 may include at least one additional operation. Additional operations may include an operation 1802, operation 1804, operation 1806, operation 1808 and/or operation 1810.

At operation 1802, the applying operation 1220 may include applying one or more sterilization agents 108 to one or more areas 102. In some embodiments, one or more sterilization units 114 may apply one or more sterilization agents 108 to one or more areas 102. In some embodiments, one or more sterilization units 114 may apply one or more sterilization agents 108 to one or more areas 102 according to one or more maps of the one or more areas 102. In some embodiments, one or more sterilization units 114 may apply one or more sterilization agents 108 to one or more areas 102 according to one or more models of one or more areas 102. In some embodiments, one or more sterilization units 114 may apply one or more sterilization agents 108 to one or more areas 102 in compliance with one or more sterilization protocols. In some embodiments, one or more sterilization units 114 may apply one or more sterilization agents 108 to one or more areas 102 according to one or more sterilization statuses assigned to the one or more areas 102. In some embodiments, one or more sterilization units 114 may apply one or more sterilization agents 108 to one or more areas 102 according to one or more readings obtained from one or more sensor units 118. In some embodiments, one or more sterilization units 114 may apply one or more sterilization agents 108 to one or more shadow areas present within one or more areas 102. In some embodiments, one or more sterilization units 114 may apply one or more sterilization agents 108 to one or more areas 102 according to one or more instructions associated with one or more survey units 110 that are stationary. In some embodiments, one or more sterilization units 114 may apply one or more sterilization agents 108 to one or more areas 102 according to one or more instructions associated with one or more survey units 110 that are mobile. In some embodiments, one or more sterilization units 114 may apply one or more sterilization agents 108 to one or more areas 102 according to one or more priorities assigned to the one or more areas 102. In some embodiments, one or more sterilization units 114 may apply one or more sterilization agents 108 to one or more areas 102 according to the presence or absence of one or more humans within the one or more areas 102. In some embodiments, one or more sterilization units 114 may apply one or more sterilization agents 108 that are identified to one or more areas 102. In some embodiments, one or more sterilization units 114 may apply one or more sterilization agents 108 to one or more areas 102 according to one or more time intervals that have elapsed since one or more sterilization agents 108 were previously applied within the one or more areas 102.

At operation 1804, the applying operation 1220 may include avoiding application of one or more sterilization agents 108 to one or more areas 102. In some embodiments, one or more sterilization units 114 may avoid application of one or more sterilization agents 108 to one or more areas 102. In some embodiments, one or more sterilization units 114 may avoid application of one or more sterilization agents 108 to one or more areas 102 according to one or more maps of the one or more areas 102. In some embodiments, one or more sterilization units 114 may avoid application of one or more sterilization agents 108 to one or more areas 102 according to one or more models of one or more areas 102. In some embodiments, one or more sterilization units 114 may avoid application of one or more sterilization agents 108 to one or more areas 102 in compliance with one or more sterilization protocols. In some embodiments, one or more sterilization units 114 avoid application of one or more sterilization agents 108 to one or more areas 102 according to one or more sterilization statuses assigned to the one or more areas 102. In some embodiments, one or more sterilization units 114 may avoid application of one or more sterilization agents 108 to one or more areas 102 according to one or more readings obtained from one or more sensor units 118. In some embodiments, one or more sterilization units 114 may avoid application of one or more sterilization agents 108 to one or more shadow areas present within one or more areas 102. In some embodiments, one or more sterilization units 114 may avoid application of one or more sterilization agents 108 to one or more areas 102 according to one or more instructions associated with one or more survey units 110 that are stationary. In some embodiments, one or more sterilization units 114 may avoid application of one or more sterilization agents 108 to one or more areas 102 according to one or more instructions associated with one or more survey units 110 that are mobile. In some embodiments, one or more sterilization units 114 may avoid application of one or more sterilization agents 108 to one or more areas 102 according to one or more priorities assigned to the one or more areas 102. In some embodiments, one or more sterilization units 114 may avoid application of one or more sterilization agents 108 to one or more areas 102 according to the presence or absence of one or more humans within the one or more areas 102. In some embodiments, one or more sterilization units 114 may avoid application of one or more sterilization agents 108 that are identified to one or more areas 102. In some embodiments, one or more sterilization units 114 may avoid application of one or more sterilization agents 108 to one or more areas 102 according to one or more time intervals that have elapsed since one or more sterilization agents 108 were previously applied within the one or more areas 102.

At operation 1806, the applying operation 1220 may include applying one or more sterilization agents 108 to one or more surfaces 106 within one or more areas 102. In some embodiments, one or more sterilization units 114 may apply one or more sterilization agents 108 to one or more surfaces 106 within one or more areas 102. In some embodiments, one or more sterilization units 114 may apply one or more sterilization agents 108 to one or more surfaces 106 within one or more areas 102 according to one or more maps of one or more areas 102. In some embodiments, one or more sterilization units 114 may apply one or more sterilization agents 108 to one or more surfaces 106 within one or more areas 102 according to one or more models of one or more areas 102. In some embodiments, one or more sterilization units 114 may apply one or more sterilization agents 108 to one or more surfaces 106 within one or more areas 102 in compliance with one or more sterilization protocols. In some embodiments, one or more sterilization units 114 may apply one or more sterilization agents 108 to one or more surfaces 106 within one or more areas 102 according to one or more sterilization statuses assigned to the one or more surfaces 106. In some embodiments, one or more sterilization units 114 may apply one or more sterilization agents 108 to one or more surfaces 106 within one or more areas 102 according to one or more readings obtained from one or more sensor units 118. In some embodiments, one or more sterilization units 114 may apply one or more sterilization agents 108 to one or more surfaces 106 within one or more shadow areas present within one or more areas 102. In some embodiments, one or more sterilization units 114 may apply one or more sterilization agents 108 to one or more surfaces 106 within one or more areas 102 according to one or more signals 112 associated with one or more survey units 110 that are stationary. In some embodiments, one or more sterilization units 114 may apply one or more sterilization agents 108 to one or more surfaces 106 within one or more areas 102 according to one or more signals 112 associated with one or more survey units 110 that are mobile. In some embodiments, one or more sterilization units 114 may apply one or more sterilization agents 108 to one or more surfaces 106 according to one or more priorities assigned to the one or more surfaces 106 within one or more areas 102. In some embodiments, one or more sterilization units 114 may apply one or more sterilization agents 108 to one or more surfaces 106 within one or more areas 102 according to whether one or more humans are present or absent within the one or more areas 102. In some embodiments, one or more sterilization units 114 may apply one or more sterilization agents 108 that are identified to one or more surfaces 106 within one or more areas 102. In some embodiments, one or more sterilization units 114 may apply one or more sterilization agents 108 to one or more surfaces 106 within one or more areas 102 according to one or more time intervals that have elapsed since one or more sterilization agents 108 were previously applied to one or more surfaces 106 within one or more areas 102.

At operation 1808, the applying operation 1220 may include avoiding application of one or more sterilization agents 108 to one or more surfaces 106 within one or more areas 102. In some embodiments, one or more sterilization units 114 may avoid application of one or more sterilization agents 108 to one or more surfaces 106 within one or more areas 102. In some embodiments, one or more sterilization units 114 may avoid application of one or more sterilization agents 108 to one or more surfaces 106 within one or more areas 102 according to one or more maps of one or more areas 102. In some embodiments, one or more sterilization units 114 may avoid application of one or more sterilization agents 108 to one or more surfaces 106 within one or more areas 102 according to one or more models of one or more areas 102. In some embodiments, one or more sterilization units 114 may avoid application of one or more sterilization agents 108 to one or more surfaces 106 within one or more areas 102 in compliance with one or more sterilization protocols. In some embodiments, one or more sterilization units 114 may avoid application of one or more sterilization agents 108 to one or more surfaces 106 within one or more areas 102 according to one or more sterilization statuses assigned to the one or more surfaces 106. In some embodiments, one or more sterilization units 114 may avoid application of one or more sterilization agents 108 to one or more surfaces 106 within one or more areas 102 according to one or more readings obtained from one or more sensor units 118. In some embodiments, one or more sterilization units 114 may avoid application of one or more sterilization agents 108 to one or more surfaces 106 within one or more shadow areas present within one or more areas 102. In some embodiments, one or more sterilization units 114 may avoid application of one or more sterilization agents 108 to one or more surfaces 106 within one or more areas 102 according to one or more signals 112 associated with one or more survey units 110 that are stationary. In some embodiments, one or more sterilization units 114 may avoid application of one or more sterilization agents 108 to one or more surfaces 106 within one or more areas 102 according to one or more signals 112 associated with one or more survey units 110 that are mobile. In some embodiments, one or more sterilization units 114 may avoid application of one or more sterilization agents 108 to one or more surfaces 106 according to one or more priorities assigned to the one or more surfaces 106 within one or more areas 102. In some embodiments, one or more sterilization units 114 may avoid application of one or more sterilization agents 108 to one or more surfaces 106 within one or more areas 102 according to whether one or more humans are present or absent within the one or more areas 102. In some embodiments, one or more sterilization units 114 may avoid application of one or more sterilization agents 108 that are identified to one or more surfaces 106 within one or more areas 102. In some embodiments, one or more sterilization units 114 may avoid application of one or more sterilization agents 108 to one or more surfaces 106 within one or more areas 102 according to one or more time intervals that have elapsed since one or more sterilization agents 108 were previously applied to one or more surfaces 106 within one or more areas 102.

At operation 1810, the applying operation 1220 may include applying one or more sterilization agents 108 to one or more objects 104 within one or more areas 102. In some embodiments, one or more sterilization units 114 may apply one or more sterilization agents 108 to one or more objects 104 within one or more areas 102. In some embodiments, one or more sterilization units 114 may apply one or more sterilization agents 108 to one or more objects 104 within one or more areas 102 according to one or more maps of one or more areas 102. In some embodiments, one or more sterilization units 114 may apply one or more sterilization agents 108 to one or more objects 104 within one or more areas 102 according to one or more models of one or more areas 102. In some embodiments, one or more sterilization units 114 may apply one or more sterilization agents 108 to one or more objects 104 within one or more areas 102 in compliance with one or more sterilization protocols. In some embodiments, one or more sterilization units 114 may apply one or more sterilization agents 108 to one or more objects 104 within one or more areas 102 according to one or more sterilization statuses assigned to the one or more areas 102. In some embodiments, one or more sterilization units 114 may apply one or more sterilization agents 108 to one or more objects 104 within one or more areas 102 according to one or more readings obtained from one or more sensor units 118. In some embodiments, one or more sterilization units 114 may apply one or more sterilization agents 108 to one or more objects 104 within one or more shadow areas present within one or more areas 102. In some embodiments, one or more sterilization units 114 may apply one or more sterilization agents 108 to one or more objects 104 within one or more areas 102 according to one or more signals 112 associated with one or more survey units 110 that are stationary. In some embodiments, one or more sterilization units 114 may apply one or more sterilization agents 108 to one or more objects 104 within one or more areas 102 according to one or more signals 112 associated with one or more survey units 110 that are mobile. In some embodiments, one or more sterilization units 114 may apply one or more sterilization agents 108 to one or more objects 104 within one or more areas 102 according to one or more priorities associated with the one or more objects 104. In some embodiments, one or more sterilization units 114 may apply one or more sterilization agents 108 to one or more objects 104 within one or more areas 102 according to whether one or more humans that are present or absent within the one or more areas 102. In some embodiments, one or more sterilization units 114 may apply one or more sterilization agents 108 that are identified to one or more objects 104 within one or more areas 102. In some embodiments, one or more sterilization units 114 may apply one or more sterilization agents 108 to one or more objects 104 within one or more areas 102 according to one or more time intervals that have elapsed since one or more sterilization agents 108 were previously applied within the one or more areas 102.

Figure 19:
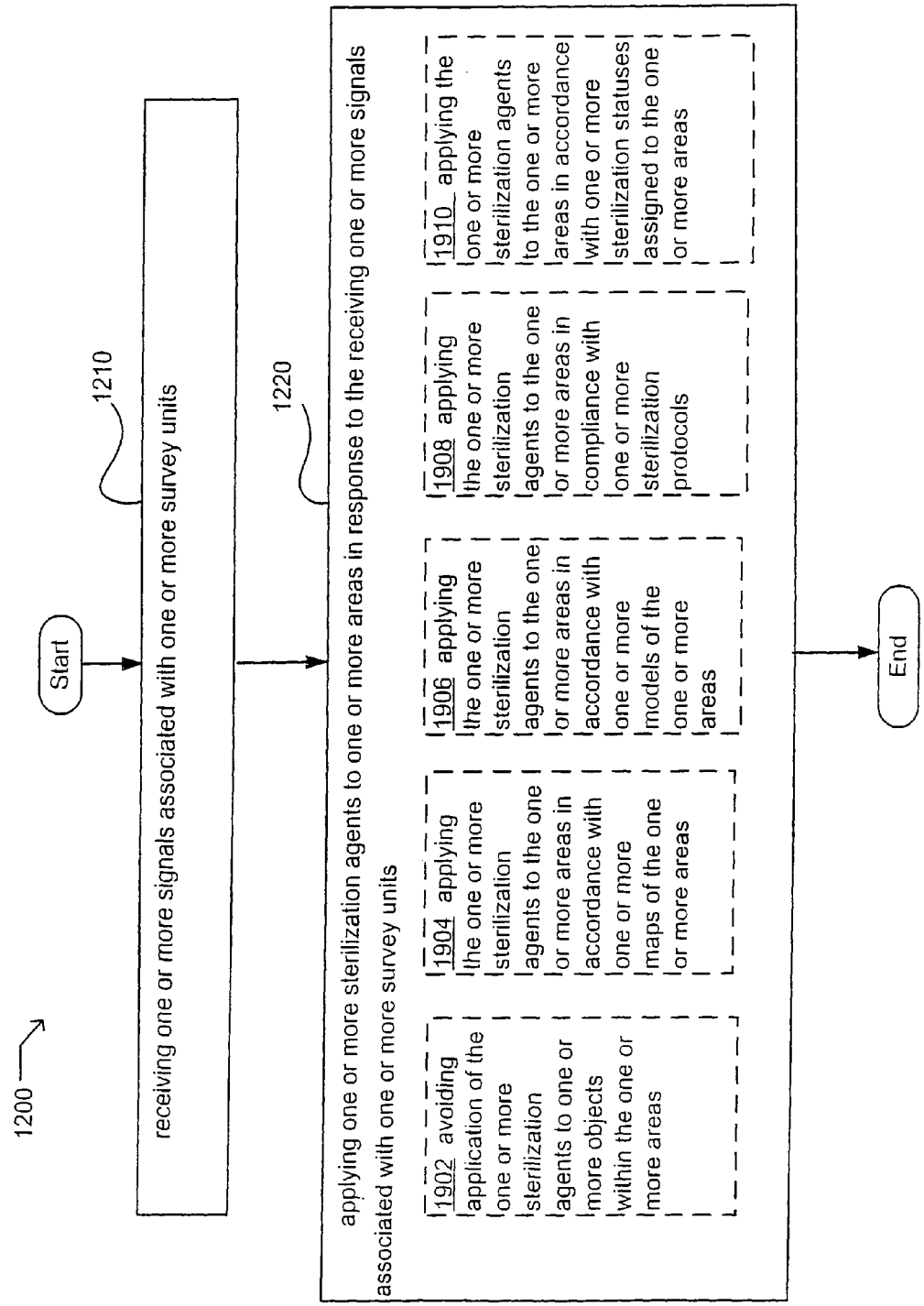
FIG. 19 illustrates an alternative embodiment of the example operation flow of FIG. 12.

FIG. 19 illustrates alternative embodiments of the example operational flow 1200 of FIG. 12. FIG. 19 illustrates example embodiments where the applying operation 1220 may include at least one additional operation. Additional operations may include an operation 1902, operation 1904, operation 1906, operation 1908 and/or operation 1910.

At operation 1902, the applying operation 1220 may include avoiding application of one or more sterilization agents 108 to one or more objects 104 within one or more areas 102. In some embodiments, one or more sterilization units 114 may avoid application of one or more sterilization agents 108 to one or more objects 104 within one or more areas 102. In some embodiments, one or more sterilization units 114 may avoid application of one or more sterilization agents 108 to one or more objects 104 within one or more areas 102 according to one or more maps of one or more areas 102. In some embodiments, one or more sterilization units 114 may avoid application of one or more sterilization agents 108 to one or more objects 104 within one or more areas 102 according to one or more models of one or more areas 102. In some embodiments, one or more sterilization units 114 may avoid application of one or more sterilization agents 108 to one or more objects 104 within one or more areas 102 in compliance with one or more sterilization protocols. In some embodiments, one or more sterilization units 114 may avoid application of one or more sterilization agents 108 to one or more objects 104 within one or more areas 102 according to one or more sterilization statuses assigned to the one or more areas 102. In some embodiments, one or more sterilization units 114 may avoid application of one or more sterilization agents 108 to one or more objects 104 within one or more areas 102 according to one or more readings obtained from one or more sensor units 118. In some embodiments, one or more sterilization units 114 may avoid application of one or more sterilization agents 108 to one or more objects 104 within one or more shadow areas present within one or more areas 102. In some embodiments, one or more sterilization units 114 may avoid application of one or more sterilization agents 108 to one or more objects 104 within one or more areas 102 according to one or more signals 112 associated with one or more survey units 110 that are stationary. In some embodiments, one or more sterilization units 114 may avoid application of one or more sterilization agents 108 to one or more objects 104 within one or more areas 102 according to one or more signals 112 associated with one or more survey units 110 that are mobile. In some embodiments, one or more sterilization units 114 may avoid application of one or more sterilization agents 108 to one or more objects 104 within one or more areas 102 according to one or more priorities associated with the one or more objects 104. In some embodiments, one or more sterilization units 114 may avoid application of one or more sterilization agents 108 to one or more objects 104 within one or more areas 102 according to whether one or more humans that are present or absent within the one or more areas 102. In some embodiments, one or more sterilization units 114 may avoid application of one or more sterilization agents 108 that are identified to one or more objects 104 within one or more areas 102. In some embodiments, one or more sterilization units 114 may avoid application of one or more sterilization agents 108 to one or more objects 104 within one or more areas 102 according to one or more time intervals that have elapsed since one or more sterilization agents 108 were previously applied within the one or more areas 102.

At operation 1904, the applying operation 1220 may include applying one or more sterilization agents 108 to one or more areas 102 in accordance with one or more maps of the one or more areas 102. In some embodiments, one or more sterilization units 114 may apply one or more sterilization agents 108 to one or more areas 102 in accordance with one or more maps of the one or more areas 102. In some embodiments, one or more sterilization units 114 may apply one or more sterilization agents 108 to one or more areas 102 according to one or more dimensions of the one or more areas 102 as substantially indicated by one or more maps. In some embodiments, one or more sterilization units 114 may apply one or more sterilization agents 108 to one or more areas 102 according to one or more positions of one or more surfaces 106 and/or one or more objects 104 within the one or more areas 102 as substantially indicated by one or more maps. In some embodiments, one or more sterilization units 114 may apply one or more sterilization agents 108 to one or more areas 102 according to one or more dimensions of the one or more areas 102 and one or more positions of one or more surfaces 106 and/or one or more objects 104 within the one or more areas 102 as substantially indicated by one or more maps. In some embodiments, one or more sterilization units 114 may avoid application of one or more sterilization agents 108 to one or more areas 102 according to one or more maps of the one or more areas 102. In some embodiments, one or more sterilization units 114 may apply one or more sterilization agents 108 to one or more surfaces 106 within one or more areas 102 according to one or more maps of the one or more areas 102. In some embodiments, one or more sterilization units 114 may avoid application of one or more sterilization agents 108 to one or more surfaces 106 within one or more areas 102 according to one or more maps of the one or more areas 102. In some embodiments, one or more sterilization units 114 may apply one or more sterilization agents 108 to one or more objects 104 within one or more areas 102 according to one or more maps of the one or more areas 102. In some embodiments, one or more sterilization units 114 may avoid application of one or more sterilization agents 108 to one or more objects 104 within one or more areas 102 according to one or more maps of the one or more areas 102. In some embodiments, one or more sterilization units 114 may apply one or more sterilization agents 108 to one or more shadow areas within one or more areas 102 according to one or more maps of the one or more areas 102. In some embodiments, one or more sterilization units 114 may apply one or more sterilization agents 108 to one or more areas 102 according one or more priorities of the one or more areas 102 as indicated on one or more maps of the one or more areas 102. In some embodiments, one or more sterilization units 114 may apply one or more sterilization agents 108 to one or more surfaces 106 within one or more areas 102 according one or more priorities of the one or more surfaces 106 as indicated on one or more maps. In some embodiments, one or more sterilization units 114 may apply one or more sterilization agents 108 to one or more portions of one or more areas 102 according one or more maps. In some embodiments, one or more sterilization units 114 may avoid application of one or more sterilization agents 108 to one or more portions of one or more areas 102 according one or more maps.

At operation 1906, the applying operation 1220 may include applying one or more sterilization agents 108 to one or more areas 102 in accordance with one or more models of the one or more areas 102. In some embodiments, one or more sterilization units 114 may apply one or more sterilization agents 108 to one or more areas 102 in accordance with one or more models of the one or more areas 102. In some embodiments, one or more sterilization units 114 may apply one or more sterilization agents 108 in accordance with one or more models of one or more areas 102 that provide one or more dimensions of the one or more areas 102. In some embodiments, one or more sterilization units 114 may apply one or more sterilization agents 108 in accordance with one or more models of one or more areas 102 that provide one or more positions of one or more surfaces 106 and/or one or more objects 104 within the one or more areas 102. In some embodiments, one or more sterilization units 114 may apply one or more sterilization agents 108 in accordance with one or more models of one or more areas 102 that provide the dimensions of the one or more areas 102 and one or more positions of one or more surfaces 106 and/or one or more objects 104 within the one or more areas 102. In some embodiments, one or more sterilization units 114 may apply one or more sterilization agents 108 in accordance with one or more models of one or more areas 102 that indicate where to apply one or more sterilization agents 108 within the one or more areas 102. In some embodiments, one or more sterilization units 114 may apply one or more sterilization agents 108 in accordance with one or more models of one or more areas 102 that indicate where not to apply one or more sterilization agents 108 within the one or more areas 102. In some embodiments, one or more sterilization units 114 may apply one or more sterilization agents 108 in accordance with one or more models of one or more areas 102 that indicate one or more surfaces 106 on which to apply one or more sterilization agents 108 within the one or more areas 102. In some embodiments, one or more sterilization units 114 may apply one or more sterilization agents 108 in accordance with one or more models of one or more areas 102 that indicate one or more surfaces 106 on which not to apply one or more sterilization agents 108 within the one or more areas 102. In some embodiments, one or more sterilization units 114 may apply one or more sterilization agents 108 in accordance with one or more models of one or more areas 102 that indicate one or more objects 104 on which to apply one or more sterilization agents 108 within the one or more areas 102. In some embodiments, one or more sterilization units 114 may apply one or more sterilization agents 108 in accordance with one or more models of one or more areas 102 that indicate one or more objects 104 on which not to apply one or more sterilization agents 108 within the one or more areas 102. In some embodiments, one or more sterilization units 114 may apply one or more sterilization agents 108 in accordance with one or more models of one or more areas 102 that include instructions to comply with one or more sterilization protocols. In some embodiments, one or more sterilization units 114 may apply one or more sterilization agents 108 in accordance with one or more models of one or more areas 102 that include one or more sterilization statuses assigned to one or more areas 102. In some embodiments, one or more sterilization units 114 may apply one or more sterilization agents 108 in accordance with one or more models of one or more areas 102 that include one or more readings obtained from one or more sensor units 118. In some embodiments, one or more sterilization units 114 may apply one or more sterilization agents 108 in accordance with one or more models of one or more areas 102 that indicate one or more locations of one or more shadow areas present within one or more areas 102. In some embodiments, one or more sterilization units 114 may apply one or more sterilization agents 108 in accordance with one or more models of one or more areas 102 that prioritize one or more areas 102 for sterilization. In some embodiments, one or more sterilization units 114 may apply one or more sterilization agents 108 in accordance with one or more models of one or more areas 102 that prioritize one or more surfaces 106 within one or more areas 102 for sterilization. In some embodiments, one or more sterilization units 114 may apply one or more sterilization agents 108 in accordance with one or more models of one or more areas 102 that include the presence of absence of one or more humans within one or more areas 102. In some embodiments, one or more sterilization units 114 may apply one or more sterilization agents 108 in accordance with one or more models of one or more areas 102 that indicate one or more portions of one or more areas 102 where one or more sterilization agents 108 should be applied. In some embodiments, one or more sterilization units 114 may apply one or more sterilization agents 108 in accordance with one or more models of one or more areas 102 that indicate one or more portions of one or more areas 102 where one or more sterilization agents 108 should not be applied. In some embodiments, one or more sterilization units 114 may apply one or more sterilization agents 108 in accordance with one or more models of one or more areas 102 that identify one or more sterilization agents 108 that should be applied to one or more areas 102. In some embodiments, one or more sterilization units 114 may apply one or more sterilization agents 108 in accordance with one or more models of one or more areas 102 that indicate one or more time intervals that have elapsed since one or more sterilization agents 108 were previously applied within one or more areas 102.

At operation 1908, the applying operation 1220 may include applying one or more sterilization agents 108 to one or more areas 102 in compliance with one or more sterilization protocols. In some embodiments, one or more sterilization units 114 may apply one or more sterilization agents 108 to one or more areas 102 in compliance with one or more sterilization protocols. In some embodiments, one or more sterilization units 114 may apply one or more sterilization agents 108 to one or more areas 102 in compliance with one or more sterilization protocols that specify the immediacy, latency, intensity and time-integrated intensity of sterilizing radiation that is to be applied within one or more areas 102 as a function of either relative or absolute location within the one or more areas 102. In some embodiments, one or more sterilization units 114 may apply one or more sterilization agents 108 to one or more areas 102 in compliance with one or more sterilization protocols that specify one or more types of sterilization agents 108 that are to be applied to one or more areas 102. In some embodiments, one or more sterilization units 114 may apply one or more sterilization agents 108 to one or more areas 102 in compliance with one or more sterilization protocols that specify one or more types of sterilization agents 108 that are not to be applied to one or more areas 102. In some embodiments, one or more sterilization units 114 may apply one or more sterilization agents 108 to one or more areas 102 in compliance with one or more sterilization protocols that specify the frequency with which one or more sterilization agents 108 are to be applied to one or more areas 102. In some embodiments, one or more sterilization units 114 may apply one or more sterilization agents 108 to one or more areas 102 in compliance with one or more sterilization protocols that specify the intensity and/or concentration that one or more types of sterilization agents 108 that are to be applied to one or more areas 102. In some embodiments, one or more sterilization units 114 may apply one or more sterilization agents 108 to one or more areas 102 in compliance with one or more sterilization protocols that specify the intensity with which one or more areas 102 are sterilized to account for high patient-hazard and/or high infectivity likelihood areas to ensure that such areas 102 receive rigorous and/or frequent sterilization treatment. In some embodiments, one or more sterilization units 114 may apply one or more sterilization agents 108 to one or more areas 102 in compliance with one or more sterilization protocols that are associated with how much time has passed since one or more areas 102 were last sterilized. In some embodiments, one or more sterilization units 114 may apply one or more sterilization agents 108 to one or more areas 102 in compliance with one or more sterilization protocols that call for sterilization of the one or more areas 102 at given time intervals.

At operation 1910, the applying operation 1220 may include applying one or more sterilization agents 108 to one or more areas 102 in accordance with one or more sterilization statuses assigned to the one or more areas 102. In some embodiments, one or more sterilization units 114 may apply one or more sterilization agents 108 to one or more areas 102 in accordance with one or more sterilization statuses assigned to the one or more areas 102. In some embodiments, one or more sterilization units 114 may apply one or more sterilization agents 108 to one or more areas 102 in accordance with one or more sterilization statuses assigned to the one or more areas 102 that can be relative to one or more sterilization levels assigned to the one or more areas 102. In some embodiments, one or more sterilization units 114 may apply one or more sterilization agents 108 to one or more areas 102 in accordance with one or more sterilization statuses that may include parameters for time of sterilization, frequency of sterilization, type of sterilization agent 108 to be applied, intensity of sterilization, use of multiple sterilization agents 108, risk-level assigned to one or more areas 102, types of contamination occurring within one or more areas 102, and/or disease-state of one or more patients within the one or more areas 102. In some embodiments, one or more sterilization units 114 may apply one or more sterilization agents 108 to one or more areas 102 in accordance with one or more sterilization statuses which indicate if the one or more areas 102 need to be sterilized or whether the one or more areas 102 satisfy the desired sterilization level.

Figure 20:
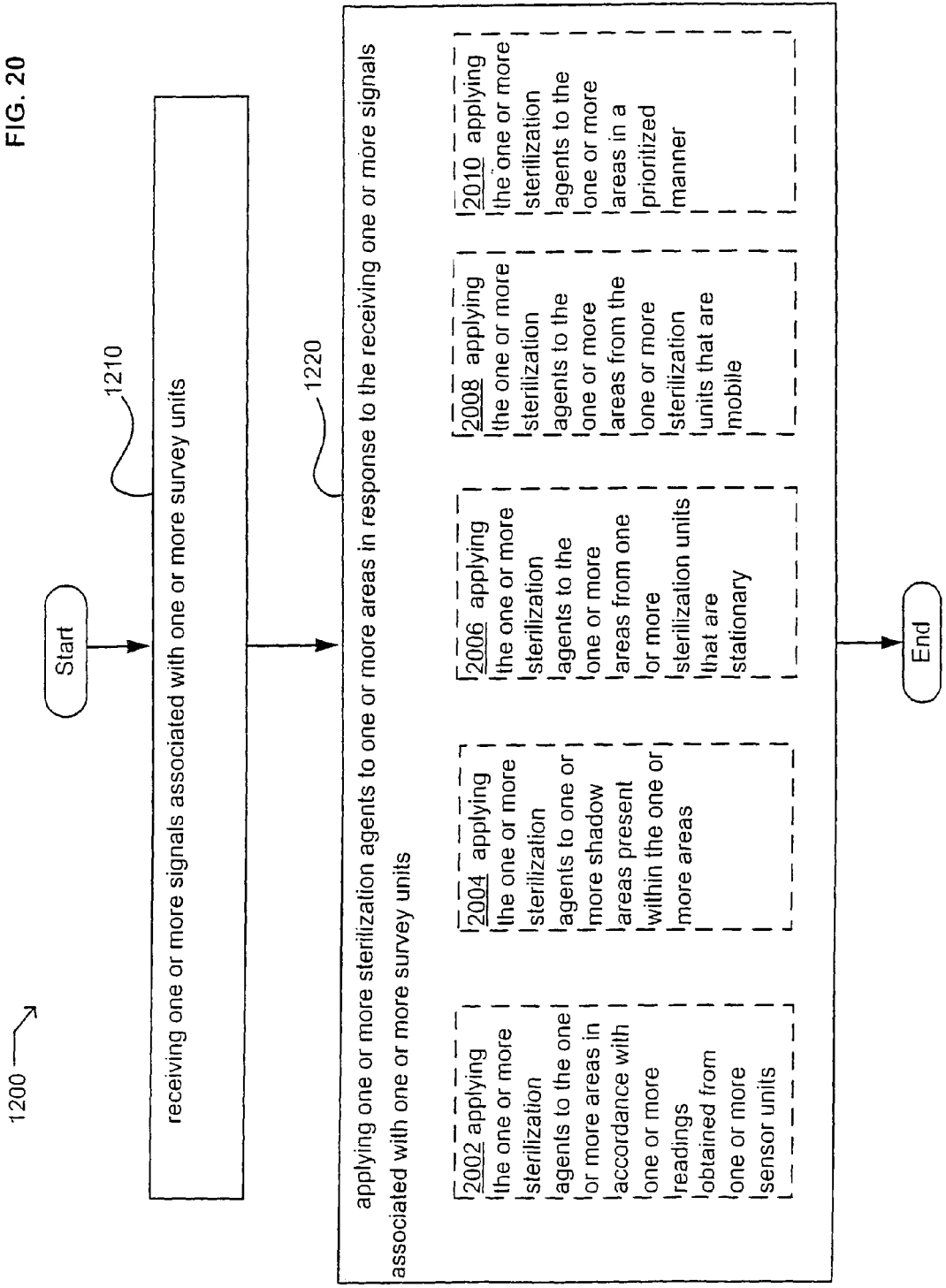
FIG. 20 illustrates an alternative embodiment of the example operation flow of FIG. 12.

FIG. 20 illustrates alternative embodiments of the example operational flow 1200 of FIG. 12. FIG. 20 illustrates example embodiments where the applying operation 1220 may include at least one additional operation. Additional operations may include an operation 2002, operation 2004, operation 2006, operation 2008 and/or operation 2010.

At operation 2002, the applying operation 1220 may include applying one or more sterilization agents 108 to one or more areas 102 in accordance with one or more readings obtained from one or more sensor units 118. In some embodiments, one or more sterilization units 114 may apply one or more sterilization agents 108 to one or more areas 102 in accordance with one or more readings obtained from one or more sensor units 118. In some embodiments, one or more sterilization units 114 may apply one or more sterilization agents 108 to one or more areas 102 in accordance with one or more readings obtained from one or more sensor units 118 that indicate one or more times when the one or more areas 102 were sterilized. In some embodiments, one or more sterilization units 114 may apply one or more sterilization agents 108 to one or more areas 102 in accordance with one or more readings obtained from one or more sensor units 118 that indicate how often one or more areas 102 are sterilized. In some embodiments, one or more sterilization units 114 may apply one or more sterilization agents 108 to one or more areas 102 in accordance with one or more readings obtained from one or more sensor units 118 that indicate the intensity with which one or more areas 102 are sterilized. In some embodiments, one or more sterilization units 114 may apply one or more sterilization agents 108 to one or more areas 102 in accordance with one or more readings obtained from one or more sensor units 118 that indicate whether or not one or more surfaces 106 within one or more areas 102 have been sterilized. In some embodiments, one or more sterilization units 114 may apply one or more sterilization agents 108 to one or more areas 102 in accordance with one or more readings obtained from one or more sensor units 118 that indicate one or more types of sterilization agents 108 that have been applied within one or more areas 102. In some embodiments, one or more sterilization units 114 may apply one or more sterilization agents 108 to one or more areas 102 in accordance with one or more readings obtained from one or more sensor units 118 that indicate one or more types of sterilization agents 108 that have been applied to one or more surfaces 106 within one or more areas 102. In some embodiments, one or more sterilization units 114 may apply one or more sterilization agents 108 to one or more areas 102 in accordance with one or more readings obtained from one or more sensor units 118 that indicate one or more types of sterilization agents 108 that have been applied to one or more objects 104 within one or more areas 102. In some embodiments, one or more sterilization units 114 may apply one or more sterilization agents 108 to one or more areas 102 in accordance with one or more readings obtained from one or more sensor units 118 that indicate one or more types of sterilization agents 108 that have been applied to one or more objects 104 and/or one or more surfaces 106 within one or more areas 102. In some embodiments, one or more sterilization units 114 may apply one or more sterilization agents 108 to one or more areas 102 in accordance with one or more readings obtained from one or more sensor units 118 that indicate one or more shadow areas present within one or more areas 102.

At operation 2004, the applying operation 1220 may include applying one or more sterilization agents 108 to one or more shadow areas present within the one or more areas 102. In some embodiments, one or more sterilization units 114 may apply one or more sterilization agents 108 to one or more shadow areas present within one or more areas 102.

At operation 2006, the applying operation 1220 may include applying one or more sterilization agents 108 to one or more areas 102 from one or more sterilization units 114 that are stationary. In some embodiments, one or more sterilization units 114 that are stationary may apply one or more sterilization agents 108 to one or more areas 102. In some embodiments, one or more sterilization units 114 may avoid application of one or more sterilization agents 108 to one or more areas 102. In some embodiments, one or more sterilization units 114 may apply one or more sterilization agents 108 to one or more surfaces 106 within one or more areas 102. In some embodiments, one or more sterilization units 114 may avoid applying one or more sterilization agents 108 to one or more surfaces 106 within one or more areas 102. In some embodiments, one or more sterilization units 114 may apply one or more sterilization agents 108 to one or more objects 104 within one or more areas 102. In some embodiments, one or more sterilization units 114 may avoid applying one or more sterilization agents 108 to one or more objects 104 within one or more areas 102. In some embodiments, one or more sterilization units 114 may apply one or more sterilization agents 108 according to one or more maps of one or more areas 102. In some embodiments, one or more sterilization units 114 may apply one or more sterilization agents 108 according to one or more models of one or more areas 102. In some embodiments, one or more sterilization units 114 may apply one or more sterilization agents 108 according to one or more sterilization protocols assigned to one or more areas 102. In some embodiments, one or more sterilization units 114 may apply one or more sterilization agents 108 according to one or more sterilization statuses assigned to one or more areas 102. In some embodiments, one or more sterilization units 114 may apply one or more sterilization agents 108 according to one or more readings obtained from one or more sensor units 118. In some embodiments, one or more sterilization units 114 may apply one or more sterilization agents 108 according to one or more locations of one or more shadow areas present within one or more areas 102.

In some embodiments, one or more sterilization units 114 may apply one or more sterilization agents 108 according to one or more priorities assigned to one or more areas 102 for sterilization. In some embodiments, one or more sterilization units 114 may apply one or more sterilization agents 108 according to one or more priorities assigned to one or more surfaces 106 within one or more areas 102 for sterilization. In some embodiments, one or more sterilization units 114 may apply one or more sterilization agents 108 according to whether one or more humans that are present or absent within one or more areas 102. In some embodiments, one or more sterilization units 114 may apply one or more sterilization agents 108 to one or more portions of one or more areas 102. In some embodiments, one or more sterilization units 114 may apply one or more sterilization agents 108 to one or more areas 102 according to one or more time intervals that have elapsed since one or more sterilization agents 108 were previously applied within the one or more areas 102.

At operation 2010, the applying operation 1220 may include applying one or more sterilization agents 108 to one or more areas 102 in a prioritized manner. In some embodiments, one or more sterilization units 114 may apply one or more sterilization agents 108 to one or more areas 102 in a prioritized manner. In some embodiments, one or more sterilization units 114 apply one or more sterilization agents 108 to one or more areas 102 according to the need for sterilization of the one or more areas 102. For example, an operating room may be sterilized before other areas 102 due to the existence of an emergency surgery that is to be done within the operating room. In some embodiments, one or more sterilization units 114 apply one or more sterilization agents 108 to one or more areas 102 according to the presence of a highly infectious agent within one or more areas 102. For example, an examination room in a hospital may be sterilized before other areas 102 due to the presence of a patient who is infected with smallpox within the examination room. In some embodiments, one or more sterilization units 114 apply one or more sterilization agents 108 to one or more areas 102 in conformance with a sterilization protocol.

Figure 21:
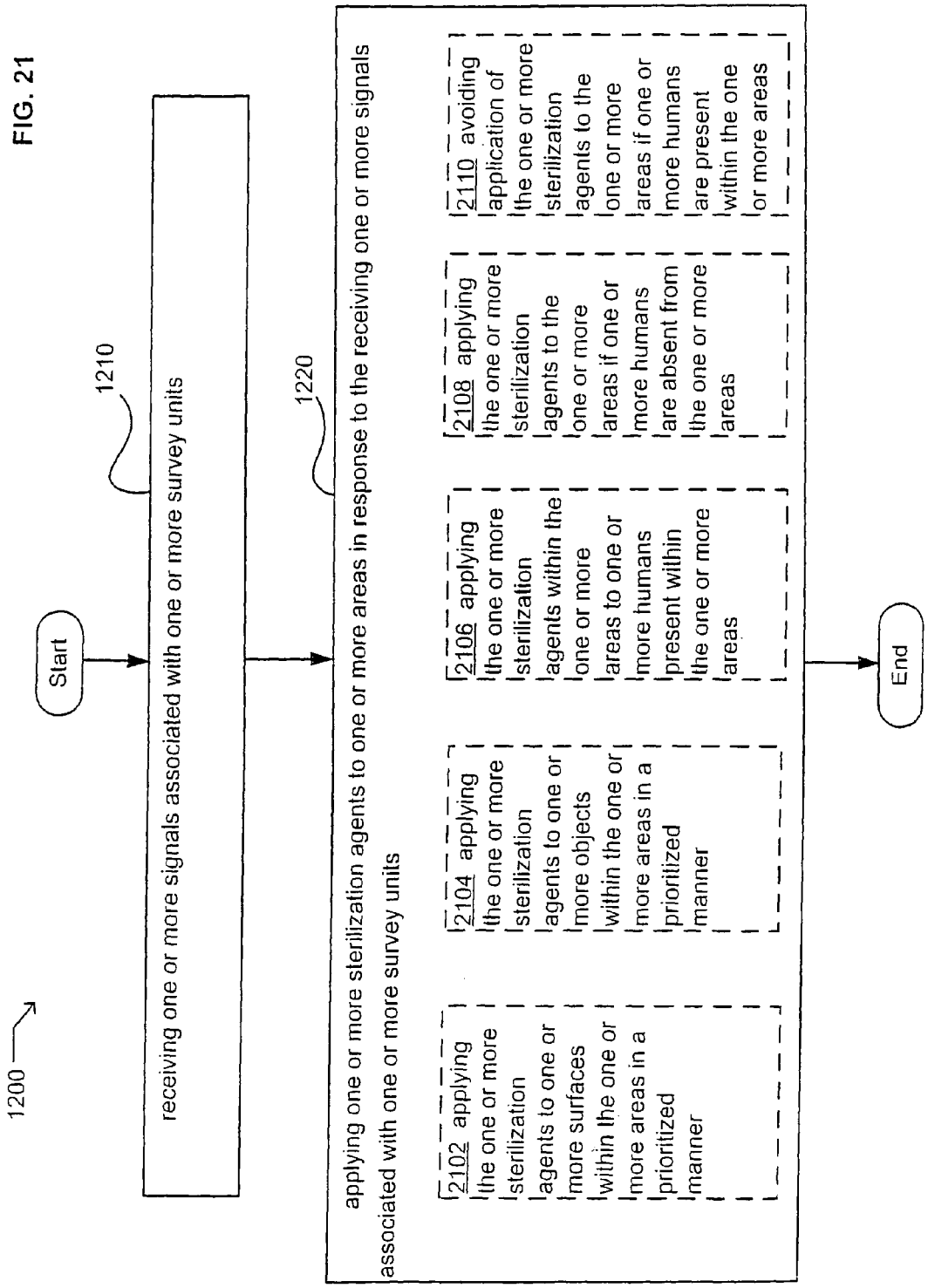
FIG. 21 illustrates an alternative embodiment of the example operation flow of FIG. 12.

FIG. 21 illustrates alternative embodiments of the example operational flow 1200 of FIG. 12. FIG. 21 illustrates example embodiments where the applying operation 1220 may include at least one additional operation. Additional operations may include an operation 2102, operation 2104, operation 2106, operation 2108 and/or operation 2110.

At operation 2102, the applying operation 1220 may include applying one or more sterilization agents 108 to one or more surfaces 106 within one or more areas 102 in a prioritized manner. In some embodiments, one or more sterilization units 114 may apply one or more sterilization agents 108 to one or more surfaces 106 within one or more areas 102 in a prioritized manner. In some embodiments, one or more sterilization units 114 apply one or more sterilization agents 108 to one or more surfaces 106 within one or more areas 102 according to the need for sterilization of the one or more surfaces 106. In some embodiments, one or more sterilization units 114 apply one or more sterilization agents 108 to one or more surfaces 106 within one or more areas 102 according to the presence of a highly infectious agent on the one or more surfaces 106. In some embodiments, one or more sterilization units 114 apply one or more sterilization agents 108 to one or more surfaces 106 in conformance with a sterilization protocol.

At operation 2104, the applying operation 1220 may include applying one or more sterilization agents 108 to one or more objects 104 within one or more areas 102 in a prioritized manner. In some embodiments, one or more sterilization units 114 may apply one or more sterilization agents 108 to one or more objects 104 within one or more areas 102 in a prioritized manner. In some embodiments, one or more sterilization units 114 apply one or more sterilization agents 108 to one or more objects 104 within one or more areas 102 according to the need for sterilization of the one or more objects 104. In some embodiments, one or more sterilization units 114 apply one or more sterilization agents 108 to one or more objects 104 within one or more areas 102 according to the presence of a highly infectious agent on the one or more objects 104. In some embodiments, one or more sterilization units 114 apply one or more sterilization agents 108 to one or more objects 104 in conformance with a sterilization protocol.

At operation 2106, the applying operation 1220 may include applying one or more sterilization agents 108 within one or more areas 102 to one or more humans present within the one or more areas 102. In some embodiments, one or more sterilization units 114 may apply one or more sterilization agents 108 to one or more humans present within one or more areas 102. In some embodiments, one or more sterilization agents 108 may be applied to one or more humans before they enter into one or more areas 102 that are sterile. In some embodiments, one or more sterilization agents 108 may be applied to one or more humans before they begin a sterile procedure. In some embodiments, one or more sterilization units 114 may apply one or more sterilization agents 108 to one or more humans who are contaminated with, or who have been exposed to, an infectious agent.

At operation 2108, the applying operation 1220 may include applying one or more sterilization agents 108 to one or more areas 102 if one or more humans are absent from the one or more areas 102. In some embodiments, one or more sterilization units 114 may apply one or more sterilization agents 108 to one or more areas 102 if one or more humans are absent from the one or more areas 102. In some embodiments, one or more sterilization units 114 may apply one or more sterilization agents 108 that are harmful to humans. Accordingly, human exposure to harmful sterilization agents 108 can be reduced or eliminated.

At operation 2110, the applying operation 1220 may include avoiding application of one or more sterilization agents 108 to one or more areas 102 if one or more humans are present within the one or more areas 102. In some embodiments, one or more sterilization units 114 may avoid application of one or more sterilization agents 108 to one or more areas 102 if one or more humans are present within the one or more areas 102. In some embodiments, one or more sterilization units 114 that are in the process of applying one or more sterilization agents 108 to one or more areas 102 may stop the application upon entry of one or more humans into the one or more areas 102. In some embodiments, one or more sterilization units 114 may abandon or delay applying one or more sterilization agents 108 to one or more areas 102 if one or more humans are present within the one or more areas 102.

Figure 22:
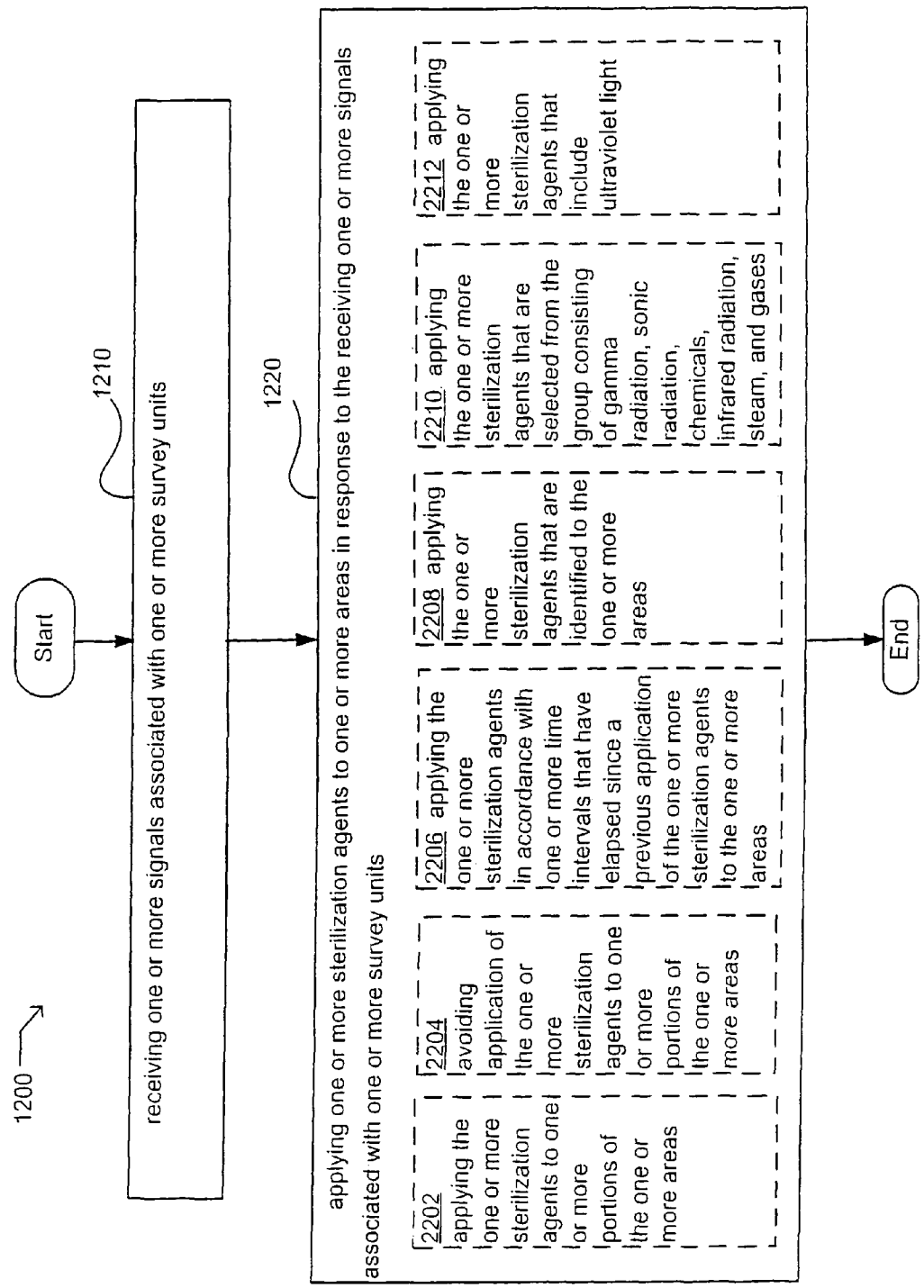
FIG. 22 illustrates an alternative embodiment of the example operation flow of FIG. 12.

FIG. 22 illustrates alternative embodiments of the example operational flow 1200 of FIG. 12. FIG. 22 illustrates example embodiments where the applying operation 1220 may include at least one additional operation. Additional operations may include an operation 2202, operation 2204, operation 2206, operation 2208, operation 2210 and/or operation 2212.

At operation 2202, the applying operation 1220 may include applying one or more sterilization agents 108 to one or more portions of one or more areas 102. In some embodiments, one or more sterilization units 114 may apply one or more sterilization agents 108 to one or more portions of one or more areas 102. In some embodiments, a first type of sterilization agent 108 is applied to one or more first portions of one or more areas 102 and a second type of sterilization agent 108 is applied to one or more second portions of one or more areas 102. Accordingly, different types of sterilization agents 108 may be applied to different portions of one or more areas 102. In some embodiments, activities may be conducted within one or more portions of one or more areas 102 that involve highly infective agents and/or that produce high levels of contamination within the one or more portions of the one or more areas 102. Accordingly, one or more sterilization agents 108 may be applied to those one or more portions of one or more areas 102 more frequently than to other portions of the one or more areas which are not exposed to high infectivity agents or high levels of contamination. For example, one or more sterilization agents 108 may be applied to one or more benches within a laboratory more frequently than to one or more desks within the laboratory 102.

At operation 2204, the applying operation 1220 may include avoiding application of one or more sterilization agents 108 to one or more portions of one or more areas 102. In some embodiments, one or more sterilization units 114 may avoid application of one or more sterilization agents 108 to one or more portions of one or more areas 102. In some embodiments, one or more sterilization agents 108 are not applied to one or more portions of one or more areas 102. For example, in some embodiments, one or more sterilization agents 108 are not be applied to one or more portions of one or more areas 102 in which laboratory specimens are cultured. Examples of such areas may be found in hospital laboratories, research laboratories, tissue culture laboratories, and the like. In some embodiments, one or more types of sterilization agents 108 are not be applied to one more first portions of one or more areas 102 but other types of sterilization agents 108 can be applied to the one or more first portions of the one or more areas 102. For example, in some embodiments, one or more sterilization agents 108 that would damage one or more portions of one or more areas 102 are not applied to the one or more portions of the one or more areas 102.

At operation 2206, the applying operation 1220 may include applying one or more sterilization agents 108 in accordance with one or more time intervals that have elapsed since a previous application of the one or more sterilization agents 108 to one or more areas 102. In some embodiments, one or more sterilization units 114 may apply one or more sterilization agents 108 in accordance with one or more time intervals that have elapsed since a previous application of the one or more sterilization agents 108 to one or more areas 102. In some embodiments, one or more sterilization units 114 may apply one or more sterilization agents 108 in compliance with one or more sterilization protocols assigned to the one or more areas 102. In some embodiments, one or more time intervals that have elapsed since one or more sterilization agents 108 were previously applied within one or more areas 102 can indicate when one or more sterilization agents 108 should be applied to the one or more areas 102. In some embodiments, one or more time intervals that have elapsed since one or more sterilization agents 108 were previously applied within one or more areas 102 can indicate what type or types of sterilization agents 108 should be applied to the one or more areas 102. In some embodiments, one or more time intervals that have elapsed since one or more sterilization agents 108 were previously applied within one or more areas 102 can indicate what type or types of sterilization agents 108 should not be applied to the one or more areas 102.

At operation 2208, the applying operation 1220 may include applying one or more sterilization agents 108 that are identified to one or more areas 102. In some embodiments, one or more sterilization units 114 may apply one or more sterilization agents 108 that are identified to one or more areas 102. In some embodiments, one or more areas 102 may include one or more types of contaminants that are preferably treated with one or more types of sterilization agents 108 as compared to other types of sterilization agents 108. Accordingly, in some embodiments, one or more types of sterilization agents 108 that are identified are selected for application within one or more areas 102 based on the identity of one or more contaminants for which the one or more sterilization agents 108 are to be used. In some embodiments, one or more types of sterilization agents 108 that are identified are selected for application within one or more areas 102 based on the characteristics of the one or more areas 102, the characteristics of one or more objects 104 within the one or more areas 102, the characteristics of one or more surfaces 106 within the one or more areas 102, and the like. For example, in some embodiments, one or more sterilization agents 108 that are identified are selected which will not be harmful to one or more areas 102. For example, one or more sterilization agents 108 will be selected that will not dissolve one or more objects 104 within one or more areas 102 to which one or more sterilization agents 108 are to be applied. In some embodiments, one or more sterilization agents 108 that are identified are selected which will have greater effectiveness in sterilizing one or more areas 102. For example, a sterilization agent 108 that is a gas, such as ethylene oxide, may be applied to one or more areas 102 that are porous.

At operation 2210, the applying operation 1220 may include applying one or more sterilization agents 108 that are selected from the group consisting of gamma radiation, sonic radiation, chemicals, infrared radiation, steam, and gases. In some embodiments, one or more sterilization units 114 may apply one or more sterilization agents 108 that are selected from the group consisting of gamma radiation, sonic radiation, chemicals, infrared radiation, steam, and gases. In some embodiments, one or more sterilization units 114 can apply one or more sterilization agents 108 that are gamma radiation, sonic radiation, chemicals, infrared radiation, steam, gases, and substantially any combination thereof.

At operation 2212, the applying operation 1220 may include applying one or more sterilization agents 108 that include ultraviolet light. In some embodiments, one or more sterilization units 114 may apply one or more sterilization agents 108 that include ultraviolet light. In some embodiments, one or more sterilization units 114 can emit sterilizing radiation substantially constantly. In some embodiments, one or more sterilization units 114 can emit sterilizing radiation as a pulse. In some embodiments, one or more sterilization units 114 can emit numerous types and/or combinations of sterilizing radiation, such as ultraviolet light and/or gamma radiation. In some embodiments, one or more sterilization units 114 can emit ultraviolet light having wavelengths between 100 nanometers and 400 nanometers and/or substantially any combination of wavelengths between 100 nanometers and 400 nanometers. In other embodiments, one or more sterilization units 114 can emit ultraviolet light having wavelengths between 180 nanometers and 300 nanometers and/or substantially any combination of wavelengths between 180 nanometers and 300 nanometers. In some embodiments, one or more sterilization units 114 can emit ultraviolet light having wavelengths between 255 nanometers and 280 nanometers and/or substantially any combination of wavelengths between 255 nanometers and 280 nanometers. In some embodiments, one or more sterilization units 114 can emit ultraviolet light having wavelengths between 250 nanometers and 280 nanometers and/or substantially any combination of wavelengths between 250 nanometers and 280 nanometers. In other embodiments, one or more sterilization units 114 can emit ultraviolet light having wavelengths that are centered, but asymmetric, and about 265 nanometers and/or substantially any combination of wavelengths of such light. In some embodiments, one or more sterilization units 114 can exclude the emission of one or more wavelengths of radiation.

Figure 23:
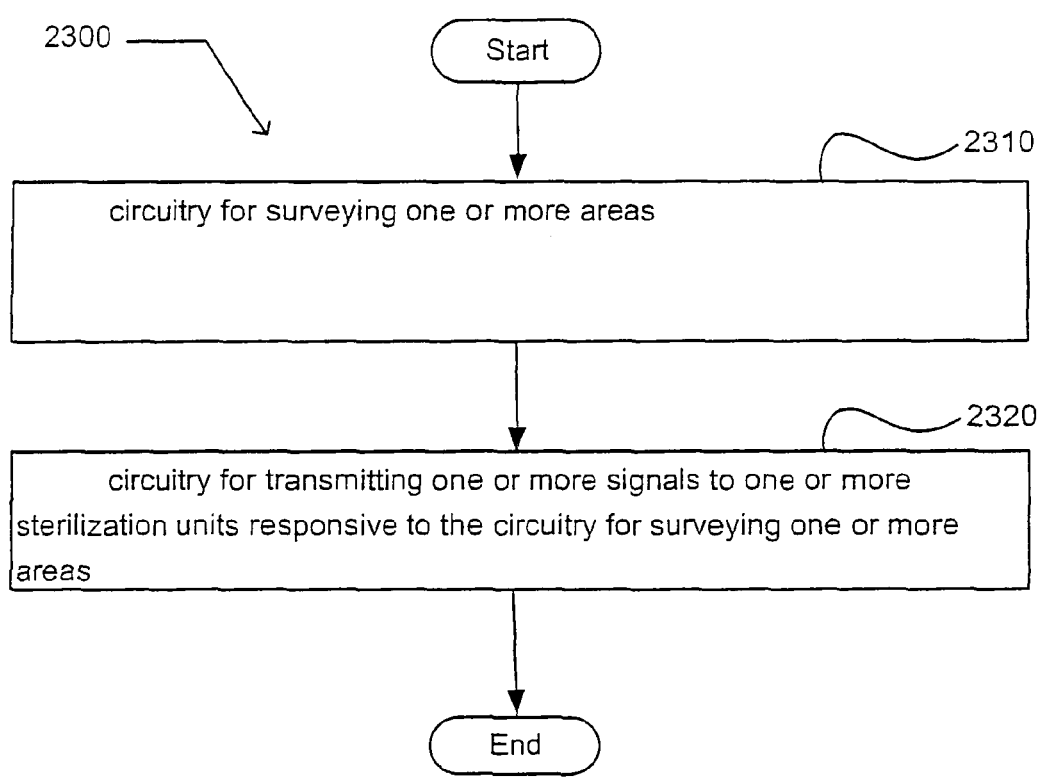
FIG. 23 illustrates an operational flow representing example operations related to sterilization systems.

FIG. 23 illustrates an operational flow 2300 representing examples of operations that are related to the performance of a sterilization method. In FIG. 23 and in following figures that include various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 2300 includes an operation 2310 involving circuitry for surveying one or more areas 102. In some embodiments, the circuitry for surveying one or more areas 102 can survey one area 102. In some embodiments, the circuitry for surveying one or more areas 102 can survey one or more areas 102. In some embodiments, the circuitry for surveying one or more areas 102 can survey one portion of one area 102. In some embodiments, the circuitry for surveying one or more areas 102 can survey one or more portions of one or more areas 102. In some embodiments, the circuitry for surveying one or more areas 102 can map one or more areas 102. In some embodiments, the circuitry for surveying one or more areas 102 can model one or more areas 102.

The operational flow 2300 also includes an operation 2320 involving circuitry for transmitting one or more signals to one or more sterilization units responsive to the circuitry for surveying one or more areas 102. In some embodiments, the circuitry for transmitting can transmit one or more signals 112 to one or more sterilization units 114. For example, in some embodiments, the circuitry for transmitting can transmit one signal 112 to one sterilization unit 114. In some embodiments, the circuitry for transmitting can transmit more than one signal 112 to one sterilization unit 114. In other embodiments, the circuitry for transmitting can transmit one signal 112 to more than one sterilization unit 114.

Figure 24:
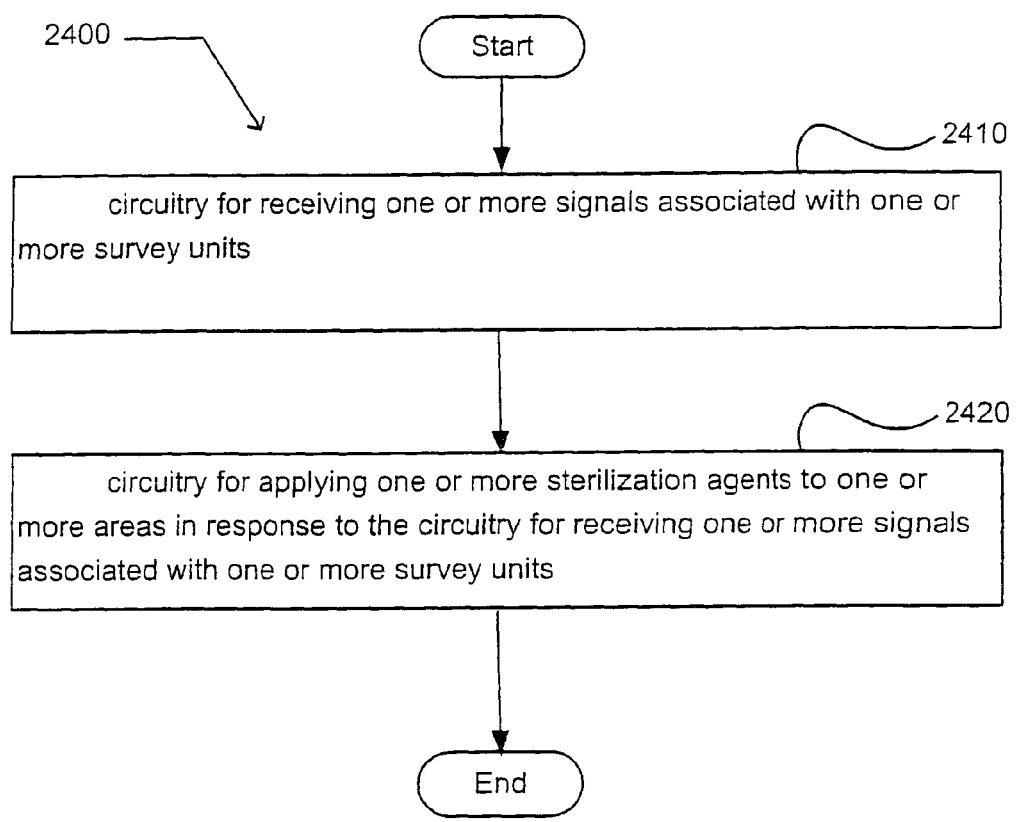
FIG. 24 illustrates an operational flow representing example operations related to sterilization systems.

FIG. 24 illustrates an operational flow 2400 representing examples of operations that are related to the performance of a sterilization method. In FIG. 24 and in following figures that include various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 2400 includes an operation 2410 involving circuitry for receiving one or more signals associated with one or more survey units 110. In some embodiments, the circuitry for receiving one or more signals 112 associated with one or more survey units 110 can receive one signal 112 from one survey unit 110. In some embodiments, the circuitry for receiving one or more signals 112 associated with one or more survey units 110 can receive one or more signals 112 from one survey unit 110. In some embodiments, the circuitry for receiving one or more signals 112 associated with one or more survey units 110 can receive one or more signals 112 from one or more survey units 110.

The operational flow 2400 also includes an operation 2420 involving circuitry for applying one or more sterilization agents to one or more areas in response to the circuitry for receiving one or more signals associated with one or more survey units 110. In some embodiments, the circuitry for applying one or more sterilization agents 108 to one or more areas 102 in response to the circuitry for receiving one or more signals 112 associated with one or more survey units 110 can direct application of one or more sterilization agents 108 to one or more areas 102. In some embodiments, the circuitry for applying one or more sterilization agents 108 to one or more areas 102 in response to the circuitry for receiving one or more signals 112 associated with one or more survey units 110 can direct application of one sterilization agent 108 to one area 102. In some embodiments, the circuitry for applying one or more sterilization agents 108 to one or more areas 102 in response to the circuitry for receiving one or more signals 112 associated with one or more survey units 110 can direct application of one or more sterilization agents 108 to one area 102. In some embodiments, the circuitry for applying one or more sterilization agents 108 to one or more areas 102 in response to the circuitry for receiving one or more signals 112 associated with one or more survey units 110 can direct application of one sterilization agent 108 to one or more areas 102.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

Although user 122 is shown/described herein as a single illustrated figure, those skilled in the art will appreciate that user 122 may be representative of a human user, a robotic user (e.g., computational entity), and/or substantially any combination thereof (e.g., a user may be assisted by one or more robotic agents). In addition, user 122, as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A system comprising:
   one or more survey units configured to produce one or more three-dimensional models of one or more portions of one or more areas;
   one or more sterilization units; and
   one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas.

2. The system of claim 1, wherein the one or more survey units configured to produce one or more three-dimensional models of one or more portions of one or more areas comprises:
   one or more survey units configured to produce one or more three-dimensional models of one or more portions of one or more rooms.

3. The system of claim 1, wherein the one or more survey units configured to produce one or more three-dimensional models of one or more portions of one or more areas comprises:
   one or more survey units configured to produce one or more three-dimensional models that indicate one or more positions of one or more objects within one or more areas.

4. The system of claim 1, wherein the one or more survey units configured to produce one or more three-dimensional models of one or more portions of one or more areas comprises:
   one or more survey units configured to produce one or more three-dimensional models that indicate one or more positions of one or more surfaces within one or more areas.

5. The system of claim 1, wherein the one or more survey units configured to produce one or more three-dimensional models of one or more portions of one or more areas comprises:
   one or more survey units that is associated with one or more sensors and that is configured to create one or more three-dimensional models of one or more portions of one or more areas based at least partly on information received from the one or more sensors.

6. The system of claim 1, wherein the one or more survey units configured to produce one or more three-dimensional models of one or more portions of one or more areas comprises:
   one or more stationary-type survey units configured to produce one or more three-dimensional models of one or more portions of one or more areas.

7. The system of claim 1, wherein the one or more survey units configured to produce one or more three-dimensional models of one or more portions of one or more areas comprises:
   one or more mobile-type survey units configured to produce one or more three-dimensional models of one or more portions of one or more areas.

8. The system of claim 1, wherein the one or more sterilization units comprises:
   one or more mobile-type sterilization units.

9. The system of claim 1, wherein the one or more sterilization units comprises:
   one or more stationary-type sterilization units.

10. The system of claim 1, wherein the one or more processing components are included within the one or more sterilization units.

11. The system of claim 1, wherein the one or more processing components are included within the one or more survey units.

12. The system of claim 1, wherein the one or more sterilization units comprises:
   one or more sterilization units configured to apply one of more of the following types of sterilization agents: gamma radiation, sonic radiation, chemical, infrared radiation, steam, gas, and/or ultraviolet light.

13. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:
   one or more processing components configured to at least (i) signal the one or more sterilization units to apply at least one selected sterilization agent based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas.

14. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:
  one or more processing components configured to at least (i) signal the one or more sterilization units to apply one or more sterilization agents based at least partly on the one or more three-dimensional models and on one or more sterilization protocols, at least partly in response to one or more humans being absent from at least one portion of the one or more areas and (ii) signal the one or more sterilization units to avoid applying one or more sterilization agents at least partly in response to one or more humans being present within at least one portion of the one or more areas.

15. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:
  one or more processing components configured to at least (i) signal the one or more sterilization units to apply one or more sterilization agents based at least partly on the one or more three-dimensional models and on at least one determination that at least one specified time interval has elapsed, at least partly in response to one or more humans being absent from at least one portion of the one or more areas and (ii) signal the one or more sterilization units to avoid applying one or more sterilization agents at least partly in response to one or more humans being present within at least one portion of the one or more areas.

16. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:
  one or more processing components configured to at least (i) signal the one or more sterilization units to apply one or more sterilization agents based at least partly on the one or more three-dimensional models and on at least one sterilization status, at least partly in response to one or more humans being absent from at least one portion of the one or more areas and (ii) signal the one or more sterilization units to avoid applying one or more sterilization agents at least partly in response to one or more humans being present within at least one portion of the one or more areas.

17. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:
  one or more processing components configured to at least (i) signal the one or more sterilization units to apply in a specified order of priority one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas.

18. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:
  one or more processing components configured to at least (i) signal the one or more sterilization units to apply one or more sterilization agents to one or more objects based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas.

19. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:
  one or more processing components configured to at least (i) signal the one or more sterilization units to apply one or more sterilization agents to one or more surfaces based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas.

20. The system of claim 1, wherein the one or more processing components configured to at least (i) signal the one or more sterilization units to apply one or more sterilization agents based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas comprises:

one or more processing components configured to at least (i) signal the one or more sterilization units to apply one or more sterilization agents to one or more portions of the one or more areas while avoiding at least one other portion of the one or more areas based at least partly on the one or more three-dimensional models at least partly in response to one or more humans being absent from at least one portion of the one or more areas and (ii) signal the one or more sterilization units to avoid applying one or more sterilization agents at least partly in response to one or more humans being present within at least one portion of the one or more areas.

21. The system of claim 1, further comprising:
one or more sensors.

\* \* \* \* \*